(12) United States Patent
Forsell

(10) Patent No.: US 11,337,813 B2
(45) Date of Patent: *May 24, 2022

(54) IMPLANT COMPRISING AN EXPANDABLE SECTION

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 394 days.

This patent is subject to a terminal disclaimer.

(21) Appl. No.: 16/449,569

(22) Filed: Jun. 24, 2019

(65) Prior Publication Data

US 2019/0374344 A1    Dec. 12, 2019

Related U.S. Application Data

(63) Continuation of application No. 14/929,451, filed on Nov. 2, 2015, now Pat. No. 10,327,902, which is a continuation of application No. 13/147,080, filed as application No. PCT/SE2010/050092 on Jan. 29, 2010, now Pat. No. 9,173,739.

(30) Foreign Application Priority Data

Jan. 29, 2009  (SE) ..................... 0900097-7
Jan. 29, 2009  (SE) ..................... 0900098-5

(51) Int. Cl.
    *A61F 2/26* (2006.01)

(52) U.S. Cl.
    CPC ........ *A61F 2/26* (2013.01); *A61F 2250/0001* (2013.01); *A61F 2250/001* (2013.01); *A61F 2250/0003* (2013.01); *A61F 2250/0007* (2013.01); *A61F 2250/0013* (2013.01); *A61F 2250/0026* (2013.01)

(58) Field of Classification Search
    CPC ................ A61F 2/26; A61F 2250/0003; A61F 2250/0007
    See application file for complete search history.

(56) References Cited

U.S. PATENT DOCUMENTS

| 9,017,245 B2* | 4/2015 | Forsell | ...................... A61F 2/26 600/40 |
| 9,901,449 B2* | 2/2018 | Forsell | .................. A61F 2/0077 |
| 10,327,902 B2* | 6/2019 | Forsell | ...................... A61F 2/26 |

* cited by examiner

*Primary Examiner* — John P Lacyk

(57) ABSTRACT

A method for implanting a non-invasively and post-operatively adjustable penile implant in a penis of a patient, the implant comprising an expandable portion having a hollow portion adapted to receive a fluid, thereby allowing the expandable portion to be adjustable from a collapsed state into an expanded state. The method comprises the steps of:
placing a proximal portion of said hollow portion in at least one corpus cavernosum, such that said proximal portion substantially extend on the inside of the male person when implanted in the penis;
placing a distal portion of said hollow portion in the at least one corpus cavernosum such that said distal portion substantially extends on the outside of the male person when implanted in the penis, wherein the distal portion is placed with an invagination extending into the hollow portion in the collapsed state, and wherein said invagination is adapted to expand the hollow body in a length direction of the penile implant in the expanded state.

20 Claims, 26 Drawing Sheets

302

302

L₁
306  L₂  302

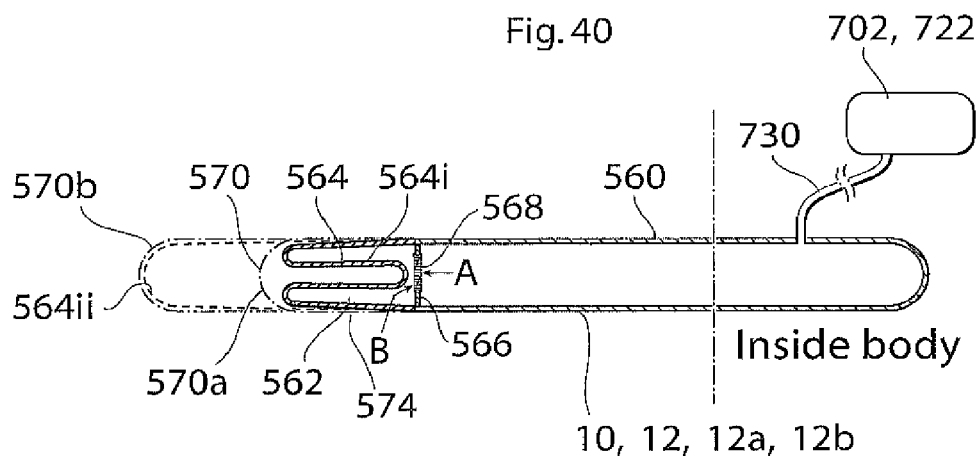
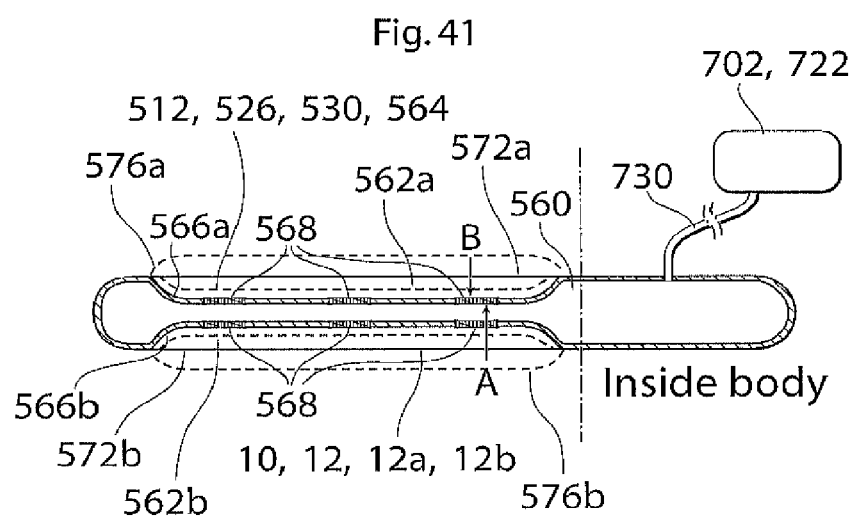
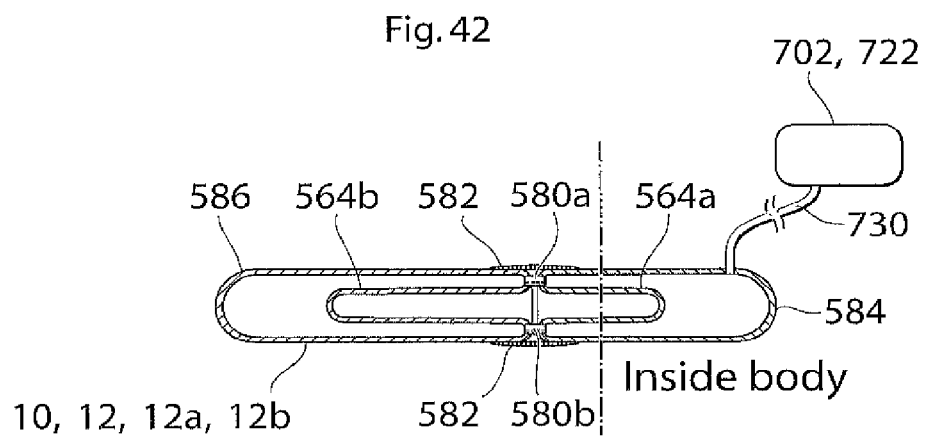

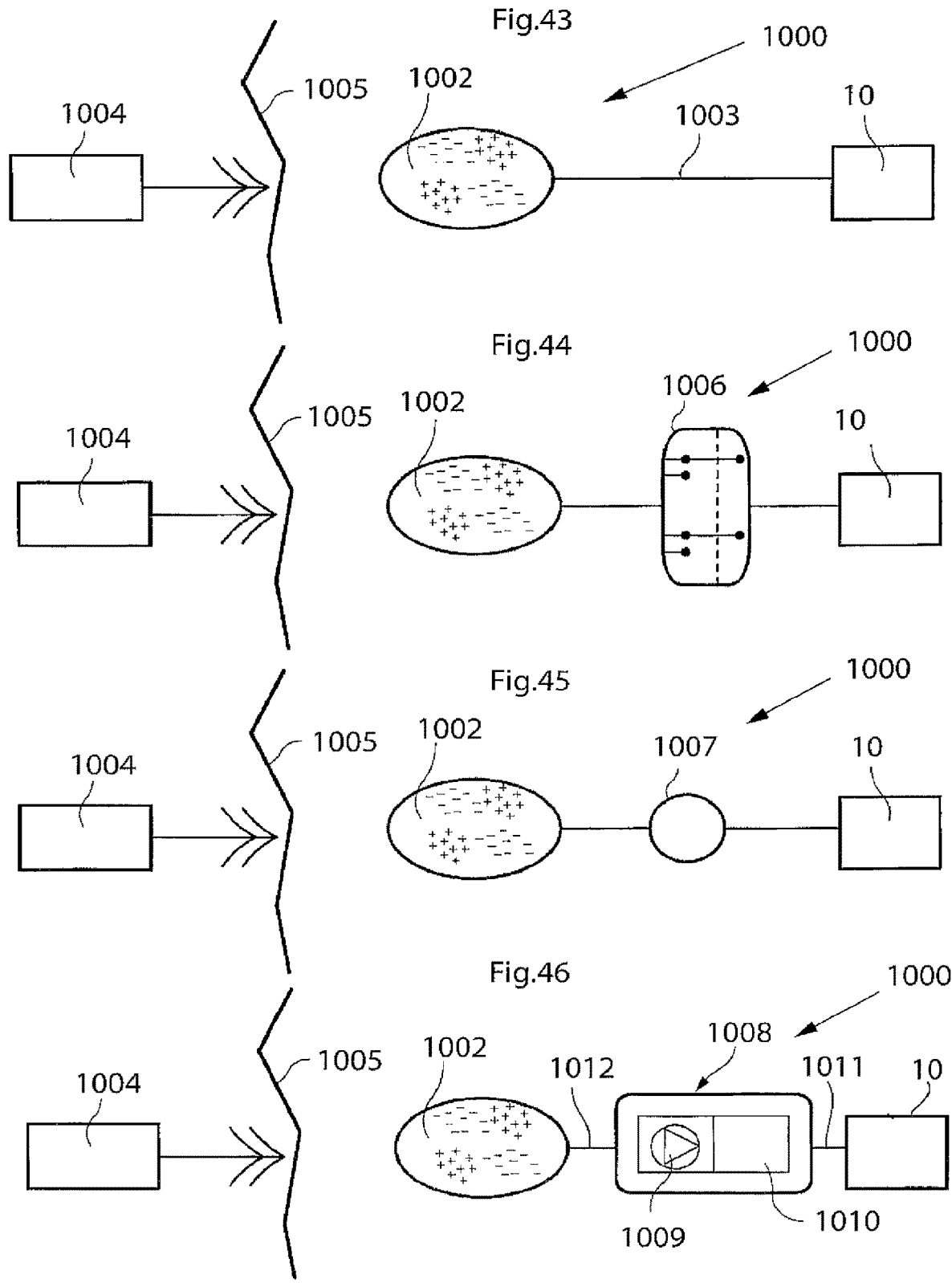

IMPLANT COMPRISING AN EXPANDABLE SECTION

This application is a continuation U.S. application Ser. No. 14/929451, filed Nov. 2, 2015, which is a continuation of U.S. application Ser. No. 13/147080 (now U.S. Pat. No. 9173739), filed 30 Sep. 2011, which is the U.S. national phase of International Application No. PCT/SE2010/050092, filed 29 Jan. 2010, which designated the U.S. and claims priority to Swedish application Nos. 0900097-7, filed 29 Jan. 2009 and 0900098-5, filed 29 Jan. 2009, the entire contents of each of which are hereby incorporated by reference.

TECHNICAL FIELD

The present invention relates to an implantable device, in particular an adjustable implantable device, in particular a penile implant for curing erectile impotence, a system comprising such a device and methods of implanting such a device and system.

BACKGROUND

As regards implants, and in particular adjustable implants and penile implants for curing erectile impotence, known from the background art, there are a number of areas or aspects where there is room for improvement.

One problem often encountered is the formation of fibrotic tissue or accumulation of fibrotic cells on the surface of the implant. The formation of such tissue on the surface of an adjustable implant or a penile implant may negatively influence the function of the implant, e.g. if such tissue is formed on a part of the surface that is collapsible and/or expandable.

In the background art expandable/collapsible breast implants are known, see e.g. U.S. Pat. No. 6,875,233 B1. The pleats of the implant described in this document may be prone to be bridged by fibrotic tissue which may impede the function of the implant. Further, the technique shown in this document may be unsuitable for use in an implant e.g. a penile implant since the conditions and demands may differ between penile implants and breast implants.

See also U.S. Pat. No. 4,424,807 which shows a penile implant where the folded or overlapped portions 50 and the folded ends 44 and 46 may be prone to be bridged or covered by fibrotic tissue which may impede the function of the implant. Another problem often encountered with previously known implants, e.g. in connection with organ or breast implants and especially in connection with penile implants, is that there is a risk that the implant breaks or gets damaged when it is subjected to bending, pressure or other influence. An adjustable implant may e.g. be subjected to such influences in its relaxed or inactivated state and/or in its expanded or activated state and this may cause breaking or other damage. A penile implant is e.g. often subjected to bending in its relaxed state and in the bended area there is an evident risk of damage or breaking of the penile implant. See e.g. U.S. Pat. No. 4,424,807 which shows a penile implant subjected to bending in its relaxed state.

One further problem often encountered with previously known penile implants is that the angle of the penis when activated by the penile implant is unnatural and does not correspond to the angle of an erected normally functioning penis. A normally functioning penis is bent upward to some extent, there are of course individual variations, when erected but previously known penile implants often result in an erected penis that is not bent upwards but solely stands straight out from the body under an angle of approximately 90 degrees. See e.g. U.S. Pat. No. 4,424,807 which shows a previously known penile implant as described.

Another problem often encountered with previously known implants, especially in connection with penile implants, is that a quite large amount of hydraulic fluid is needed to fill the implant when the implant is activated. This leads to a delay in the activation of the implant and to a relatively large reservoir for the hydraulic fluid. The larger the reservoir for the hydraulic fluid is, the more difficult it is to invasively place it in the body, e.g. in the scrotum, and potentially the more inconvenient it is for the patient to have the reservoir invasively placed in the body. To have a large amount of hydraulic fluid in the activated penile implant also makes the penile implant heavy which may be dissuitable. See e.g. U.S. Pat. No. 4,424,807 which shows a previously known penile implant as described. To have a large amount of hydraulic fluid in an activated adjustable implant also makes the implant unnecessarily heavy, which may be disadvantageous. See e.g. U.S. Pat. No. 4,424,807 or U.S. Pat. No. 6,875,233 B1 which show previously known implants as described.

Another problem often encountered with previously known penile implants is that there is no radial or longitudinal expansion of the penile implant when filled with hydraulic fluid. In contrast, a natural corpus cavernosum undergoes a radial and longitudinal expansion when filled with blood. There is previously known penile implants having provisions for radial and longitudinal expansion, see e.g. U.S. Pat. No. 4,424,807, but these provisions have less favorable characteristics in certain aspects. In the case of U.S. Pat. No. 4,424,807, as mentioned before, the folded or overlapped portions 50 and the folded ends 44 and 46 may be prone to be bridged or covered by fibrotic tissue. A further problem with previously known implants is that they do not provide any remedy for dysfunctional ejaculation.

Also other solutions than those cited above are known in this field, one known solution to achieve erection is to restrict the blood flow leaving the penis. For example, U.S. Pat. No. 4,828,990 discloses two hydraulically operated inflatable cuffs wrapped around respective crura or veins. A disadvantage of such a solution is that it involves complicated surgery.

Another known solution according to U.S. Pat. No. 4,828,544 comprises an artificial fistula system surgically implanted and providing a primary fistula between the femoral artery and the femoral vein and a secondary fistula for leading blood from the the primary fistula to the penis. An inflatable balloon engages the primary fistula between the secondary fistula and the vein. The balloon is in fluid connection with a manually compressible reservoir implanted in the scrotum. Again, implantation of this artifical fistula system requires delicate surgery. Another disadvantage, to such a solution, is the fact that the venous blood vessel system is rather complex and it is difficult to restrict the vein plexa.

Yet another known solution, for example disclosed in U.S. Pat. Nos. 3,855,122, 3,954,102, 4,009,711, 4,201,202, 4,235,222, 4,318,396, 5,250,020 and 4,424,807, currently practised is to replace the corpus cavernosa in the penis with a hydraulic inflatable/contractable silicone prosthesis thus implanted in the penis. In fluid connection with this prosthesis is a balloon-like reservoir implanted in the scrotum. By manual pumping action the prosthesis is filled with fluid from the reservoir to effect errect penile condition or is emptied of fluid, which returns to the reservoir, to effect flaccid penile condition.

Another problem often encountered with previously known implants is that they are not adjustable in size in a convenient or satisfactory way.

It is an aim to provide a technique that leads to improvement regarding all or at least some of the areas or aspects discussed above.

SUMMARY

According to one aspect of the invention there is provided a surface structure for an implant, e.g. an adjustable implant, and an implantable device or implant having such a surface structure. The surface structure has defined distances between the elements of the structure. The distances are big enough to prevent or limit fibrotic tissue from bridging the elements or connecting the elements in such a way as to impede the function of the implant.

According to one aspect of the invention there is provided a surface structure for an penile implant, especially an elongated penile implant or penile prosthesis for curing erectile impotence, and an implantable device having such a surface structure, where the surface structure has defined distances between the elements of the structure. The distances are big enough to prevent or limit fibrotic tissue from bridging the elements or connecting the elements in such a way as to impede the function of the implant.

Fibrotic tissue can often have an extension or thickness of about 0.5 mm to about 1.5 mm and hence the distances between relevant surfaces of the elements of the surface structure are suitably greater than about 3 mm, hence greater than about 2×1.5 mm. But depending on the circumstances also distances greater than about 1.0 mm to about 3 mm may be sufficient. In cases where the fibrotic tissue can be expected to have an extension or thickness greater than about 1.5 mm the distances between relevant surfaces of the elements of the surface structure arc adapted in a suitable manner.

The surface structure may comprise elevated and lowered areas and it may be suitable that also a distance between the different planes of the elevated and lowered areas is bigger than a certain threshold to facilitate the collapsible and/or expandable functionality of the implant. If said distance is too small, the collapsible and/or expandable functionality of the implant may be limited. A suitable interval for said distance is around 0.5 to 10 mm, more suitable around 2-8 mm and most suitable around 3-7 mm The surface structure may comprise different geometrical elements or shapes and any combination of such elements or shapes as long as the above mentioned conditions for the distances can be met. The surface structure may e.g. comprise ridges and grooves of different shapes. The ridges and grooves may each have a cross-section that is e.g. wedge-shaped, polygonal, square-formed, pyramidal-shaped, truncated pyramidal-shaped or. Further may the ridges and grooves have cross-sections of different shape. The surface structure may as well in general comprise a bellows-shaped structure or a surface structure where geometrical objects of the same or different kind(s) are placed on a surface. The geometrical objects may be practically randomly placed on the surface or according to some scheme.

One type of implants where this type of surface structure is suitable, is implants where the implant should have the ability to change shape and/or size substantially, e.g. penile implants. Hence, this is a case where the presence of fibrotic tissue substantially could hinder or impede the function of the implant. But the surface structure may be used by any implant where the characteristics of the surface structure would be suitable for the implant.

According to another aspect of the invention there is provided an implant or implantable device e.g a penile implant or penile implantable device, in particular an elongated penile implant or penile prosthesis for curing erectile impotence, having a pre-formed section. The pre-formed section may suitably comprise a surface shape having at least one fold, pleat or bellow shaped part or part having a smooth surface, or combinations thereof. This to mention some examples. The pre-formed section is suitably in a position or area where the penile implant often is bent. For a penile implant one suitable position for the pre-formed section is a point or area of the penile implant which is in the vicinity of and/or including the position where the protruding part of the penis starts. With the protruding part of the penis it is meant the part of the penis that is visible on the outside of the body, also called pendulous part. Suitably the pre-formed section is shaped in a way as to give the penile implant a shape that corresponds to or resembles the shape that the penile implant has most of the time. This may be suitable to minimize the stress on the material of the implant. In the case of a penile implant it can e.g. be assumed that the penile implant is relaxed most of the time. Hence, it is suitable that the pre-formed section is shaped in a way as to give the penile implant a shape that corresponds to or resembles the shape of a relaxed penis. The pre-formed section suitably has a certain extension in the longitudinal direction of the penile implant, here called longitudinal extension. The longitudinal extension of the pre-formed section is suitably in the interval of around 5-150 mm, depending on the circumstances, e.g. the length of the penile implant. It may be suitable that the pre-formed section has a longitudinal extension that is around 10-40 percent of the total longitudinal extension of the penile implant. The pre-formed section may comprise a substantially saw tooth shaped surface, or any other suitable surface shape which enables an appropriate function of the pre-formed section, e.g. any of the surface shapes or elements described in the section of this application regarding the surface structure having elevated and lowered areas. The surface shape(s) of the pre-formed section may extend along a part of, parts of or the complete circumference of the pre-formed section. In the case of a substantially saw tooth shaped surface, or any other surface shape comprising ridges and grooves, e.g. a square wave shaped surface or a wave shaped surface, it is suitable that the ridges and grooves extend in a substantially circumferential direction of the penile implant and that the ridges and grooves are placed alternating one after the other in a substantially longitudinal direction of the implant. By providing an implant, in particular a penile implant, with a pre-formed section as described, the risk for breaking of, or damage to, the penile implant is reduced and may even be substantially eliminated.

According to another aspect of the invention there is provided an penile implant or penile implantable device, in particular an elongated penile implant or penile prosthesis for curing erectile impotence, comprising bending portion giving the penile implant a desired angle when activated, e.g. filled with hydraulic fluid. For a penile implant said bending portion gives the activated penile implant an upwardly bent position. That is, when said penile implant is invasively placed in the corpus cavernosum, suitably one penile implant in each corpus cavernosum, in the penis of a standing person, frequently a man, and activated, said implant, and hence also the penis, assumes an upwardly bent position. With upwardly bent is meant that the penis has an acute angle with a vertical plane, said angle being measured from the upper side of the penis towards a vertical plane when said person is standing. Suitably said vertical plane is substantially parallel with the body of said standing person. Said bending portion may e.g. comprise that the penile implant has a bellows structure and/or a pliable wall part at least in the area where the penile implant is bent, or should be able to be bent. Further, the bending portion, e.g. a bellows structure or a pliable wall part, on one side of the penile implant is designed to show a greater length expansion when the penile implant is activated than the bending portion on the other side of the implant. Said bending portion may e.g. be positioned at a point or in an area of the penile implant which is in the vicinity of and/or including the position where the protruding part of the penis starts. The bending portion that should show a greater length expansion when the penile implant is activated may e.g. have a greater area. This may e.g. be achieved in that the bending portion has a greater longitudinal extension on one side of the penile implant than on the other side. Another possibility is that, in case of a bellows structure, the bellows structure has a greater depth, at least when the penile implant is in- or non-activated, on one side of the penile implant than on the other side, to enable a greater length expansion of the bellows structure having the greater depth. These two possibilities may of course also be combined. In the A bellows structure often has a surface structure which can be said to comprise ridges and grooves. For measuring the depth of a bellows structure one may measure the distance between the bottom of a groove and the top of a ridge. With length expansion is meant an expansion in the longitudinal direction of the implant, with longitudinal extension it is meant an extension in the longitudinal direction of the implant. Said device suitably comprises a relatively short proximal portion, which is to be anchored in the root of the penis, or placed in the part of the corpus cavernosum that is located inside the body, and a flexible relatively long, distal portion. Said distal portion suitably extends along the pendulous part of the penis, wherein said bending portion is positioned at or on said proximal portion, suitably in the vicinity of the position where said proximal portion and said distal portion meet. Suitably the distal portion is longer than the proximal portion, as is indicated by the expressions "relatively short proximal portion" and "relatively long, distal portion". The longitudinal extension of the bending portion is suitably in the interval of around 5-150 mm, depending on the circumstances, e.g. the length of the penile implant. It may be suitable that the bending portion has a longitudinal extension that is around 10 to 40 percent of the total longitudinal extension of the penile implant. The depth of the bellows structure is suitably in the interval of around 0.5 to 5 mm, even more suitable around 1-4 mm and most suitably around 1.5-3 mm, depending on the circumstances, e.g. the desired angle of the penis when the penile implant is activated.

The bending portion may comprise a substantially saw tooth shaped surface, or any other suitable surface shape which enables an appropriate function of the bending portion, e.g. any of the surface shapes or elements described in the section of this application regarding the surface structure having elevated and lowered areas. The surface shape(s) of the bending portion may extend along a part of, parts of, or the complete, circumference of the bending portion. In the case of a substantially saw tooth shaped surface, or any other surface shape comprising ridges and grooves, e.g. a square wave shaped surface or a wave shaped surface, it is suitable that the ridges and grooves extend in a substantially circumferential direction of the penile implant and that the ridges and grooves are placed alternating one after the other in a substantially longitudinal direction of the implant. Evidently, to achieve the desired effect the penile implant should be invasively placed in the corpus cavernosum so that the bellows structure designed to show the greater length expansion when the penile implant is activated, is on the underside of the penile implant. It is also possible that the bellows structure covers a part, or parts, of the circumference of the implant. The bellows structure may e.g. substantially only cover the underside of the implant, or it may substantially cover the underside and the upper side but not the sides of the implant. The reference for the expressions "underside" and "upper side" is the situation that the penile implant is placed in the corpus cavernosum of a standing person, frequently but not necessarily exclusively, a standing man in the case of a penile implant. One advantage with said bending portion is that the penis will have a natural angle when the penile implant is activated. This is an advantage e.g. since it is more comfortable for the patient when the penis has a natural appearance in its erected state and since sexual intercourse can be performed in a more natural way.

According to a further aspect of the invention there is provided an implant or implantable device, e.g. an adjustable implant or implantable device, e.g. an penile implant or penile implantable device, in particular an elongated penile implant or penile prosthesis for curing erectile impotence, where the implant comprises a hollow part comprising a foam or a similar material, hereafter called foam material. The hollow part may e.g. be implemented in that the implant itself is hollow or comprises a hollow body. The hollow part can be filled with a transportable medium to activate the implant. The transportable medium may e.g. be a fluid such as a gas or a liquid. Suitably the foam material is transparent for or to fluid and occupies at least part of the volume defined by the hollow part. Transparent for or to fluid means that the foam material comprises or defines open spaces that can be filled with fluid. In this way the amount of transportable medium that is needed to fill the hollow part is reduced as compared to the case where the hollow part has to be completely filled with the transportable medium. This is an advantage e.g. since the weight of the implant when activated is reduced and the hollow part can be filled with transportable medium more quickly. This is suitable for the patient having the implant implanted. To further reduce the weight of the implant when activated, the foam material may comprise a closed cellular foam material comprising closed spaces containing a, suitably low density, solid material, gas or fluid, e.g. air or foam material.

Foam materials of the closed cellular type have pores or cells that are not interconnected and are sealed off to an external surface. Hence, the inside of the closed spaces do not come in contact with the transportable medium. Suitably the foam material comprises a flexible foam material.

According to yet another aspect of the invention there is provided an implant or implantable device, e.g. an adjustable implant or implantable device, e.g an penile implant or penile implantable device, in particular an elongated penile implant or penile prosthesis for curing erectile impotence, where the implant is adjustable in size between a collapsed state and an expanded state. Suitably the implant comprises at least one expandable portion. The implant may also be adjustable in size between a collapsed state and one or more expanded states. In the expanded states the implant may be fully or partly expanded.

To achieve that the implant can have the desired flexibility, consistence, rigidity or stiffness for the application at hand, e.g. a breast or penile implant, also when the implant is in a partly expanded state, the expandable portion may be designed or adapted to present the necessary stiffness already when the expandable portion is partly expanded, and to achieve that the penile implant has the required stiffness to make the penis erect and hard also when the penile implant is in a partly expanded state, the expandable portion suitably is designed or adapted to present the necessary stiffness already when the expandable portion is partly expanded. This may be achieved by designing the expandable portion so that it presents an appropriate resistance against further expansion already when the expandable portion is partly expanded. The higher resistance an object presents against expansion, the greater the stiffness of the object is. The material and/or the surface structure of the expandable portion may e.g. have the characteristic that it from a certain degree of expansion has the required stiffness and may be further expanded up to full expansion while maintaining the same, or substantially the same, stiffness. Another way of achieving the characteristic that the implant has the required stiffness to make e.g. the penis erect and hard also when the implant is in a partly expanded state will now be described. It is assumed that the penile implant comprises a hollow part adapted to be filled with a fluid, the hollow part may be realized in that the penile implant itself is hollow or it may comprise a hollow body. The hollow part is divided in compartments separated by dividing wall(s) having a valve which at a first side opens for fluid flow from the first side when the fluid pressure at the first side exceeds a certain pressure value but otherwise is closed for fluid flow from the first side. At the second side of the valve the valve opens for fluid flow from the second side already when the fluid pressure at the second side is very low, suitably at substantially zero pressure. This to enable emptying the compartment on the second side and collapsing an invagination, the compartment on the second side of the wall has at least one invagination. In this way a first compartment on the first side of a dividing wall can be filled and pressurized with fluid to make the implant hard and stiff at a first size, and by further increasing the pressure of the fluid a second compartment on the second side of a dividing wall can be filled and pressurized with fluid to make the implant hard and stiff at a second, greater size when the invagination bulge due to the fluid pressure. Suitably the first compartment is adapted to always be filled and pressurized with fluid when the implant is activated. Of course more than two compartments may be used where dividing walls separate the different compartments and where the valves in the different dividing walls have increasing pressure thresholds starting with a first valve in a first dividing valve between the first and the second compartment having the lowest threshold. In this way it can be achieved that when such an implant is implanted in the corpus cavernosum, suitably one implant in each corpus cavernosum, the implant(s) can be activated in steps to make the penis erect and hard at several different sizes of the penis, both regarding diameter and length.

The invagination of the second compartment may also e.g. be a bending portion which makes it possible to selectively activate, or to different degrees activate, the bending portion. There may also be several such bending portions located around the circumference of the penile implant, this makes it possible to selectively activate different bending portions to achieve an erected penis that is bent not only upwards but also to either side or downwards, if this should be desired.

With an implant of any of the designs described above, it is as said possible to achieve that the implant can be activated to reach a desired degree of flexibility, rigidity or stiffness at different sizes of the implant, e.g. at sizes from 60% to 100% or from 80% to 100% of the maximum size of the implant.

In the case of a organ implant it may comprise a radially expandable portion and/or a longitudinally expandable portion to enable an enlargement and/or an elongation or extension of the organ when the implant is placed in the and activated and/or expanded. Said sections may each comprise a bellows structure, respectively a radial and a longitudinal bellows structure. Said expandable portions may have different surface structures and/or cross sections.

In the case of a breast implant it may comprise . . . .

In general, the expandable portions may comprise any suitable surface shape which enables an appropriate function of the section(s), e.g. any of the surface shapes or elements described in the section of this application regarding the surface structure having elevated and lowered areas.

The radially expandable portion is suitably located on the part of the implant that is adapted to be placed in the protruding or pendulous part of the organ. The longitudinally expandable portion may be located on the part of the implant that is adapted to be placed in the part of the organ that substantially extends on the inside of the body, also called the root of the organ, and/or on the part of the implant that is adapted to be placed in the protruding or pendulous part of the organ. The implant may suitably comprise a relatively short proximal portion and a flexible relatively long distal portion. Suitably the proximal portion is to be anchored or located in the root of the organ and the distal portion is to be located in or to extend along the pendulous part of the organ. The radially and the longitudinally expandable portion may also be located to partly overlap each other. Both sections may e.g. be located on the distal portion, the longitudinally expandable portion suitably on the part of the distal portion which is in the vicinity of the position where the proximal and distal portion meet, and the radially expandable portion suitably extend along substantially the whole distal portion. Depending on the desired shape of the organ when the implant is in an expanded state the radially expandable portion may also extend along only a part of the distal portion. The part of the implant that is adapted to be placed in the vicinity of or at the position of the glans organ may e.g. have no radially expandable portion or a radially expandable portion with smaller or greater possible radial expansion than the rest of the radially expandable portion.

The longitudinal extension of the longitudinally expandable portion when the implant is in its collapsed state is suitably in the interval of around 5-100 mm, depending on the circumstances, e.g. the desired possible prolongation or extension when the implant is expanded and the length of the implant in its collapsed state. It may be suitable that the longitudinally expandable portion has a longitudinal extension that is around 10 to 40 percent of the total longitudinal extension of the implant. The depth of the bellows structure of the longitudinally expandable portion when the implant is in its collapsed state is suitably in the interval of around 0.5 to 5 mm, even more suitable around 1-4 mm and most suitably around 1.5-3 mm, depending on the circumstances, e.g. the desired possible prolongation or extension when the implant is expanded and the length of the implant. For measuring the depth of a bellows structure one may measure the distance between the bottom of a groove and the top of a ridge.

The longitudinal extension of the radially expandable portion has been discussed above. When the implant is in its collapsed state a suitable interval for the longitudinal extension of the radially expandable portion is around 5-250 mm, depending on the circumstances, e.g. the length of the distal part of the implant in its collapsed state. It may be suitable that the radially expandable portion has a longitudinal extension that is around 80 to 100 percent of the total longitudinal extension of the distal part of the implant. The total depth or extension of the concavenesses or indentations of the radially expandable portion when the implant is in its collapsed state is suitably in the interval of around 5 to 70 mm, depending on the circumstances, e.g. the desired diameter of the implant in the collapsed state and in an expanded state. It may be suitable that the total depth or extension of the concavenesses or indentations of the radially expandable portion is around 40 to 60 percent of the circumference of the implant in its collapsed state when not including the extension of the concavenesses or indentations when calculating the circumference.

Suitably the implant or implantable device comprises at least one hollow section or hollow body in all of the described aspects. The at least one hollow section or hollow body may be expandable and/or collapsible and may extend along the whole length, or part of the length, of the implantable device.

The implantable device may also comprise a transportable medium adapted to be received into the at least one hollow section or hollow body, or to be withdrawn from the at least one hollow section or hollow body, in order to activate respectively inactivate the implantable device.

The at least one hollow section or hollow body may suitably be adapted to receive the transportable medium, and adapted so that the transportable medium can be withdrawn from the hollow section or hollow body, in order to activate respectively inactivate the implantable device.

The implantable device may be placed in the by any suitable known technique, e.g. by surgically forming a passageway in the and then placing or locating the implantable device in the passageway.

According to yet a further aspect of the invention there is provided a organ prosthesis system for curing erectile impotence where the system comprises at least one implant or implantable device as described herein. Suitably the system comprises two implants or implantable devices. Such a system suitably includes an operation device connected, suitably by a conduit, to the at least one implantable device. The operation device may comprise a fluid reservoir and a pump both connected to the at least one implantable device by a conduit so that fluid can be pumped to and from the implantable device(s). The pump may be manually operated or powered by an energy source. The system may as well comprise a control device connected to the operation device, suitably to the pump but it may as well be connected to the fluid reservoir. The control device may transmit control signals and/or powering signals to the pump and/or the fluid reservoir.

In the text describing the system, e.g. a organ prosthesis system, it is stated that different parts is or are for operating or regulating the implant or implantable device. This implies e.g. that these different parts are adapted to fill and pressurize the implantable device and mentioned parts of the implantable device with a transportable medium, e.g. a fluid. This implies e.g. also that these different parts are adapted to withdraw a transportable medium, e.g. a fluid, from the implantable device and mentioned parts of the implantable device. Mentioned parts of the implantable device are e.g. the expandable section, the pre-formed section, the bending portion, the radially expandable portion, the longitudinally expandable portion, the first and second compartments, the first and second hollow portions and the hollow body.

According to yet another aspect of the invention there is provided a method for invasively placing said implantable device in the of a organ.

As mentioned, said implantable device may suitably be an implant or organ prosthesis for curing erectile impotence and adapted to be implanted in the of a organ.

With a penile implant of any of the designs described above, it is as said possible to achieve that the penile implant, or implants since normally one penile implant is placed in each corpus cavernosum, can be activated to make the penis erect and hard at different sizes of the penis, e.g. at sizes from 60% to 100% or from 80% to 100% of the maximum size of the penis. The maximum size of the penis corresponds to the state when the at least one implant, placed in the corpus cavernosum of the penis, is fully expanded.

Generally, suitably the penile implant comprises a radially expandable portion and/or a longitudinally expandable portion to enable an enlargement and/or an elongation or extension of the penis when the penile implant is placed in the corpus cavernosum and activated and/or expanded. Said sections may each comprise a bellows structure, respectively a radial and a longitudinal bellows structure. Said expandable portions may have different surface structures and/or cross sections.

The radially expandable portion may e.g. be realized or implemented by designing the penile implant with a waist so that the cross section of the penile implant comprises two concavenesses or indentations which may be located substantially opposite each other. The implant, and hence also the cross section of the implant, may also comprise more than two concavenesses or indentations, e.g. four concavenesses or indentations, which may be located substantially equally spaced around the circumference of the implant. The penile implant may also comprise one concaveness or indentation where it is suitable that the penile implant is placed in the corpus cavernosum so that the opening of the concaveness or indentation faces, or substantially faces, the urethra. The at least one concaveness or indentation may e.g. be substantially U-shaped or V-shaped in cross section and suitably has a rounded shape without sharp edges. Hence, the radial bellows structure comprises the mentioned waist and/or concaveness(es) or indentation(s).

The longitudinally expandable portion may comprise a longitudinal bellows structure having a substantially saw tooth shaped surface. The ridges and grooves of the longitudinal bellows structure also may have a substantially square shape so that the longitudinal bellows structure comprises a square wave shaped surface. The ridges and grooves of the longitudinal bellows structure may also be rounded to different degrees so that the longitudinal bellows structure comprises a more or less wave shaped surface. The surface shape(s) of the longitudinally expandable portion may extend along a part of, parts of, or the complete, circumference of the implant. In the case of a surface shape comprising ridges and grooves, it is suitable that the ridges and grooves extend in a substantially circumferential direction of the penile implant and that the ridges and grooves are placed alternating one after the other in a substantially longitudinal direction of the implant.

In general, both the radially expandable portion and the longitudinally expandable portion may comprise any suitable surface shape which enables an appropriate function of the section(s), e.g. any of the surface shapes or elements described in the section of this application regarding the surface structure having elevated and lowered areas.

The radially expandable portion is suitably located on the part of the penile implant that is adapted to be placed in the protruding or pendulous part of the penis. The longitudinally expandable portion may be located on the part of the penile implant that is adapted to be placed in the part of the penis that substantially extends on the inside of the body, also called the root of the penis, and/or on the part of the penile implant that is adapted to be placed in the protruding or pendulous part of the penis. The penile implant may suitably comprise a relatively short proximal portion and a flexible relatively long distal portion. Suitably the proximal portion is to be anchored or located in the root of the penis and the distal portion is to be located in or to extend along the pendulous part of the penis. The radially and the longitudinally expandable portion may also be located to partly overlap each other. Both sections may e.g. be located on the distal portion, the longitudinally expandable portion suitably on the part of the distal portion which is in the vicinity of the position where the proximal and distal portion meet, and the radially expandable portion suitably extend along substantially the whole distal portion. Depending on the desired shape of the penis when the penile implant is in an expanded state the radially expandable portion may also extend along only a part of the distal portion. The part of the penile implant that is adapted to be placed in the vicinity of or at the position of the glans penis may e.g. have no radially expandable portion or a radially expandable portion with smaller or greater possible radial expansion than the rest of the radially expandable portion.

The longitudinal extension of the longitudinally expandable portion when the penile implant is in its collapsed state is suitably in the interval of around 5-100 mm, depending on the circumstances, e.g. the desired possible prolongation or extension when the penile implant is expanded and the length of the penile implant in its collapsed state. It may be suitable that the longitudinally expandable portion has a longitudinal extension that is around 10 to 40 percent of the total longitudinal extension of the penile implant. The depth of the bellows structure of the longitudinally expandable portion when the penile implant is in its collapsed state is suitably in the interval of around 0.5 to 5 mm, even more suitable around 1-4 mm and most suitably around 1.5-3 mm, depending on the circumstances, e.g. the desired possible prolongation or extension when the penile implant is expanded and the length of the penile implant. For measuring the depth of a bellows structure one may measure the distance between the bottom of a groove and the top of a ridge.

The longitudinal extension of the radially expandable portion has been discussed above. When the penile implant is in its collapsed state a suitable interval for the longitudinal extension of the radially expandable portion is around 5-250 mm, depending on the circumstances, e.g. the length of the distal part of the penile implant in its collapsed state. It may be suitable that the radially expandable portion has a longitudinal extension that is around 80 to 100 percent of the total longitudinal extension of the distal part of the penile implant. The total depth or extension of the concavenesses or indentations of the radially expandable portion when the penile implant is in its collapsed state is suitably in the interval of around 5 to 70 mm, depending on the circumstances, e.g. the desired diameter of the penile implant in the collapsed state and in an expanded state. It may be suitable that the total depth or extension of the concavenesses or indentations of the radially expandable portion is around 40 to 60 percent of the circumference of the penile implant in its collapsed state when not including the extension of the concavenesses or indentations when calculating the circumference.

According to yet another aspect of the invention there is provided an implantable vibration device adapted to improve or remedy dysfunctional ejaculation. Suitably the vibration device is adapted to be implanted in the genital area, e.g. in the corpus cavernosum of a penis of a person or in a penile implant for curing erectile impotence or in a penile prosthesis system for curing erectile impotence. The vibration device is located so as to cause a vibration to improve or remedy dysfunctional ejaculation.

The vibration device may fully or partly remedy dysfunctional ejaculation. If the vibration device is located in a penile implant or penile prosthesis system for curing erectile impotence, which is filled with a transportable medium, e.g. a fluid, the vibration device may be placed in the transportable medium. In this way the vibrations from the vibration device can be conveyed from the vibration device to the penile implant or penile prosthesis system via the transportable medium. In this case the vibration device may be placed either in the penile implant or in an element containing transportable medium and being connected to the penile implant. Such an element may e.g. be a reservoir, a conduit or a pump. Hence, there is also provided a penile implant and a penile prosthesis system comprising a vibration device. Generally the vibration device is adapted and located so as to stimulate at least a part of the sexually responsive tissue of the penis of the patient or person.

The vibration device may be of any suitable known type, e.g. a motor having an eccentric element eccentrically mounted to its axis, a vibration device of the magnetic type using magnetic repulsion and/or attraction, a piezoelectric device or a vibration device having a reciprocating piston. Suitably the vibration device is adapted to create movement with a frequency of around 0.1 to 10 000 Hz, and to create movement with an amplitude of around 0.01 to 30 mm.

Suitably the penile implant or implantable device comprises at least one hollow section or hollow body in all of the described aspects. The at least one hollow section or hollow body may be expandable and/or collapsible and may extend along the whole length, or part of the length, of the implantable device.

The implantable device may also comprise a transportable medium adapted to be received into the at least one hollow section or hollow body, or to be withdrawn from the at least one hollow section or hollow body, in order to activate respectively inactivate the implantable device.

The at least one hollow section or hollow body may suitably be adapted to receive the transportable medium, and adapted so that the transportable medium can be withdrawn from the hollow section or hollow body, in order to activate respectively inactivate the implantable device.

The implantable device may be placed in the corpus cavernosum by any suitable known technique, e.g. by surgically forming a passageway in the corpus cavernosum and then placing or locating the implantable device in the passageway.

According to yet a further aspect of the invention there is provided a penile prosthesis system for curing erectile impotence where the system comprises at least one penile implant or penile implantable device as described herein. Suitably the system comprises two penile implants or penile implantable devices. Such a system suitably includes an operation device connected, suitably by a conduit, to the at least one penile implantable device. The operation device may comprise a fluid reservoir and a pump both connected to the at least one penile implantable device by a conduit so that fluid can be pumped to and from the penile implantable device(s). The pump may be manually operated or powered by an energy source. The system may as well comprise a control device connected to the operation device, suitably to the pump but it may as well be connected to the fluid reservoir. The control device may transmit control signals and/or powering signals to the pump and/or the fluid reservoir.

In the text describing the system, e.g. a penile prosthesis system, it is stated that different parts is or are for operating or regulating the penile implant or penile implantable device. This implies e.g. that these different parts are adapted to fill and pressurize the penile implantable device and mentioned parts of the penile implantable device with a transportable medium, e.g. a fluid. This implies e.g. also that these different parts are adapted to withdraw a transportable medium, e.g. a fluid, from the penile implantable device and mentioned parts of the penile implantable device. Mentioned parts of the penile implantable device are e.g. the expandable section, the pre-formed section, the bending portion, the radially expandable portion, the longitudinally expandable portion, the first and second compartments, the first and second hollow portions and the hollow body.

According to yet another aspect of the invention there is provided a method for invasively placing said penile implantable device in the corpus cavemosum of a penis.

As mentioned, said penile implantable device may suitably be a penile implant or penile prosthesis for curing erectile impotence and adapted to be implanted in the corpus cavemosum of a penis.

The described aspects and features may be freely combined with another and thereby an implantable device or implantable vibration device having advantages from the combined aspects and features can be achieved. By combining the described aspects and features additional, synergistic effects can also be achieved. The described surface structure in its different embodiments may e.g. be used in any of the other aspects of the invention whereby additional advantages can be obtained. For example may the pre-formed section, the bending portion and the radially and longitudinally expandable portions comprise any of the elements, features and embodiments of the surface structure. Further may for example a penile implant comprise a pre-formed section and/or a bending portion and/or a radially and a longitudinally expandable portion. The implantable vibration device may as well be combined with the implantable device and the organ or penile prosthesis system.

The invention may also be described as in the following.

According to one aspect there is provided an implantable device. The implantable device may be adapted to post-operatively be adjustable and may comprise at least one expandable section. The implantable device may be adapted to be adjustable between a first collapsed state, in which the expandable section is collapsed, and a second expanded state, in which the expandable section is expanded.

The outer surface of said expandable section may at least partly comprise a surface structure having elevated areas alternating with lowered areas.

Said expandable section may be adapted to have, in at least one of said first collapsed and second expanded states, a first distance between adjacent elevated areas which distance is sufficiently extended to prevent growth of fibrotic tissue from directly interconnecting adjacent elevated areas to an extent that compromises the adjustability between a first collapsed and a second expanded state of said implantable device.

The surface structure may further comprise connecting areas between adjacent elevated and lowered areas. The connecting areas may further be adapted to have, in at least one of said first collapsed and second expanded states, a second distance between adjacent connecting areas which distance is sufficiently extended to prevent growth of fibrotic tissue from directly interconnecting adjacent connecting areas to an extent that compromises the adjustability between a first collapsed and a second expanded state of said implantable device.

The implantable device may optionally have the following further characteristics:

According to one embodiment there is provided an implantable device which is adapted to be non-invasively adjustable.

According to another embodiment there is provided an implantable device wherein at least said expandable section, is hollow or comprises a hollow body.

According to a further embodiment there is provided an implantable device wherein said implantable device is substantially completely hollow or comprises a hollow body extending along substantially the complete length of said implantable device.

According to yet another embodiment there is provided an implantable device wherein said implantable device comprises a transportable medium, e.g. a fluid. The transportable medium may be adapted to be received into and pressurize said expandable section and/or said implantable device and/or said hollow body, to bring said implantable device into said second expanded state. The transportable medium may further be adapted to be withdrawn from said expandable section and/or said implantable device and/or said hollow body, to bring said implantable device into said first collapsed state.

According to yet a further embodiment there is provided an implantable device wherein said expandable section and/or said implantable device and/or said hollow body, is adapted to receive, and be pressurized by, a fluid to bring said implantable device (10) into said second expanded state. Further may said expandable section and/or said implantable device and/or said hollow body be adapted to release said fluid, or adapted so that said fluid may be withdrawn therefrom, to bring said implantable device into said first collapsed state.

According to one embodiment there is provided an implantable device wherein said first respectively said second distance is adapted to fulfil said condition of preventing fibrotic tissue from directly connecting adjacent areas when said implantable device is in its first collapsed state.

According to another embodiment there is provided an implantable device wherein said first respectively said second distance is adapted to fulfil said condition of preventing fibrotic tissue from directly connecting adjacent areas, when said implantable device is in its second expanded state.

According to a further embodiment there is provided an implantable device wherein the outer surface of said expandable section is at least partly substantially bellows shaped or substantially corrugated.

According to yet another embodiment there is provided an implantable device wherein said implantable device, seen in cross section, comprises a waist portion.

According to yet a further embodiment there is provided an implantable device wherein the lowered areas lie in a plane substantially in parallel to a plane of the elevated areas.

According to one embodiment there is provided an implantable device wherein the outer surface of said expandable section at least partly comprises ridges and grooves.

According to another embodiment there is provided an implantable device wherein said ridges and grooves are substantially parallel.

According to a further embodiment there is provided an implantable device wherein the outer surface of said expandable section at least partly comprises protrusions and depressions.

According to yet another embodiment there is provided an implantable device wherein the top surfaces of the ridges and/or the bottom surfaces of the grooves at least partly have an extension greater than 1 mm in a direction transversal to the longitudinal direction of the ridges and/or grooves.

According to yet a further embodiment there is provided an implantable device wherein the distance between a plane of an elevated area and a plane of a lowered area is larger than 1 mm to facilitate achieving said first collapsed and/or said second expanded state.

According to one embodiment there is provided an implantable device wherein said expandable section is pre-formed into a shape substantially corresponding to the shape assumed by said implantable device in its first collapsed state.

According to another embodiment there is provided an implantable device wherein said alternating elevated areas and lowered areas are distributed over said outside surface of said implantable device so as to facilitate said implantable device assuming a specific shape when expanded.

According to a further embodiment there is provided an implantable device wherein said alternating elevated areas and lowered areas cover a larger part of one side of said implantable device, than of the opposite side of said implantable device.

According to another aspect there is provided an implantable device. Further may said implantable device be adapted to be post-operatively adjustable. Said implantable device may comprise a pre-formed section which is positioned at a point or in an area of said implantable device which is in the vicinity of and/or includes the position where a bent part of an organ is. Said preformed section is formed in such a way that bending creases are avoided or reduced when said implantable device is implanted and the organ is in a relaxed or flaccid position.

The implantable device may optionally have the following further characteristics:

According to one embodiment there is provided an implantable device wherein said pre-formed section comprises at least one fold, pleat, bellow shaped part or part having a smooth surface, or combinations thereof. Said pre-formed section may have a longitudinal extension in the interval of around 1 to 100 mm.

According to another embodiment there is provided an implantable device wherein said pre-formed section is expandable.

According to a further embodiment there is provided an implantable device which is adapted to be non-invasively adjustable.

According to yet another embodiment there is provided an implantable device wherein said implantable device is adapted to selectively assume a first in-activated state, in which said implantable device may be collapsed, and a second activated state, in which said implantable device may be expanded.

According to yet a further embodiment there is provided an implantable device wherein at least said pre-formed section is hollow or comprises a hollow body.

According to one embodiment there is provided an implantable device wherein said implantable device is substantially completely hollow or comprises a hollow body extending along substantially the complete length of said implantable device.

According to another embodiment there is provided an implantable device which may comprise a transportable medium, e.g. a fluid. The transportable medium is adapted to be received into and pressurize said pre-formed section and/or said implantable device and/or said hollow body, to bring said implantable device into said second activated state. The transportable medium may as well be adapted to be withdrawn from said pre-formed section and/or said implantable device and/or said hollow body, to bring said implantable device into said first in-activated state.

According to a further embodiment there is provided an implantable device wherein said pre-formed section and/or said implantable device and/or said hollow body, is adapted to receive, and be pressurized by, a fluid to bring said implantable device (10) into said second activated state. Further said pre-formed section and/or said implantable device and/or said hollow body may be adapted to release said fluid, or adapted so that said fluid may be withdrawn therefrom, to bring said implantable device into said first in-activated state.

According to a further aspect there is provided an implantable device. Further may said implantable device be adapted to be post-operatively adjustable and to be implanted in an organ.

Said implantable device may as well be adapted to selectively assume an in-activated state whereby said organ can be made flaccid, and an activated state whereby said organ can be erected or made erected.

Said implantable device may be collapsed in its in-activated state and expanded in its activated state.

Said implantable device may have a relatively short proximal portion which is suited to be placed or located in the root of the organ, and a flexible relatively long distal portion, which is suited to be placed so as to extend along or to be located in the pendulous or protruding part of the organ.

Said implantable device may further comprise a bending portion placed or located between the proximal and the distal portion, or in the vicinity of the position where the proximal and the distal portion meet.

Said bending portion may be adapted to enable said implantable device, when said implantable device is implanted and activated, to bring at least the pendulous or protruding portion of the organ to a position in which the organ has an acute angle with the vertical plane when said person is standing. That is, a position in which at least the pendulous or protruding portion of the organ is upwardly bent when said person is standing.

The implantable device may optionally have the following further characteristics:

According to one embodiment there is provided an implantable device wherein said bending portion may comprise a pliable or elastic wall part of said implantable device. Said wall part extends along a part of, along parts of, or along the complete, circumference of said implantable device. Said wall part extends in such a way as to, when said implantable device is implanted and activated, bring at least the pendulous part of the organ to a position in which the organ has an acute angle with the vertical plane when said person is standing.

According to another embodiment there is provided an implantable device wherein said wall part extends along at least a part of the underside, and along at least a part of the upper side of said implantable device. Said wall part has a greater longitudinal extension on the underside than on the upper side of said implantable device (10), when said implantable device (10) is activated and/or inactivated. This in order to, when said implantable device is implanted and activated, bring at least the pendulous part of the organ to a position in which the organ has an acute angle with the vertical plane when said person is standing.

According to a further embodiment there is provided an implantable device wherein said bending portion comprises a bellows structure which extends along a part of, along parts of, or along the complete, circumference of said implantable device. Said bellows structure is designed so that at least part of the underside of said implantable device shows a greater length expansion when said implantable device is activated than the upper side of said implantable device. This in order to, to, when said implantable device is implanted and activated, bring at least the pendulous part of the organ to a position in which the organ has an acute angle with the vertical plane when said person is standing.

According to yet another embodiment there is provided an implantable device wherein said bellows structure extends along at least a part of the underside, and along at least a part of the upper side of said implantable device.

Said bellows structure may have a greater longitudinal extension on the underside than on the upper side of said implantable device. Further may said bellows structure have a greater depth, at least when said implantable device is in it's in- or non-activated state, on the underside than on the upper side of said implantable device.

This in order to, when said implantable device is implanted and activated, bring at least the pendulous part of the organ to a position in which the organ has an acute angle with the vertical plane when said person is standing.

According to one embodiment there is provided an implantable device wherein said bending portion is positioned at a point or in an area of said implantable device which is in the vicinity of and/or including the position where the pendulous or protruding part of the organ starts.

According to another embodiment there is provided an implantable device wherein said bending portion is positioned at or on said proximal portion, suitably in the vicinity of the position where said proximal portion and said distal portion meet.

According to a further embodiment there is provided an implantable device which is adapted to be non-invasively adjustable.

According to yet another embodiment there is provided an implantable device wherein at least said bending portion is hollow or comprises a hollow body.

According to yet a further embodiment there is provided an implantable device which is substantially completely hollow or comprises a hollow body extending along substantially the complete length of said implantable device.

According to one embodiment there is provided an implantable device which comprises a transportable medium, e.g. a fluid. Said transportable medium is adapted to be received into and pressurize said bending portion and/or said implantable device and/or said hollow body in order to bring said implantable device into said second activated state. Said transportable medium may as well be adapted to be withdrawn from said bending portion and/or said implantable device and/or said hollow body, to bring said implantable device into said first in-activated state.

According to another embodiment there is provided an implantable device wherein said bending portion and/or said implantable device and/or said hollow body, is adapted to receive, and be pressurized by, a fluid to bring said implantable device into said second activated state. Further may said bending portion and/or said implantable device and/or said hollow body be adapted to release said fluid, or adapted so that said fluid may be withdrawn therefrom, to bring said implantable device into said first in-activated state.

According to a further embodiment there is provided an implantable device wherein said bending portion comprises that said proximal portion has a pliable top wall and a pliable bottom wall. Said bottom wall is designed to longitudinally distend more than said top wall, when said implantable device is brought into said second activated state by said transportable medium. This in order to cause said distal portion to bend upwardly in relation to said proximal portion.

According to yet another embodiment there is provided an implantable device wherein said bottom wall of said proximal portion forms circumferentially extending alternating ridges and grooves. Said bottom wall thereby behaves like an expanding bellows when said implantable device is brought into said second activated state by said transportable medium.

According to yet a further embodiment there is provided an implantable device wherein said ridges of said bottom wall are spaced apart from one another, when said implantable device is in its inactivated state.

According to one embodiment there is provided an implantable device wherein said top wall forms circumferentially extending alternating ridges and grooves. These ridges and grooves are dimensioned such that said top wall longitudinally distends less than said bottom wall, when said implantable device is brought into said second activated state by said transportable medium.

According to another embodiment there is provided an implantable device wherein said grooves are wedge-shaped.

According to a further embodiment there is provided an implantable device wherein said ridges have a polygonal cross-section.

According to yet another embodiment there is provided an implantable device wherein said distal portion of said implantable device comprises circumferentially extending alternating ridges and grooves. Thereby said distal portion behaves like an expanding bellows and longitudinally prolongs, when said implantable device is brought into said second activated state by said transportable medium.

According to yet a further embodiment there is provided an implantable device wherein said proximal portion of said implantable device is made of an elastic material.

According to one embodiment there is provided an implantable device wherein said top wall of said proximal portion is substantially thicker than said bottom wall of said proximal portion.

According to a further embodiment there is provided an implantable device wherein said elastic material comprises silicone elastomer.

According to yet another aspect there is provided an implantable device, . Said implantable device may be adapted to be implanted in the of a organ of a person. Said implantable device is at least partly hollow and/or at least partly comprises a hollow body. Said implantable device comprises a foam material transparent for fluid, said foam material is at least partly filling said implantable device and/or said hollow body.

Suitably said foam material has a lower density than water. Said implantable device and/or said hollow body is adapted to be filled with said foam material and said fluid so that said foam material and said fluid together substantially fill the volume of said implantable device and/or said hollow body.

The implantable device may optionally have the following further characteristics.

According to one embodiment there is provided an implantable device wherein said foam material comprises open spaces that can be filled with said fluid.

According to another embodiment there is provided an implantable device wherein said foam material is a closed cellular foam material which comprises closed spaces, suitably bubbles. The closed spaces may contain, or may be filled with, a solid material, a gas or a fluid, e.g. air or foam material.

According to a further embodiment there is provided an implantable device wherein said implantable device is adapted to be non-invasively adjustable.

According to yet another embodiment there is provided an implantable device, which is adapted to selectively assume a first in-activated state, wherein said implantable device may be collapsed, and a second activated state, wherein said implantable device may be expanded.

According to yet a further embodiment there is provided an implantable device wherein said fluid is adapted to be received into and pressurize said implantable device and/or said hollow body, to bring said implantable device into said second activated state. Said fluid may also be adapted to be withdrawn from said implantable device and/or said hollow body, to bring said implantable device into said first in-activated state.

According to one embodiment there is provided an implantable device wherein said implantable device and/or said hollow body, is adapted to receive, and be pressurized by, a fluid to bring said implantable device (10) into said second activated state. Said implantable device and/or said hollow body may also be adapted to release said fluid, or adapted so that said fluid may be withdrawn, to bring said implantable device into said first in-activated state.

According to yet a further aspect there is provided an implantable device, which may be an implantable device for curing erectile impotence. Said implantable device may be elongated and may be adapted to be implanted in the of a organ of a person. Said implantable device may also be adapted to post-operatively be adjustable.

Said implantable device may comprise at least one expandable portion and is adjustable between a first collapsed state and at least one other, partly or fully expanded, state. In the collapsed state the at least one expandable portion is collapsed, and in the other, partly or fully expanded, state said at least one expandable portion is partly or fully expanded.

Said at least one expandable portion may comprise at least one item chosen from the group consisting of; a radially expandable portion, a radially expandable segment, a longitudinally expandable portion, and a longitudinally expandable segment.

Said implantable device may have a predetermined shape with a length and a diameter and may be adapted to allow an increase of the implantable device diameter and/or length when being adjusted from said first collapsed to said at least one partly or fully expanded state. This in order to achieve increased organ size when said implantable device is implanted and partly or fully expanded, as compared to a relaxed status of the organ.

According to yet another aspect there is provided an implantable device, which may be an implantable device for curing erectile impotence. Said implantable device may be elongated and may be adapted to be implanted in the of a organ of a person. Said implantable device may be adapted to post-operatively be adjustable.

Said implantable device may comprise at least one expandable portion and may be adjustable between a first in-activated or collapsed state and at least one other, partly or fully expanded, activated state. In the first state said at least one expandable portion is collapsed and in the other, activated state, said at least one expandable portion is partly or fully expanded.

Said at least one expandable portion may comprise a radially expandable portion and/or a radially expandable segment at least partly comprising a cross section presenting at least one concaveness or indentation. Said cross section may present a concaveness or indentation facing the urethra of the organ.

Said implantable device may have a predetermined shape with a length and a diameter and may be adapted to allow an increase of the implantable device diameter when being adjusted from said first in-activated or collapsed state to said at least one other, partly or fully expanded, activated state. This in order to achieve increased organ size when said implantable device is implanted and partly or fully expanded, as compared to a relaxed status of the organ.

The implantable device may optionally have the following further characteristics.

According to one embodiment there is provided an implantable device wherein said radially expandable portion or said radially expandable segment at least partly comprises a cross section presenting at least one concaveness or indentation.

According to another embodiment there is provided an implantable device wherein said cross section presents at least two concavenesses or indentations.

According to a further embodiment there is provided an implantable device wherein said cross section presents a concaveness or indentation facing the urethra.

According to yet another embodiment there is provided an implantable device which comprises said radially expandable portion or said radially expandable segment on the part of said implantable device that is adapted to be placed in the protruding or pendulous part of the organ.

According to yet a further embodiment there is provided an implantable device wherein said at least one expandable portion comprises a longitudinally expandable portion or a longitudinally expandable segment. The longitudinally expandable portion or the longitudinally expandable segment may comprise a longitudinally expandable structure that comprises at least one concaveness or indentation.

According to one embodiment there is provided an implantable device wherein said at least one expandable portion comprises a longitudinally expandable portion or a longitudinally expandable segment. The longitudinally expandable portion or the longitudinally expandable segment may comprise a longitudinal bellows structure that comprises ridges and grooves that extend substantially circumferentially along a part of, along parts of, or along the complete, circumference of said implantable device.

According to another embodiment there is provided an implantable device wherein said longitudinally expandable portion or said longitudinally expandable segment is present on a proximal part of said implantable device. The proximal part may be adapted to be placed in the root part of the organ. The root part of the organ extends substantially on the inside of the body.

According to a further embodiment there is provided an implantable device wherein said longitudinally expandable portion or said longitudinally expandable segment is present on a distal part of said implantable device. Said distal part in suitably adapted to be placed in the protruding or pendulous part of the organ.

According to one embodiment there is provided an implantable device wherein;
the distance between the substantially opposing sides of the at least one concaveness or indentation,
and/or
the distance between the substantially opposing sides of the ridges and grooves of the longitudinal bellows structure,
is sufficiently extended to prevent growth of fibrotic tissue from directly interconnecting said substantially opposing sides to an extent that compromises the adjustability between a first collapsed state and at least one other, partly or fully expanded, state.

According to another embodiment there is provided an implantable device wherein;
the distance between the substantially opposing sides of the at least one concaveness or indentation,
and/or
the distance between the substantially opposing sides of the ridges and grooves of the longitudinal bellows structure,
is greater than around 1 mm, greater than around 2 mm, or greater than around 3 mm.

According to yet another embodiment there is provided an implantable device which is adapted to be non-invasively adjustable.

According to a further embodiment there is provided an implantable device wherein at least said at least one expandable portion is hollow or comprises a hollow body.

According to yet a further embodiment there is provided an implantable device wherein said implantable device is substantially completely hollow or comprises a hollow body extending along substantially the complete length of said implantable device.

According to one embodiment there is provided an implantable device wherein said implantable device comprises a transportable medium, e.g. a fluid. The transportable medium may be adapted to be received into and pressurize said at least one expandable portion and/or said implantable device and/or said hollow body. This in order to bring said implantable device into said at least one partly or fully expanded state. The transportable medium may also be adapted to be withdrawn from said at least one expandable portion and/or said implantable device and/or said hollow body, to bring said implantable device (10) into said first collapsed state.

According to another embodiment there is provided an implantable device wherein said at least one expandable portion and/or said implantable device and/or said hollow body, is adapted to receive, and to be pressurized by, a fluid. This in order to bring said implantable device into said at least one partly or fully expanded state. Said at least one expandable portion and/or said implantable device and/or said hollow body may also be adapted to release said fluid, or adapted so that said fluid may be withdrawn, to bring said implantable device into said first collapsed state.

According to a further embodiment there is provided an implantable device wherein said implantable device or said hollow body comprises a first and at least one second compartment both being adapted to be filled and pressurized with a fluid. The first and the at least one second compartment are separated by at least one dividing wall having at least one valve.

Said radially expandable segment and said longitudinally expandable segment may each comprise at least one of; a second compartment, a dividing wall having at least one valve, at least one invagination.

Said at least one second compartment comprises at least one invagination. Said at least one valve suitably has a first side or face which is adapted to be closed for fluid up to a predetermined fluid pressure threshold. For fluid pressures above said fluid pressure threshold said at least one valve is adapted to open. Said at least one valve suitably also has a second side or face which is adapted to be open for fluid at substantially any pressure, at least for a pressure greater than zero.

Said at least one invagination is adapted to bulge when subjected to fluid pressure and to resume its invaginated form when said fluid pressure is removed.

According to yet a further embodiment there is provided an implantable device wherein said first compartment is adapted to be connected to a source of pressurized fluid.

Said first side or face of said at least one valve is suitably facing said first compartment and said second side or face of said at least one valve is suitably facing said at least one second compartment. This is in order to enable that said at least one second compartment can be filled and pressurized with fluid when the fluid pressure in said first compartment exceeds said fluid pressure threshold so that said at least one invagination bulges and hence prolongs or radially expands said implantable device and/or hollow body.

According to yet another embodiment there is provided an implantable device wherein said implantable device or said hollow body comprises a longitudinally expandable portion having a first and a second hollow portion. The first and the second hollow portion are each adapted to be filled and pressurized with a fluid, they may be connected by an elastic first conduit, and optionally also by an elastic second conduit. The first and the second hollow portion may as well be connected by an elastic connecting portion.

At least one of, and suitably each of, said first and second hollow portions comprises at least one invagination. Said invagination is suitably adapted to bulge when subjected to fluid pressure and to resume its invaginated form when said fluid pressure is removed.

According to one embodiment there is provided an implantable device wherein each of said first and second hollow portions comprises an invagination. Said invaginations are suitably facing each other and are adapted to bulge and mutually exert a force on each other when subjected to fluid pressure. This in order to prolong said implantable device and/or hollow body when said first and second hollow portions are filled and pressurized with a fluid. Said invaginations are suitably adapted to resume their invaginated form when said fluid pressure is removed so that said implantable device and/or hollow body resumes its not prolonged length.

In another aspect there is provided a surgery method where an implantable device as described above is implanted in the patient.

In a further aspect there is provided a system that comprises an implantable device as described above.

In one embodiment the system comprises at least one switch implantable in the patient for manually and non-invasively controlling the implantable device.

In one embodiment the system comprises a hydraulic device having an implantable hydraulic reservoir, which is hydraulically connected to the implantable device, wherein the implantable device is adapted to be non-invasively regulated by manually pressing the hydraulic reservoir.

In one embodiment the system comprises a wireless remote control for non-invasively controlling the implantable device. The wireless remote control may comprise at least one external signal transmitter and/or receiver, further comprising an internal signal receiver and/or transmitter implantable in the patient for receiving signals transmitted by the external signal transmitter or transmitting signals to the external signal receiver.

In one embodiment the wireless remote control transmits at least one wireless control signal for controlling the implantable device.

In one embodiment the wireless control signal comprises a frequency, amplitude, or phase modulated signal or a combination thereof.

In one embodiment the wireless remote control transmits an electromagnetic carrier wave signal for carrying the control signal.

One embodiment comprises a wireless energy-transmission device for non-invasively energizing implantable energy consuming components of the implantable device with wireless energy.

In one embodiment there is provided a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. The signal may be an analogue signal, a digital signal, or a combination of an analogue and digital signal The wireless energy may be different in different embodiments, for example: an electric field, a magnetic field, or a combined electric and magnetic field.

The control signal may be different in different embodiments, for example an electric field, a magnetic field, or a combined electric and magnetic field.

In another embodiment there is provided an implantable internal energy source for powering implantable energy consuming components of the implantable device.

In one embodiment there is provided an external energy source for transferring energy in a wireless mode, wherein the internal energy source is chargeable by the energy transferred in the wireless mode.

In one embodiment there is provided a sensor or measuring device sensing or measuring a functional parameter correlated to the transfer of energy for charging the internal energy source, and a feedback device for sending feedback information from inside the patient's body to the outside thereof, the feedback information being related to the functional parameter sensed by the sensor or measured by the measuring device.

One embodiment further comprises a feedback device for sending feedback information from inside the patient's body to the outside thereof, the feedback information being related to at least one of a physical parameter of the patient and a functional parameter related to the implantable device.

In one embodiment there is provided a sensor and/or a measuring device and an implantable internal control unit for controlling the implantable device in response to information being related to at least one of a physical parameter of the patient sensed by the sensor or measured by the measuring device and a functional parameter related to the implantable device sensed by the sensor or measured by the measuring device. The physical parameter may be a pressure or a motility movement.

In one embodiment there is provided an external data communicator and an implantable internal data communicator communicating with the external data communicator, wherein the internal communicator feeds data related to the implantable device or the patient to the external data communicator and/or the external data communicator feeds data to the internal data communicator.

In one embodiment there is provided a motor or a pump for operating the implantable device.

In one embodiment there is provided a hydraulic operation device for operating the implantable device.

In one embodiment there is provided an operation device for operating the implantable device, wherein the operation device comprises a servo designed to decrease the force needed for the operation device to operate the implantable device instead the operation device acting a longer way, increasing the time for a determined action.

In one embodiment there is provided a operation device for operating the implantable device, wherein the wireless energy is used in its wireless state to directly power the operation device to create kinetic energy for the operation of the implantable device, as the wireless energy is being transmitted by the energy-transmission device.

In one embodiment there is provided an energy-transforming device for transforming the wireless energy transmitted by the energy-transmission device from a first form into a second form energy.

In one embodiment the energy-transforming device directly powers implantable energy consuming components of the implantable device with the second form energy, as the energy-transforming device transforms the first form energy transmitted by the energy-transmission device into the second form energy.

In one embodiment the second form energy comprises at least one of a direct current, pulsating direct current and an alternating current.

In one embodiment there is provided an implantable accumulator, wherein the second form energy is used at least partly to charge the accumulator.

In one embodiment the energy of the first or second form comprises at least one of magnetic energy, kinetic energy, sound energy, chemical energy, radiant energy, electromagnetic energy, photo energy, nuclear energy thermal energy, non-magnetic energy, non-kinetic energy, non-chemical energy, non-sonic energy, non-nuclear energy and non-thermal energy.

In one embodiment there are provided implantable electrical components including at least one voltage level guard and/or at least one constant current guard.

In one embodiment there is provided a control device for controlling the transmission of wireless energy from the energy-transmission device, and an implantable internal energy receiver for receiving the transmitted wireless energy, the internal energy receiver being connected to implantable energy consuming components of the implantable device for directly or indirectly supplying received energy thereto, the system further comprising a determination device adapted to determine an energy balance between the energy received by the internal energy receiver and the energy used for the implantable energy consuming components of the implantable device , wherein the control device controls the transmission of wireless energy from the external energy-transmission device, based on the energy balance determined by the determination device.

In one embodiment the determination device is adapted to detect a change in the energy balance, and the control device controls the transmission of wireless energy based on the detected energy balance change.

In one embodiment the determination device is adapted to detect a difference between energy received by the internal energy receiver and energy used for the implantable energy consuming components of the implantable device, and the control device controls the transmission of wireless energy based on the detected energy difference.

In one embodiment the energy-transmission device comprises a coil placed externally to the human body, further comprising an implantable energy receiver to be placed internally in the human body and an electric circuit connected to power the external coil with electrical pulses to transmit the wireless energy, the electrical pulses having leading and trailing edges, the electric circuit adapted to vary first time intervals between successive leading and trailing edges and/or second time intervals between successive trailing and leading edges of the electrical pulses to vary the power of the transmitted wireless energy, the energy receiver receiving the transmitted wireless energy having a varied power.

In one embodiment the electric circuit is adapted to deliver the electrical pulses to remain unchanged except varying the first and/or second time intervals.

In one embodiment the electric circuit has a time constant and is adapted to vary the first and second time intervals only in the range of the first time constant, so that when the lengths of the first and/or second time intervals are varied, the transmitted power over the coil is varied.

In one embodiment there is provided a system comprising an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off.

In one embodiment there is a an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils.

In one embodiment the transmitted energy may be regulated depending on the obtained coupling factor.

In one embodiment there is provided a system wherein the external second coil is adapted to be moved in relation to the internal first coil to establish the optimal placement of the second coil, in which the coupling factor is maximized.

In one embodiment there is provided a system wherein the external second coil is adapted to calibrate the amount of transferred energy to achieve the feedback information in the determination device, before the coupling factor is maximized.

In a yet further aspect there is provided an operation method using an implantable device or system according to the above further comprising the steps of: a) creating an opening in the skin or organ wall of the male patient, b) dissecting an one arca of the sexually responsive tissue, c) placing the implantable device within said area, adapted to postoperatively stimulate said sexually responsive tissue on patient command.

In one embodiment there is provided an operation method comprising the step of placing an operation device and a power source within the body.

In one embodiment the operation method comprises placing an implantable device comprising placing an integrated unit comprising the implantable device and an operation device in the same integrated unit.

In one embodiment the operation method comprises placing a power source comprising, placing an control unit and a rechargeable battery remote from said sexually responsive tissue.

In one embodiment the operation method comprises controlling said implantable device post-operatively and non-invasively from outside the body.

In one embodiment the operation method comprises the step of creating an opening in the skin or organ wall of the male patient comprising, a) inserting a tube or needle into the patients body, b) filling the tube or needle with a gas and thereby expanding a cavity within the male patients body, c) inserting at least two laparoscopic trocars into said cavity, d) inserting at least one camera trough at least one laparoscopic trocar, e) inserting at least one dissecting tool through at least one laparoscopic trocar.

In one embodiment the implantable device is adapted to be implanted in any, or each, of the of the organ of the male patient.

In one embodiment the implantable device is adapted to be implanted in the vicinity of, or in contact with, the glans organ of the organ of the male patient.

According to one embodiment there is provided a system comprising at least one implantable device. Said implantable device may be adapted to bring an organ to an erected or activated state, when said implantable device is implanted and activated or expanded.

Said implantable device is suitably adapted to bring a organ to a flaccid state, when said implantable device is implanted in the organ and in-activated or collapsed.

According to one aspect there is provided a method of implanting the implantable device in a person or patient.

According to a further aspect there is provided a method of implanting the system in a person or patient.

In a preferred embodiment, the system comprises at least one switch implantable in the patient for manually and non-invasively controlling the implant.

In another preferred embodiment, the system comprises a wireless remote control for non-invasively controlling the implant.

In a preferred embodiment, the system comprises a hydraulic operation device for operating the implant.

In one embodiment, the system comprises comprising a motor or a pump for operating the implant.

The implant or implantable device may be any adjustable implant adapted to change shape and/or size. The implant or implantable device may e.g. be an implant for treating urinal or anal incontinence, urin retention, obesity, reflux disease, an implant for patients having a stoma, an implant for implanted drug delivery, implantable potency treatment, a heart pump, an implant for aneurysm treatment, drainage treatment, fertility treatment, gastric cancer treatment, fluid lubrication methods.

The implant or implantable device may e.g. be a penile implant, a breast implant, a volume filling device, a bone adjustment implant, a heart pump, a vertical gastric band or an anal incontinence restriction device.

According to one aspect there is provided a penile implant, in particular a penile implant for curing erectile impotence. The penile implant may be adapted to be implanted in the corpus cavernosum of a penis, may be adapted to post-operatively be adjustable and may comprise at least one expandable section. The penile implant may be adapted to be adjustable between a first collapsed state, in which the expandable section is collapsed, and a second expanded state, in which the expandable section is expanded.

The outer surface of said expandable section may at least partly comprise a surface structure having elevated areas alternating with lowered areas.

Said expandable section may be adapted to have, in at least one of said first collapsed and second expanded states, a first distance between adjacent elevated areas which distance is sufficiently extended to prevent growth of fibrotic tissue from directly interconnecting adjacent elevated areas to an extent that compromises the adjustability between a first collapsed and a second expanded state of said penile implant.

The surface structure may further comprise connecting areas between adjacent elevated and lowered areas. The connecting areas may further be adapted to have, in at least one of said first collapsed and second expanded states, a second distance between adjacent connecting areas which distance is sufficiently extended to prevent growth of fibrotic tissue from directly interconnecting adjacent connecting areas to an extent that compromises the adjustability between a first collapsed and a second expanded state of said penile implant.

The penile implant may optionally have the following further characteristics:

According to one embodiment there is provided a penile implant which is adapted to be non-invasively adjustable.

According to another embodiment there is provided a penile implant wherein at least said expandable section, is hollow or comprises a hollow body.

According to a further embodiment there is provided a penile implant wherein said penile implant is substantially completely hollow or comprises a hollow body extending along substantially the complete length of said penile implant.

According to yet another embodiment there is provided a penile implant wherein said penile implant comprises a transportable medium, e.g. a fluid. The transportable medium may be adapted to be received into and pressurize said expandable section and/or said penile implant and/or said hollow body, to bring said penile implant into said second expanded state. The transportable medium may further be adapted to be withdrawn from said expandable section and/or said penile implant and/or said hollow body, to bring said penile implant into said first collapsed state.

According to yet a further embodiment there is provided a penile implant wherein said expandable section and/or said penile implant and/or said hollow body, is adapted to receive, and be pressurized by, a fluid to bring said penile implant (10) into said second expanded state. Further may said expandable section and/or said penile implant and/or said hollow body be adapted to release said fluid, or adapted so that said fluid may be withdrawn therefrom, to bring said penile implant into said first collapsed state.

According to one embodiment there is provided a penile implant wherein said first respectively said second distance is adapted to fulfil said condition of preventing fibrotic tissue from directly connecting adjacent areas when said penile implant is in its first collapsed state.

According to another embodiment there is provided a penile implant wherein said first respectively said second distance is adapted to fulfil said condition of preventing fibrotic tissue from directly connecting adjacent areas, when said penile implant is in its second expanded state.

According to a further embodiment there is provided a penile implant wherein the outer surface of said expandable section is at least partly substantially bellows shaped or substantially corrugated.

According to yet another embodiment there is provided a penile implant wherein said penile implant, seen in cross section, comprises a waist portion.

According to yet a further embodiment there is provided a penile implant wherein the lowered areas lie in a plane substantially in parallel to a plane of the elevated areas.

According to one embodiment there is provided a penile implant wherein the outer surface of said expandable section at least partly comprises ridges and grooves.

According to another embodiment there is provided a penile implant wherein said ridges and grooves are substantially parallel.

According to a further embodiment there is provided a penile implant wherein the outer surface of said expandable section at least partly comprises protrusions and depressions.

According to yet another embodiment there is provided a penile implant wherein the top surfaces of the ridges and/or the bottom surfaces of the grooves at least partly have an extension greater than 1 mm in a direction transversal to the longitudinal direction of the ridges and/or grooves.

According to yet a further embodiment there is provided a penile implant wherein the distance between a plane of an elevated area and a plane of a lowered area is larger than 1 mm to facilitate achieving said first collapsed and/or said second expanded state.

According to one embodiment there is provided a penile implant wherein said expandable section is preformed into a shape substantially corresponding to the shape assumed by said penile implant in its first collapsed state.

According to another embodiment there is provided a penile implant wherein said alternating elevated areas and lowered areas are distributed over said outside surface of said penile implant so as to facilitate said penile implant assuming a specific shape when expanded.

According to a further embodiment there is provided a penile implant wherein said alternating elevated areas and lowered areas cover a larger part of one side of said penile implant, than of the opposite side of said penile implant.

According to another aspect there is provided a penile implant, in particular a penile implant for curing erectile impotence, wherein said penile implant is adapted to be implanted in the corpus cavernosum of a penis. Further may said penile implant be adapted to be post-operatively adjustable. Said penile implant may comprise a pre-formed section which is positioned at a point or in an area of said penile implant which is in the vicinity of and/or includes the position where the protruding part of the penis starts. Said preformed section is formed in such a way that bending creases are avoided or reduced when said penile implant is implanted and the penis is in a relaxed or flaccid position, suitably hanging in a relaxed or flaccid position.

The penile implant may optionally have the following further characteristics:

According to one embodiment there is provided a penile implant wherein said pre-formed section comprises at least one fold, pleat, bellow shaped part or part having a smooth surface, or combinations thereof. Said pre-formed section may have a longitudinal extension in the interval of around 1 to 100 mm.

According to another embodiment there is provided a penile implant wherein said pre-formed section is expandable.

According to a further embodiment there is provided a penile implant which is adapted to be non-invasively adjustable.

According to yet another embodiment there is provided a penile implant wherein said penile implant is adapted to selectively assume a first in-activated state, in which said penile implant may be collapsed, and a second activated state, in which said penile implant may be expanded.

According to yet a further embodiment there is provided a penile implant wherein at least said pre-formed section is hollow or comprises a hollow body.

According to one embodiment there is provided a penile implant wherein said penile implant is substantially completely hollow or comprises a hollow body extending along substantially the complete length of said penile implant.

According to another embodiment there is provided a penile implant which may comprise a transportable medium, e.g. a fluid. The transportable medium is adapted to be received into and pressurize said pre-formed section and/or said penile implant and/or said hollow body, to bring said penile implant into said second activated state. The transportable medium may as well be adapted to be withdrawn from said pre-formed section and/or said penile implant and/or said hollow body, to bring said penile implant into said first in-activated state.

According to a further embodiment there is provided a penile implant wherein said pre-formed section and/or said penile implant and/or said hollow body, is adapted to receive, and be pressurized by, a fluid to bring said penile implant (10) into said second activated state. Further said pre-formed section and/or said penile implant and/or said hollow body may be adapted to release said fluid, or adapted so that said fluid may be withdrawn therefrom, to bring said penile implant into said first in-activated state.

According to a further aspect there is provided a penile implant, in particular a penile implant for curing erectile impotence, wherein said penile implant may be adapted to be implanted in the corpus cavernosum of a penis of a person. Further may said penile implant be adapted to be post-operatively adjustable.

Said penile implant may as well be adapted to selectively assume an in-activated state whereby said penis can be made flaccid, and an activated state whereby said penis can be erected or made erected.

Said penile implant may be collapsed in its in-activated state and expanded in its activated state.

Said penile implant may have a relatively short proximal portion which is suited to be placed or located in the root of the penis, and a flexible relatively long distal portion, which is suited to be placed so as to extend along or to be located in the pendulous or protruding part of the penis.

Said penile implant may further comprise a bending portion placed or located between the proximal and the distal portion, or in the vicinity of the position where the proximal and the distal portion meet.

Said bending portion may be adapted to enable said penile implant, when said penile implant is implanted and activated, to bring at least the pendulous or protruding portion of the penis to a position in which the penis has an acute angle with the vertical plane when said person is standing. That is, a position in which at least the pendulous or protruding portion of the penis is upwardly bent when said person is standing.

The penile implant may optionally have the following further characteristics:

According to one embodiment there is provided a penile implant wherein said bending portion may comprise a pliable or elastic wall part of said penile implant. Said wall part extends along a part of, along parts of, or along the complete, circumference of said penile implant. Said wall part extends in such a way as to, when said penile implant is implanted and activated, bring at least the pendulous part of the penis to a position in which the penis has an acute angle with the vertical plane when said person is standing.

According to another embodiment there is provided a penile implant wherein said wall part extends along at least a part of the underside, and along at least a part of the upper side of said penile implant. Said wall part has a greater longitudinal extension on the underside than on the upper side of said penile implant (10), when said penile implant (10) is activated and/or inactivated. This in order to, when said penile implant is implanted and activated, bring at least the pendulous part of the penis to a position in which the penis has an acute angle with the vertical plane when said person is standing.

According to a further embodiment there is provided a penile implant wherein said bending portion comprises a bellows structure which extends along a part of, along parts of, or along the complete, circumference of said penile implant. Said bellows structure is designed so that at least part of the underside of said penile implant shows a greater length expansion when said penile implant is activated than the upper side of said penile implant. This in order to, to, when said penile implant is implanted and activated, bring at least the pendulous part of the penis to a position in which the penis has an acute angle with the vertical plane when said person is standing.

According to yet another embodiment there is provided a penile implant wherein said bellows structure extends along at least a part of the underside, and along at least a part of the upper side of said penile implant.

Said bellows structure may have a greater longitudinal extension on the underside than on the upper side of said penile implant. Further may said bellows structure have a greater depth, at least when said penile implant is in it's in- or non-activated state, on the underside than on the upper side of said penile implant. This in order to, when said penile implant is implanted and activated, bring at least the pendulous part of the penis to a position in which the penis has an acute angle with the vertical plane when said person is standing.

According to one embodiment there is provided a penile implant wherein said bending portion is positioned at a point or in an area of said penile implant which is in the vicinity of and/or including the position where the pendulous or protruding part of the penis starts.

According to another embodiment there is provided a penile implant wherein said bending portion is positioned at or on said proximal portion, suitably in the vicinity of the position where said proximal portion and said distal portion meet.

According to a further embodiment there is provided a penile implant which is adapted to be non-invasively adjustable.

According to yet another embodiment there is provided a penile implant wherein at least said bending portion is hollow or comprises a hollow body.

According to yet a further embodiment there is provided a penile implant which is substantially completely hollow or comprises a hollow body extending along substantially the complete length of said penile implant.

According to one embodiment there is provided a penile implant which comprises a transportable medium, e.g. a fluid. Said transportable medium is adapted to be received into and pressurize said bending portion and/or said penile implant and/or said hollow body in order to bring said penile implant into said second activated state. Said transportable medium may as well be adapted to be withdrawn from said bending portion and/or said penile implant and/or said hollow body, to bring said penile implant into said first in-activated state.

According to another embodiment there is provided a penile implant wherein said bending portion and/or said penile implant and/or said hollow body, is adapted to receive, and be pressurized by, a fluid to bring said penile implant into said second activated state. Further may said bending portion and/or said penile implant and/or said hollow body be adapted to release said fluid, or adapted so that said fluid may be withdrawn therefrom, to bring said penile implant into said first in-activated state.

According to a further embodiment there is provided a penile implant wherein said bending portion comprises that said proximal portion has a pliable top wall and a pliable bottom wall. Said bottom wall is designed to longitudinally distend more than said top wall, when said penile implant is brought into said second activated state by said transportable medium. This in order to cause said distal portion to bend upwardly in relation to said proximal portion.

According to yet another embodiment there is provided a penile implant wherein said bottom wall of said proximal portion forms circumferentially extending alternating ridges and grooves. Said bottom wall thereby behaves like an expanding bellows when said penile implant is brought into said second activated state by said transportable medium.

According to yet a further embodiment there is provided a penile implant wherein said ridges of said bottom wall are spaced apart from one another, when said penile implant is in its inactivated state.

According to one embodiment there is provided a penile implant wherein said top wall foams circumferentially extending alternating ridges and grooves. These ridges and grooves are dimensioned such that said top wall longitudinally distends less than said bottom wall, when said penile implant is brought into said second activated state by said transportable medium.

According to another embodiment there is provided a penile implant wherein said grooves are wedge-shaped.

According to a further embodiment there is provided a penile implant wherein said ridges have a polygonal cross-section.

According to yet another embodiment there is provided a penile implant wherein said distal portion of said penile implant comprises circumferentially extending alternating ridges and grooves. Thereby said distal portion behaves like an expanding bellows and longitudinally prolongs, when said penile implant is brought into said second activated state by said transportable medium.

According to yet a further embodiment there is provided a penile implant wherein said proximal portion of said penile implant is made of an elastic material.

According to one embodiment there is provided a penile implant wherein said top wall of said proximal portion is substantially thicker than said bottom wall of said proximal portion.

According to a further embodiment there is provided a penile implant wherein said elastic material comprises silicone elastomer.

According to yet another aspect there is provided a penile implant, in particular a penile implant for curing erectile impotence. Said penile implant may be adapted to be implanted in the corpus cavernosum of a penis of a person. Said penile implant is at least partly hollow and/or at least partly comprises a hollow body. Said penile implant comprises a foam material transparent for fluid, said foam material is at least partly filling said penile implant and/or said hollow body.

Suitably said foam material has a lower density than water. Said penile implant and/or said hollow body is adapted to be filled with said foam material and said fluid so that said foam material and said fluid together substantially fill the volume of said penile implant and/or said hollow body.

The penile implant may optionally have the following further characteristics.

According to one embodiment there is provided a penile implant wherein said foam material comprises open spaces that can be filled with said fluid.

According to another embodiment there is provided a penile implant wherein said foam material is a closed cellular foam material which comprises closed spaces, suitably bubbles. The closed spaces may contain, or may be filled with, a solid material, a gas or a fluid, e.g. air or foam material.

According to a further embodiment there is provided a penile implant wherein said penile implant is adapted to be non-invasively adjustable.

According to yet another embodiment there is provided a penile implant, which is adapted to selectively assume a first in-activated state, wherein said penile implant may be collapsed, and a second activated state, wherein said penile implant may be expanded.

According to yet a further embodiment there is provided a penile implant wherein said fluid is adapted to be received into and pressurize said penile implant and/or said hollow body, to bring said penile implant into said second activated state. Said fluid may also be adapted to be withdrawn from said penile implant and/or said hollow body, to bring said penile implant into said first in-activated state.

According to one embodiment there is provided a penile implant wherein said penile implant and/or said hollow body, is adapted to receive, and be pressurized by, a fluid to bring said penile implant (10) into said second activated state. Said penile implant and/or said hollow body may also be adapted to release said fluid, or adapted so that said fluid may be withdrawn, to bring said penile implant into said first in-activated state.

According to yet a further aspect there is provided a penile implant, which may be a penile implant for curing erectile impotence. Said penile implant may be elongated and may be adapted to be implanted in the corpus cavernosum of a penis of a person. Said penile implant may also be adapted to post-operatively be adjustable.

Said penile implant may comprise at least one expandable portion and is adjustable between a first collapsed state and at least one other, partly or fully expanded, state. In the collapsed state the at least one expandable portion is collapsed, and in the other, partly or fully expanded, state said at least one expandable portion is partly or fully expanded.

Said at least one expandable portion may comprise at least one item chosen from the group consisting of; a radially expandable portion, a radially expandable segment, a longitudinally expandable portion, and a longitudinally expandable segment.

Said penile implant may have a predetermined shape with a length and a diameter and may be adapted to allow an increase of the penile implant diameter and/or length when being adjusted from said first collapsed to said at least one partly or fully expanded state. This in order to achieve penile erection with increased penile diameter and/or length when said penile implant is implanted and partly or fully expanded, as compared to a relaxed status of the penis.

According to yet another aspect there is provided a penile implant, which may be a penile implant for curing erectile impotence. Said penile implant may be elongated and may be adapted to be implanted in the corpus cavernosum of a penis of a person. Said penile implant may be adapted to post-operatively be adjustable.

Said penile implant may comprise at least one expandable portion and may be adjustable between a first in-activated or collapsed state and at least one other, partly or fully expanded, activated state. In the first state said at least one expandable portion is collapsed and in the other, activated state, said at least one expandable portion is partly or fully expanded.

Said at least one expandable portion may comprise a radially expandable portion and/or a radially expandable segment at least partly comprising a cross section presenting at least one concaveness or indentation. Said cross section may present a concaveness or indentation facing the urethra of the penis.

Said penile implant may have a predetermined shape with a length and a diameter and may be adapted to allow an increase of the penile implant diameter when being adjusted from said first in-activated or collapsed state to said at least one other, partly or fully expanded, activated state. This in order to achieve penile erection with increased penile diameter when said penile implant is implanted and partly or fully expanded, as compared to a relaxed status of the penis.

The penile implant may optionally have the following further characteristics.

According to one embodiment there is provided a penile implant wherein said radially expandable portion or said radially expandable segment at least partly comprises a cross section presenting at least one concaveness or indentation.

According to another embodiment there is provided a penile implant wherein said cross section presents at least two concavenesses or indentations.

According to a further embodiment there is provided a penile implant wherein said cross section presents a concaveness or indentation facing the urethra.

According to yet another embodiment there is provided a penile implant which comprises said radially expandable portion or said radially expandable segment on the part of said penile implant that is adapted to be placed in the protruding or pendulous part of the penis.

According to yet a further embodiment there is provided a penile implant wherein said at least one expandable portion comprises a longitudinally expandable portion or a longitudinally expandable segment. The longitudinally expandable portion or the longitudinally expandable segment may comprise a longitudinally expandable structure that comprises at least one concaveness or indentation.

According to one embodiment there is provided a penile implant wherein said at least one expandable portion comprises a longitudinally expandable portion or a longitudinally expandable segment. The longitudinally expandable portion or the longitudinally expandable segment may comprise a longitudinal bellows structure that comprises ridges and grooves that extend substantially circumferentially along a part of, along parts of, or along the complete, circumference of said penile implant.

According to another embodiment there is provided a penile implant wherein said longitudinally expandable portion or said longitudinally expandable segment is present on a proximal part of said penile implant. The proximal part may be adapted to be placed in the root part of the penis. The root part of the penis extends substantially on the inside of the body.

According to a further embodiment there is provided a penile implant wherein said longitudinally expandable portion or said longitudinally expandable segment is present on a distal part of said penile implant. Said distal part in suitably adapted to be placed in the protruding or pendulous part of the penis.

According to one embodiment there is provided a penile implant wherein;
the distance between the substantially opposing sides of the at least one concaveness or indentation,
and/or
the distance between the substantially opposing sides of the ridges and grooves of the longitudinal bellows structure,
is sufficiently extended to prevent growth of fibrotic tissue from directly interconnecting said substantially opposing sides to an extent that compromises the adjustability between a first collapsed state and at least one other, partly or fully expanded, state.

According to another embodiment there is provided a penile implant wherein;
the distance between the substantially opposing sides of the at least one concaveness or indentation,
and/or
the distance between the substantially opposing sides of the ridges and grooves of the longitudinal bellows structure,
is greater than around 1 mm, greater than around 2 mm, or greater than around 3 mm.

According to yet another embodiment there is provided a penile implant which is adapted to be non-invasively adjustable.

According to a further embodiment there is provided a penile implant wherein at least said at least one expandable portion is hollow or comprises a hollow body.

According to yet a further embodiment there is provided a penile implant wherein said penile implant is substantially completely hollow or comprises a hollow body extending along substantially the complete length of said penile implant.

According to one embodiment there is provided a penile implant wherein said penile implant comprises a transportable medium, e.g. a fluid. The transportable medium may be adapted to be received into and pressurize said at least one expandable portion and/or said penile implant and/or said hollow body. This in order to bring said penile implant into said at least one partly or fully expanded state. The transportable medium may also be adapted to be withdrawn from said at least one expandable portion and/or said penile implant and/or said hollow body, to bring said penile implant (10) into said first collapsed state.

According to another embodiment there is provided a penile implant wherein said at least one expandable portion and/or said penile implant and/or said hollow body, is adapted to receive, and to be pressurized by, a fluid. This in order to bring said penile implant into said at least one partly or fully expanded state. Said at least one expandable portion and/or said penile implant and/or said hollow body may also be adapted to release said fluid, or adapted so that said fluid may be withdrawn, to bring said penile implant into said first collapsed state.

According to a further embodiment there is provided a penile implant wherein said penile implant or said hollow body comprises a first and at least one second compartment both being adapted to be filled and pressurized with a fluid. The first and the at least one second compartment are separated by at least one dividing wall having at least one valve.

Said radially expandable segment and said longitudinally expandable segment may each comprise at least one of; a second compartment, a dividing wall having at least one valve, at least one invagination.

Said at least one second compartment comprises at least one invagination. Said at least one valve suitably has a first side or face which is adapted to be closed for fluid up to a predetermined fluid pressure threshold. For fluid pressures above said fluid pressure threshold said at least one valve is adapted to open. Said at least one valve suitably also has a second side or face which is adapted to be open for fluid at substantially any pressure, at least for a pressure greater than zero.

Said at least one invagination is adapted to bulge when subjected to fluid pressure and to resume its invaginated form when said fluid pressure is removed.

According to yet a further embodiment there is provided a penile implant wherein said first compartment is adapted to be connected to a source of pressurized fluid.

Said first side or face of said at least one valve is suitably facing said first compartment and said second side or face of said at least one valve is suitably facing said at least one second compartment. This is in order to enable that said at least one second compartment can be filled and pressurized with fluid when the fluid pressure in said first compartment exceeds said fluid pressure threshold so that said at least one invagination bulges and hence prolongs or radially expands said penile implant and/or hollow body.

According to yet another embodiment there is provided a penile implant wherein said penile implant or said hollow body comprises a longitudinally expandable portion having a first and a second hollow portion. The first and the second hollow portion are each adapted to be filled and pressurized with a fluid, they may be connected by an elastic first conduit, and optionally also by an elastic second conduit. The first and the second hollow portion may as well be connected by an elastic connecting portion.

At least one of, and suitably each of, said first and second hollow portions comprises at least one invagination. Said invagination is suitably adapted to bulge when subjected to fluid pressure and to resume its invaginated form when said fluid pressure is removed.

According to one embodiment there is provided a penile implant wherein each of said first and second hollow portions comprises an invagination. Said invaginations are suitably facing each other and are adapted to bulge and mutually exert a force on each other when subjected to fluid pressure. This in order to prolong said penile implant and/or hollow body when said first and second hollow portions are filled and pressurized with a fluid. Said invaginations are suitably adapted to resume their invaginated form when said fluid pressure is removed so that said penile implant and/or hollow body resumes its not prolonged length.

In another aspect there is provided a surgery method where a penile implant as described above is implanted in the patient.

In a further aspect there is provided a system that comprises a penile implant as described above.

In one embodiment the system comprises at least one switch implantable in the patient for manually and non-invasively controlling the penile implant.

In one embodiment the system comprises a hydraulic device having an implantable hydraulic reservoir, which is hydraulically connected to the penile implant, wherein the penile implant is adapted to be non-invasively regulated by manually pressing the hydraulic reservoir.

In one embodiment the system comprises a wireless remote control for non-invasively controlling the penile implant. The wireless remote control may comprise at least one external signal transmitter and/or receiver, further comprising an internal signal receiver and/or transmitter implantable in the patient for receiving signals transmitted by the external signal transmitter or transmitting signals to the external signal receiver.

In one embodiment the wireless remote control transmits at least one wireless control signal for controlling the penile implant.

In one embodiment the wireless control signal comprises a frequency, amplitude, or phase modulated signal or a combination thereof.

In one embodiment the wireless remote control transmits an electromagnetic carrier wave signal for carrying the control signal.

One embodiment comprises a wireless energy-transmission device for non-invasively energizing implantable energy consuming components of the penile implant with wireless energy.

In one embodiment there is provided a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. The signal may be an analogue signal, a digital signal, or a combination of an analogue and digital signal The wireless energy may be different in different embodiments, for example: an electric field, a magnetic field, or a combined electric and magnetic field.

The control signal may be different in different embodiments, for example an electric field, a magnetic field, or a combined electric and magnetic field.

In another embodiment there is provided an implantable internal energy source for powering implantable energy consuming components of the penile implant.

In one embodiment there is provided an external energy source for transferring energy in a wireless mode, wherein the internal energy source is chargeable by the energy transferred in the wireless mode.

In one embodiment there is provided a sensor or measuring device sensing or measuring a functional parameter correlated to the transfer of energy for charging the internal energy source, and a feedback device for sending feedback information from inside the patient's body to the outside thereof, the feedback information being related to the functional parameter sensed by the sensor or measured by the measuring device.

One embodiment further comprises a feedback device for sending feedback information from inside the patient's body to the outside thereof, the feedback information being related to at least one of a physical parameter of the patient and a functional parameter related to the penile implant.

In one embodiment there is provided a sensor and/or a measuring device and an implantable internal control unit for controlling the penile implant in response to information being related to at least one of a physical parameter of the patient sensed by the sensor or measured by the measuring device and a functional parameter related to the penile implant sensed by the sensor or measured by the measuring device. The physical parameter may be a pressure or a motility movement.

In one embodiment there is provided an external data communicator and an implantable internal data communicator communicating with the external data communicator, wherein the internal communicator feeds data related to the penile implant or the patient to the external data communicator and/or the external data communicator feeds data to the internal data communicator.

In one embodiment there is provided a motor or a pump for operating the penile implant.

In one embodiment there is provided a hydraulic operation device for operating the penile implant.

In one embodiment there is provided an operation device for operating the penile implant, wherein the operation device comprises a servo designed to decrease the force needed for the operation device to operate the penile implant instead the operation device acting a longer way, increasing the time for a determined action.

In one embodiment there is provided a operation device for operating the penile implant, wherein the wireless energy is used in its wireless state to directly power the operation device to create kinetic energy for the operation of the penile implant, as the wireless energy is being transmitted by the energy-transmission device.

In one embodiment there is provided an energy-transforming device for transforming the wireless energy transmitted by the energy-transmission device from a first form into a second form energy.

In one embodiment the energy-transforming device directly powers implantable energy consuming components of the penile implant with the second form energy, as the energy-transforming device transforms the first form energy transmitted by the energy-transmission device into the second form energy.

In one embodiment the second form energy comprises at least one of a direct current, pulsating direct current and an alternating current.

In one embodiment there is provided an implantable accumulator, wherein the second form energy is used at least partly to charge the accumulator.

In one embodiment the energy of the first or second form comprises at least one of magnetic energy, kinetic energy, sound energy, chemical energy, radiant energy, electromagnetic energy, photo energy, nuclear energy thermal energy, non-magnetic energy, non-kinetic energy, non-chemical energy, non-sonic energy, non-nuclear energy and non-thermal energy.

In one embodiment there are provided implantable electrical components including at least one voltage level guard and/or at least one constant current guard.

In one embodiment there is provided a control device for controlling the transmission of wireless energy from the energy-transmission device, and an implantable internal energy receiver for receiving the transmitted wireless energy, the internal energy receiver being connected to implantable energy consuming components of the penile implant for directly or indirectly supplying received energy thereto, the system further comprising a determination device adapted to determine an energy balance between the energy received by the internal energy receiver and the energy used for the implantable energy consuming components of the penile implant, wherein the control device controls the transmission of wireless energy from the external energy-transmission device, based on the energy balance determined by the determination device.

In one embodiment the determination device is adapted to detect a change in the energy balance, and the control device controls the transmission of wireless energy based on the detected energy balance change.

In one embodiment the determination device is adapted to detect a difference between energy received by the internal energy receiver and energy used for the implantable energy consuming components of the penile implant, and the control device controls the transmission of wireless energy based on the detected energy difference.

In one embodiment the energy-transmission device comprises a coil placed externally to the human body, further comprising an implantable energy receiver to be placed internally in the human body and an electric circuit connected to power the external coil with electrical pulses to transmit the wireless energy, the electrical pulses having leading and trailing edges, the electric circuit adapted to vary first time intervals between successive leading and trailing edges and/or second time intervals between successive trailing and leading edges of the electrical pulses to vary the power of the transmitted wireless energy, the energy receiver receiving the transmitted wireless energy having a varied power.

In one embodiment the electric circuit is adapted to deliver the electrical pulses to remain unchanged except varying the first and/or second time intervals.

In one embodiment the electric circuit has a time constant and is adapted to vary the first and second time intervals only in the range of the first time constant, so that when the lengths of the first and/or second time intervals are varied, the transmitted power over the coil is varied.

In one embodiment there is provided a system comprising an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off.

In one embodiment there is a an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils.

In one embodiment the transmitted energy may be regulated depending on the obtained coupling factor.

In one embodiment there is provided a system wherein the external second coil is adapted to be moved in relation to the internal first coil to establish the optimal placement of the second coil, in which the coupling factor is maximized.

In one embodiment there is provided a system wherein the external second coil is adapted to calibrate the amount of transferred energy to achieve the feedback information in the determination device, before the coupling factor is maximized.

In a yet further aspect there is provided an operation method using a penile implant or system according to the above further comprising the steps of: a) creating an opening in the skin or penis wall of the male patient, b) dissecting an one area of the sexually responsive tissue, c) placing the penile implant within said area, adapted to postoperatively stimulate said sexually responsive tissue on patient command.

In one embodiment there is provided an operation method comprising the step of placing an operation device and a power source within the body.

In one embodiment the operation method comprises placing a penile implant comprising placing an integrated unit comprising the penile implant and an operation device in the same integrated unit.

In one embodiment the operation method comprises placing a power source comprising, placing an control unit and a rechargeable battery remote from said sexually responsive tissue.

In one embodiment the operation method comprises controlling said penile implant post-operatively and non-invasively from outside the body.

In one embodiment the operation method comprises the step of creating an opening in the skin or penis wall of the male patient comprising, a) inserting a tube or needle into the patients body, b) filling the tube or needle with a gas and thereby expanding a cavity within the male patients body, c) inserting at least two laparoscopic trocars into said cavity, d) inserting at least one camera trough at least one laparoscopic trocar, e) inserting at least one dissecting tool through at least one laparoscopic trocar.

In one embodiment the penile implant is adapted to be implanted in any, or each, of the corpus cavemosum of the penis of the male patient.

In one embodiment the penile implant is adapted to be implanted in the vicinity of, or in contact with, the glans penis of the penis of the male patient.

According to one embodiment there is provided a system comprising at least one penile implant. Said penile implant is adapted to bring a penis to an erected state, when said penile implant is implanted in the corpus cavemosum of the penis and activated or expanded.

Said penile implant is suitably adapted to bring a penis to a flaccid state, when said penile implant is implanted in the corpus cavernosum of the penis and in-activated or collapsed.

According to a further embodiment there is provided a system comprising two penile implants. Said penile implants are adapted to bring a penis to an erected state, when each of said penile implants is implanted in a corpus cavernosum of the penis of a person and activated or expanded.

Said penile implants arc suitably adapted to bring a penis to a flaccid state, when each of said penile implants is implanted in the corpus cavernosum of the penis of a person and in-activated or collapsed.

According to one aspect there is provided a method of implanting the penile implant in a person or patient.

According to a further aspect there is provided a method of implanting the system in a person or patient.

In an preferred embodiment, the system comprises at least one switch implantable in the patient for manually and non-invasively controlling the penile implant.

In another preferred embodiment, the system comprises a wireless remote control for non-invasively controlling the penile implant.

In a preferred embodiment, the system comprises a hydraulic operation device for operating the penile implant.

In one embodiment, the system comprises comprising a motor or a pump for operating the penile implant.

BRIEF DESCRIPTION OF THE DRAWINGS

Before the invention described herein is described in detail, it is to be understood that it is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" also include plural referents unless the context clearly dictates otherwise. Thus, for example, reference to "an element" includes more than one such element, and the like. The invention will now be described by way of non limiting embodiments with reference to the accompanying drawings in which a penis is used to exemplify any organ, i.e. the invention is not limited to a penis only but may be applied to any organ:

FIGS. 40, 41 schematically show an embodiment where the penile implant 10 or hollow body 12, 12a, 12b comprises a hollow part, a longitudinally expandable segment 564, respectively radially expandable segments 572a, 572b, FIG. 42 schematically show an embodiment where the penile implant 10 or hollow body 12, 12a, 12b is divided in or comprises a first hollow or expandable portion 584 and a second hollow or expandable portion 586, FIGS. 43-57 schematically show various embodiments of the system for wirelessly powering the penile implant shown in FIG. 1b.

FIGS. 62-68c show various ways of arranging hydraulic or pneumatic powering of an penile implant implanted in a patient.

The system 700 may be a system described as system 1000, the system 1000 may as well be a system 700.

The operation device 720 may e.g. comprise at least one device selected from the group consisting of the operation device 1007 and 1008.

The control device 722 may e.g. comprise at least one device selected from the group consisting of the devices 1002, 1006, 1004 and 1041.

The conduit 730 may e.g. comprise at least one device selected from the group consisting of the conduits 1011 and 1003.

DETAILED DESCRIPTION

Before the device described herein is described in detail, it is to be understood that the device is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" also include plural referents unless the context clearly dictates otherwise. Thus, for example, reference to "an element" includes more than one such element, and the like. As mentioned above in connection with the brief description of the drawings, a penis is used to exemplify any organ in the following detailed description, i.e. the invention is not limited to a penis only but may be applied to any organ. Accordingly the feature "penis" also exemplifies other organs as stated in the summary.

Figure 1A:
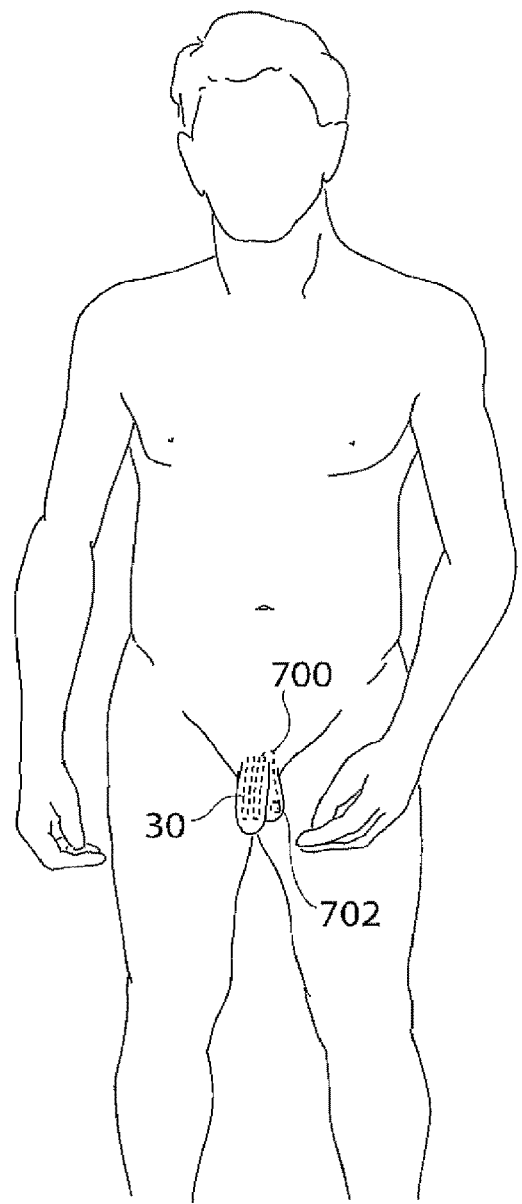
FIGS. 1*a* and 2 schematically show different embodiments of a system 700 implanted in a person.
Figure 2:
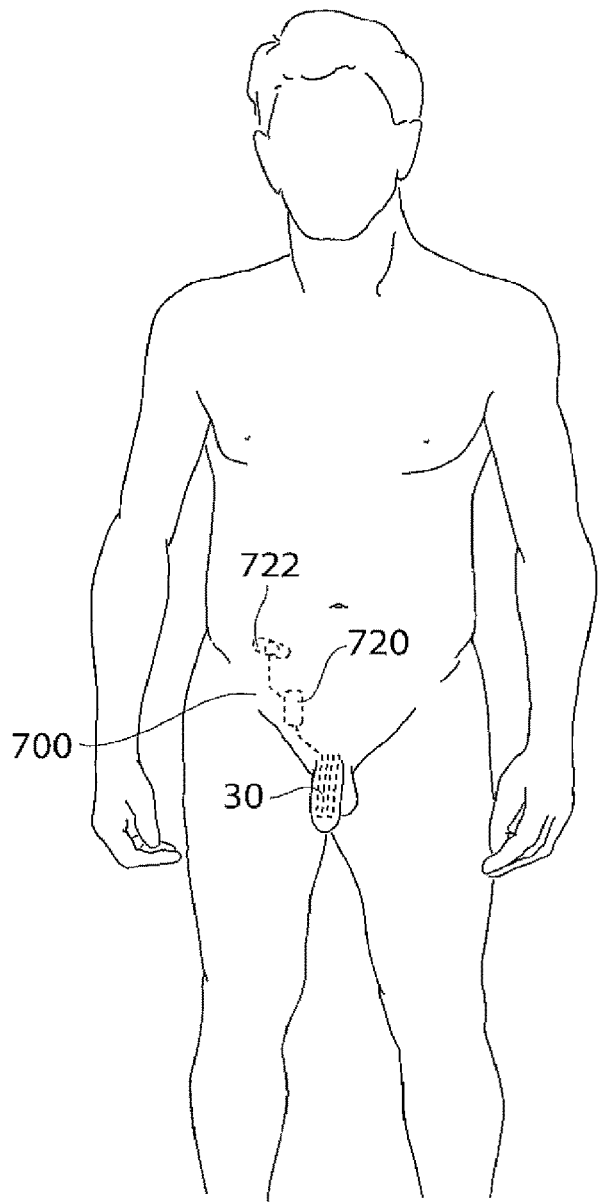

In FIGS. 1 and 2 penile prosthesis systems 700 implanted in a standing person having a penis 30 schematically are shown. FIG. 1a schematically shows a manually operated system having a manual operating device 702 implanted in the scrotum. FIG. 2 schematically shows a powered system having a control device 722 and a powered operating device 720. In both systems a penile implant 10 is suitably implanted in each corpus cavernosum of the penis 30.

Some features of an implantable device according to the invention will now be explained with reference to FIGS. 3 and 4, which show a penile implant 10 implanted in the penis, generally designated 30, of a patient or person. In this embodiment the implantable device 10 comprises three sections: a first inner end section 10a and a second outer end section 10b, and an expandable section 10c provided between the first and second end sections 10a, 10b. The expandable section 10c may also extend along the complete length of the penile implant 10, or the expandable section 10c may extend from the first inner end section 10a and along the rest of the implant 10.

Figure 3:
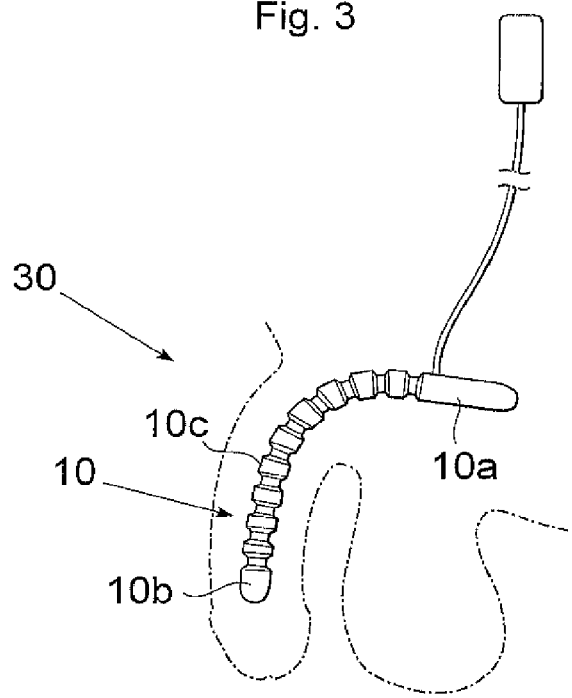
FIG. 3 is a sectional view showing an implantable device 10 according to the invention in a collapsed or inactivated state when implanted in the penis 30 of a patient.
Figure 4:
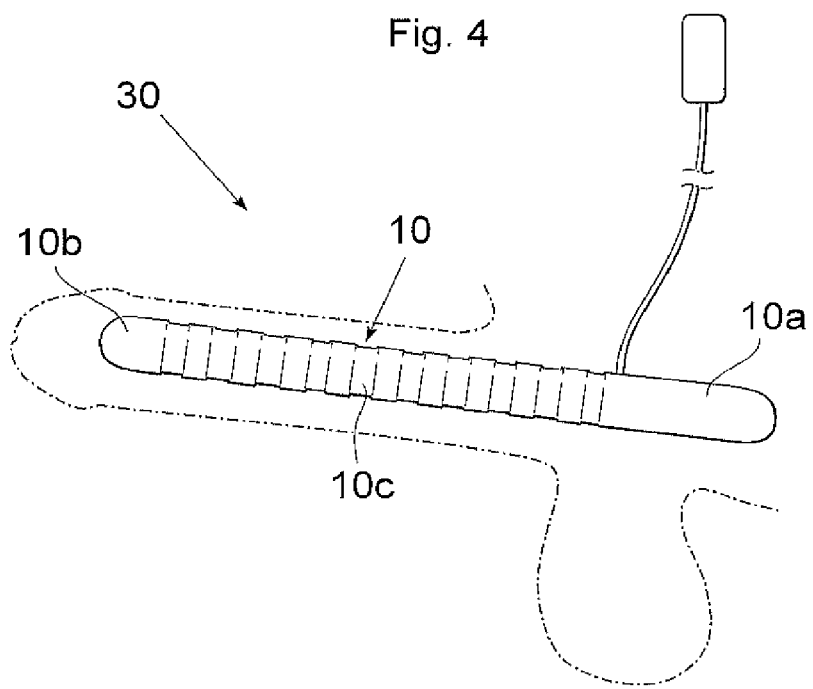
FIG. 4 is a sectional view similar to that of FIG. 3 but showing the implantable device 10 in an expanded state.

The implantable device 10 is adapted to be adjustable between a collapsed or inactivated state, in which the expandable section 10c is collapsed, see FIG. 3, and an expanded state, in which the expandable section 10c is expanded, see FIG. 4.

Surface Structure

One part of the invention is a surface structure 100 comprising elevated areas 101, 110 alternating with lowered areas 102, 112. The outer surface of the expandable section 10c may at least partly comprise this surface structure to provide the mentioned expandability. The configurations and design of the surface structure 100 will be described in more detail below with reference to FIGS. 5-13.

Examples of the surface structure 100 are shown in perspective in FIGS. 5a, 5b, showing the expandable section 10c partly having a surface structure 100.

Figure 6:
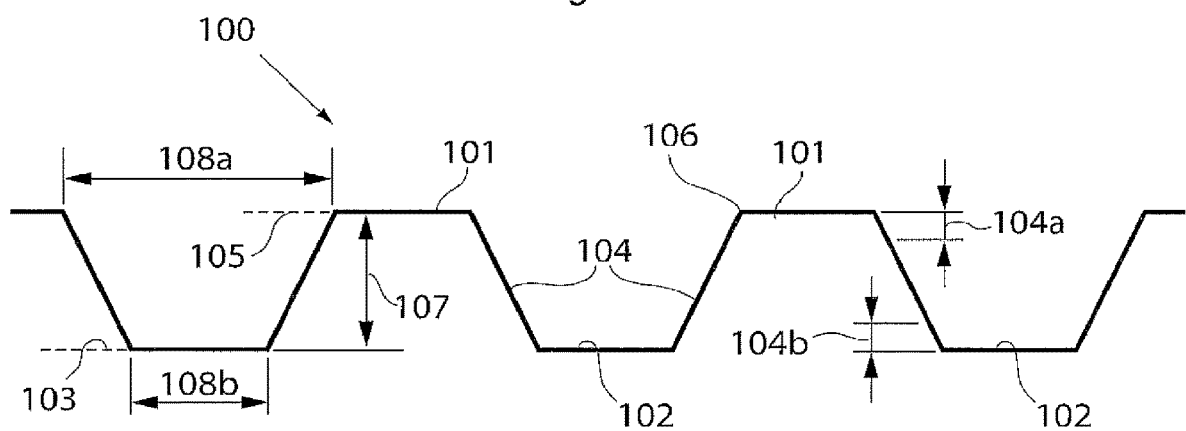
FIG. 6 is a sectional view of a surface structure 100 of the implantable device 10.

Referring to FIG. 6, an example of the surface structure 100 comprising alternating elevated areas 101 and lowered areas 102 will be described. The implantable device 10 may comprise the surface structure 100 having elevated and lowered areas on at least a part of the outer surface of the implantable device 10, which makes it at least partially expandable and collapsible. Adjacent elevated and lowered areas are interconnected by connecting areas 104.

A first distance 108a between two elevated areas 101, see FIG. 6, is long enough so as to prevent growth of fibrotic tissue directly connecting two adjacent elevated areas 101. That is, it may be possible that fibrotic tissue grows on the surface of the elevated and lowered areas 101, 102 and the connecting areas 104. However, thanks to the extension of the first distance 108a, fibrotic tissue is prevented from growing directly from one elevated area 101 to another adjacent elevated area 101.

With the expression "growing directly from one elevated area 101 to another elevated area 101" it is e.g. meant that fibrotic tissue grows from one elevated area 101 to another while not or only to a small extent growing on a connecting area 104. As indicated at 104a in FIG. 6, the first distance 108a may be measured within an interval 104a from the level of an elevated area 101. The expression "growing directly from one elevated area 101 to another elevated area 101" also includes the situation that fibrotic tissue grows on adjacent areas, e.g. two adjacent connecting areas 104, with such a thickness that the fibrotic tissue from each adjacent area meet and bridge the distance or space between two elevated areas 101. In such a situation the space between two elevated areas 101 may be partly or completely filled with fibrotic tissue.

It may be suitable that also a second distance 108b corresponding to the extension of a lowered area 102 has an extension great enough so as to prevent fibrotic tissue from growing directly from one connecting area 104 to another connecting area 104. With the expression "growing directly from one connecting area 104 to another connecting area 104" it is meant that fibrotic tissue grows from one connecting area 104 to another while not or only to a small extent growing on a lowered area 102.

In FIG. 6 a surface structure comprising elevated and lowered areas has been shown, but apart from elevated and lowered areas also many other geometrical structures may be used where it is possible to fulfill the above mentioned prevention of growth of fibrotic tissue. In particular the above mentioned prevention of growth of fibrotic tissue between elevated areas and between connecting areas.

Some examples of such other geometrical structures are shown in FIGS. 57 and 11-13. In a surface structure comprising ridges and grooves, the ridges and grooves may also have different sections, some examples are shown in FIGS. 7a-7d.

Referring mainly to FIGS. 6 and 7a some expressions and aspects will now be explained. In this application the concept of a first distance 108a, 118a between adjacent elevated areas 101, 110 is used. With such a first distance 108a, 118a it is meant a distance that is measured substantially from the edge 106, 114 of one elevated area 101, 110 to the edge 106, 114 of an adjacent elevated area 101, 110. Measured substantially from the edge means that the measurement may be done within a first interval 104a from the level of an elevated area 101, 110, the first interval 104a extending from the level of an elevated area 101, 110 towards the level of an adjacent lowered area 102, 112.

In this application also the concept of a second distance 108b, 118b between adjacent connecting areas 104, 116 is used. With such a second distance 108b, 118b it is meant a distance that is measured substantially from the connection point between a connecting area 104, 116 and a lowered area 102, 112 to another connection point involving an adjacent connecting area 104, 116. Measured substantially from the connection point means that the measurement may be done within a second interval 104b from the level of a lowered area 102, 112, the second interval 104b extending from the level of a lowered area 102, 212 towards the level of an adjacent elevated area 101, 110.

With elevated and lowered areas it is meant areas that lie in different planes 103, 105, 120, 122 where the planes arc separated by a distance 107, 124, 128. The planes may be parallel or substantially parallel but may also be non-parallel. If the planes are parallel, defining a distance between them is trivial. If the planes are non-parallel (as in FIG. 7a) a distance between the planes may be defined by a normal 124, 128 to one of the planes 120, 122 where the normal extend to a point on an area in another plane 122, 126 and the distance between the planes is equal to the extension of the normal 124, 128. As seen in FIG. 7a the normal 124, 128 extends from a plane 120, 122 to a point which is approximately equally distant from the edges of an area. There are two possible ways to define the normal or distance between the planes. Taking normal 128 as example, one may define the normal as in 128a or in 128b. It may be suitable to define the distance between two planes as the extension of the longest normal, the distance between the planes 120 and 122 would then be equal to the extension of normal 128a. *This definition will be used hereafter.*

The elevated and lowered areas may have different shapes, they may be plane or substantially plane but they may also have some kind of curved shape.

The elevated areas 101, 110 connect to adjacent lowered areas 102, 112 by means of connecting areas 104, 116. The connection between elevated/lowered areas and connecting areas 104, 116 may comprise a radius of different sizes, bigger or smaller radii. When the radius is very small there will substantially be an edge 106, 114 connecting the areas.

The expression "expandable section" implies that said section also is collapsible.

Suitably the implantable device 10 at least partly comprises materials which have a high degree of biocompatibility, such materials may be called physiologically inert, biologically inert or biocompatible.

As said before, an suitable application for such an implantable device 10 is a penile prosthesis for curing erectile impotence. The implantable device 10 may at least partly be expandable and/or collapsible and the formation of fibrotic tissue on such an implantable device 10 could impede the function or even render the function of the implantable device 10 impossible. But, an implantable device 10 comprising a surface structure 100 as described herein would not be impeded, or at least only impeded to a small degree, in its function.

A penile implant 10 including a surface structure 100 is suitablely adapted to be adjustable between a first state and a second state, suitably a first collapsed state and a second expanded state. The penile implant may be activated and/or expanded to different degrees, e.g. fully activated or to some degree partly activated. The first state may e.g. be an in-activated state and the second state may e.g. be an activated state with any degree of activation. The first and second states may also be activated states with different degrees of activation. The mentioned examples for the first and second state are examples, the first and second state may be any two states which the penile implant can assume. Of course it is possible that the penile implant can assume any number of states.

The meaning of partly activated and fully activated may be illustrated with a penile implant which is adjustable in size, as discussed in the section "Summary". The maximum size of the penile implant is reached when the penile implant is fully activated and by partly activating the penile implant to different degrees any size between maximum and minimum may be achieved. The activation may for example be effected by transporting a transportable medium to a hollow body within the implant, but also other means of activation is possible, e.g. mechanical.

Referring in particular to FIGS. 6 and 7*a*, in the surface structure 100 there may suitably be a specified first distance 108*a*, 118*a* between adjacent elevated areas 101, 110. The distance between adjacent elevated areas 101, 110 is chosen so that fibrotic tissue cannot bridge the first distance 108*a*, 118*a* between adjacent elevated areas 101, 110. Hence, the first distance 108*a*, 118*a* between adjacent elevated areas 101, 110 is suitably big enough to prevent the formation of fibrotic tissue that bridges adjacent elevated areas 101, 110.

As mentioned before, there may suitably be a specified second distance 108*b*, 118*b* between adjacent connecting areas 104, 116. The second distance 108*b*, 118*b* between adjacent connecting areas 104, 116 is chosen so that fibrotic tissue can not bridge the second distance 108*b*, 118*b* between adjacent connecting areas 104, 116. Hence, the second distance 108*b*, 118*b* between adjacent connecting areas 104, 116 is suitably big enough to prevent the formation of fibrotic tissue that bridges adjacent connecting areas 104, 116. Some suitable intervals for the first and second distances are mentioned in the section "Summary".

It may also be suitable that a third distance 107, 124, 128*a* between the different planes 103, 105, 120, 122, 126 of the elevated and lowered areas is bigger than a certain threshold to facilitate the collapsible and/or expandable functionality of the implant. If the third distance 107, 124, 128*a* is too small the collapsible and/or expandable functionality of the penile implant may be limited. A suitable interval for the third distance 107, 124, 128*a* is 0.5 to 10 mm, more suitable 2-8 mm and most suitable 3-7 mm. Also regarding the aspect that the fibrotic tissue should not impede the collapsible/expandable functionality of the implantable device it is suitable that the distance 107, 124, 128*a* is not too small, but suitably in the interval/s as mentioned previously.

The surface structure 100 may include objects or elements of different geometrical shapes, for example ridges of different shapes, embossments of different shapes and other objects which enable a surface structure as described herein. The area of the elevated areas 101, 110 may be very small while still resulting in a surface structure that has the desired functionality. The area of the elevated areas 101, 110 may even be almost zero, as exemplified in FIG. 7*d*. Whereas FIGS. 6 and 7*a*-7*d* show cross sections of examples of surface structures 100, FIGS. 5*a*, 5*b* and 11-13 show examples of different surface structures 100 in perspective. The objects or elements in the surface structure 100 may be placed in rows, ordered in some other way, or may be more or less randomly distributed over the surface of the implant. Different types of objects may also be used together in the surface structure 100, e.g. a combination of pyramid shaped and cone shaped objects together with ridges of some shape.

Figure 8:
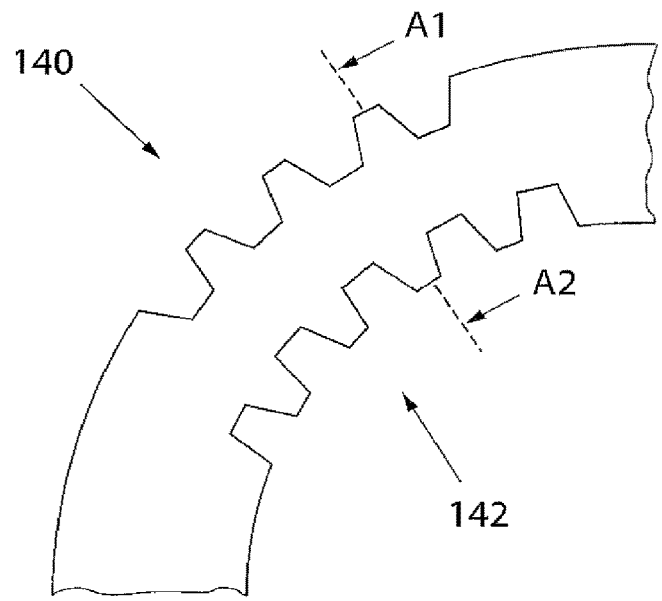
Figure 9:
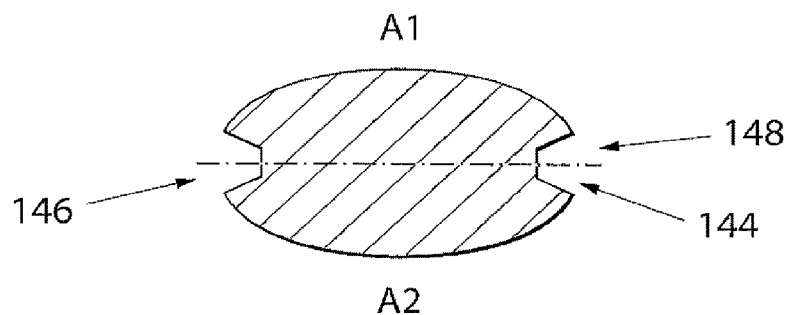
FIGS. 9 and 10 show examples of different cross sections for a penile prosthesis.
Figure 10:
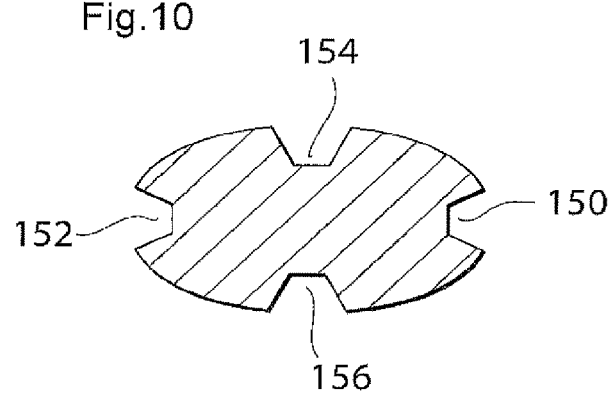
Figure 11:
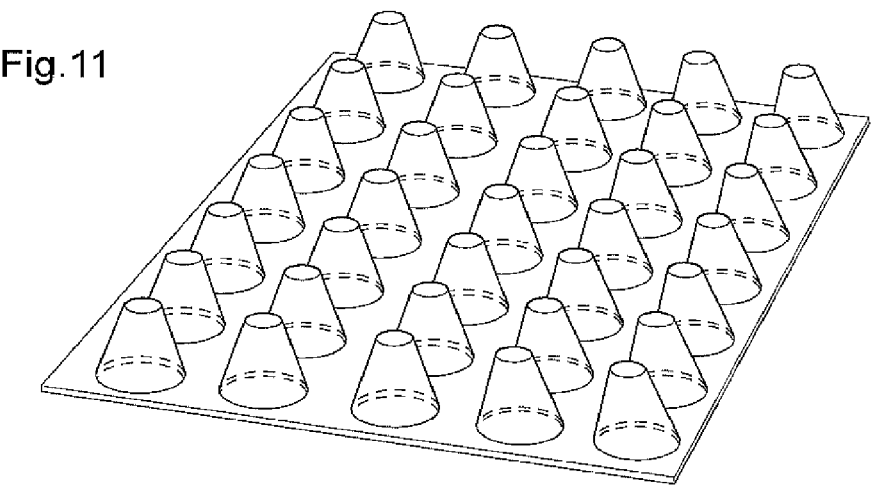
FIGS. 11-13 are drawings showing examples of different surface structures, FIGS. 14-19 schematically show a penile implant 10 comprising some embodiments of the pre-formed section 200, 204, 206, FIGS. 20-26 schematically show a penile implant 10 comprising some embodiments of the bending portion 300, 302, FIGS. 27-30 schematically show a penile implant 10 which is hollow and at least partly is filled with a foam material 400, 402, FIGS. 31a-37b schematically show a penile implant 10 having a radially expandable portion 500, 502 and/or a longitudinally expandable portion 504. A penile implant 10 comprising a hollow body 12, 12a, 12b is also schematically shown.
Figure 12:
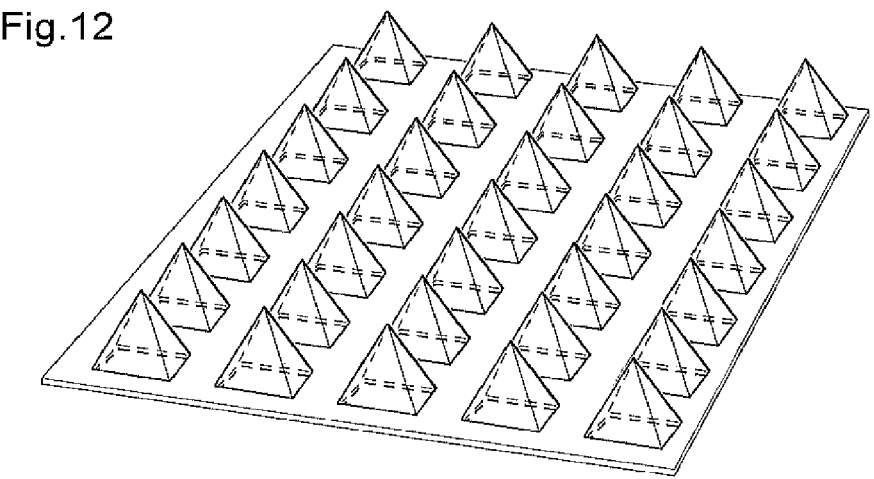
Figure 13:
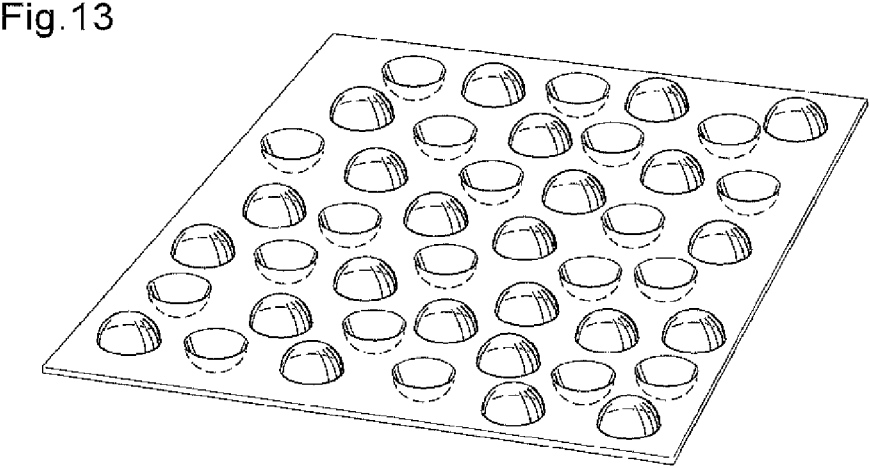

In FIGS. 8-10 an embodiment of a penile prosthesis or penile implant 10 is shown where a surface structure 100 is used, the penile implant 10 is not shown in full. FIG. 8 shows a longitudinal section of the penile implant 10 where 140 denotes the surface structure on the upper side of the penile implant 10 and 142 denotes the surface structure on the under side of the penile implant 10. As shown in FIG. 8 the surface structure 142 on the under side may have a greater extension than the surface structure 140 on the upper side of the penile prosthesis. This gives the penile implant 10 an up-bent position when the penile implant 10 is expanded. This may be suitable since a normally functioning penis has an up-bent position when erected and it is suitable if a penile prosthesis resembles a normally functioning penis. This aspect is more closely discussed in the parts of the application covering the aspect bending portion 300, 302, 302. The surface structures 140 and 142 are one example of a bending portion 300, 302, 302. FIG. 9 shows a cross section of the penile implant 10 where the penile implant 10 includes a waist portion 144, where the waist portion comprises waist surface structures 146 and 148. The waist portion with the waist surface structures 146 and 148 make the penile implant 10 expandable also in the radial direction. The penile implant 10 may also have a cross section as shown in FIG. 10 comprising a waist portion 144 having four waist surface structures 150, 152, 154, 156 further facilitating the ability of the penile implant 10 to be expandable also in the radial direction. The cross sections in FIGS. 9 and 10 are taken along the line A1-A2 in FIG. 8. Radial and longitudinal expandability and means therefore is described more closely in the parts of the application covering the features radially expandable section 500, 502 and longitudinally expandable section 504.

Pre-Formed Section

Figure 5:
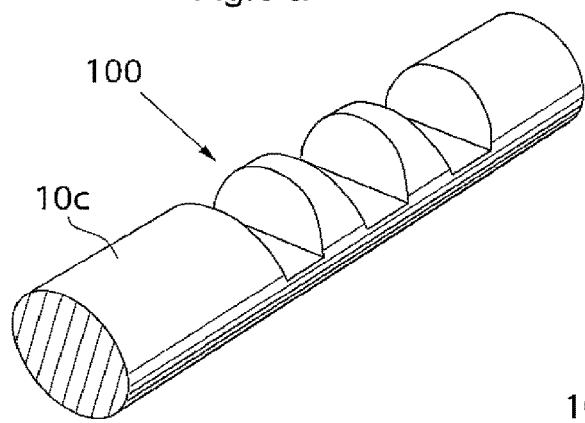
FIGS. 5a, 5b are perspective views showing the expandable section 10c having different embodiments of the surface structure 100.
Figure 5:
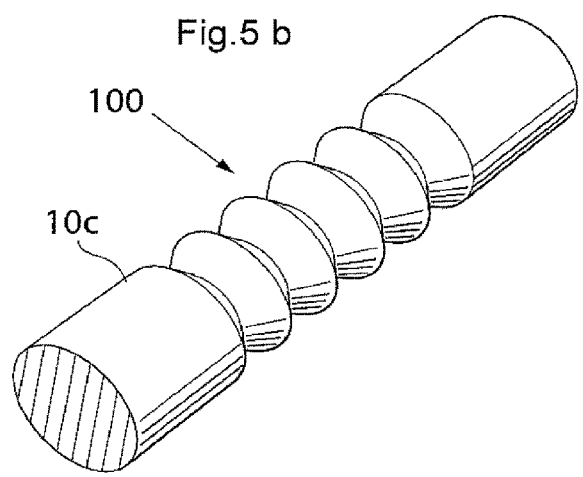
Figure 14:
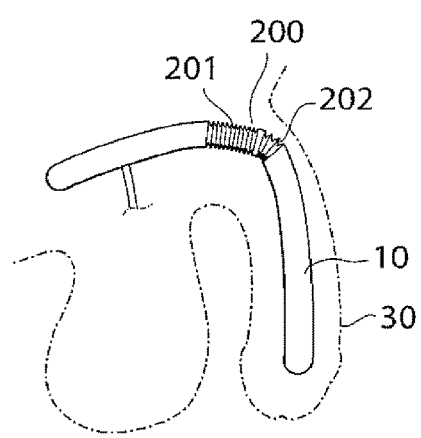
Figure 15:
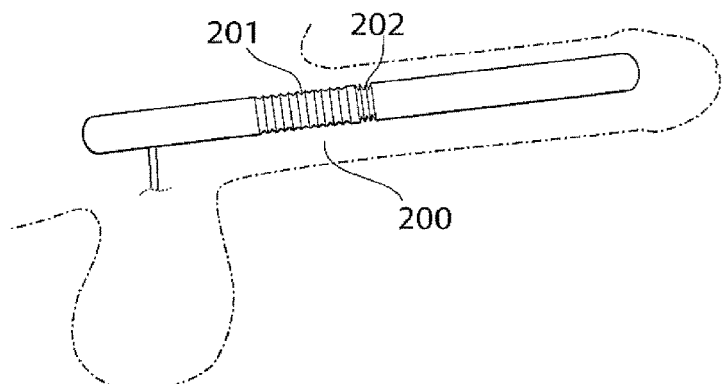

In FIGS. 14-19 some embodiments of the pre-formed section are shown. Each embodiment is shown both when the penile implant 10 is in its collapsed or inactivated state, FIGS. 14, 16 and 18, and when the penile implant 10 is in an activated and/or expanded state, FIGS. 15, 17 and 19. In FIGS. 14 and 15 the pre-formed section 200 comprises a bellow shaped first inner pre-formed part 201 and a bellow shaped second outer pre-formed part 202. This embodiment is suitable e.g. since it is possible to give the different parts 201, 202 different radii so that the penis 30 will have a natural appearance when the penile implant 10 is implanted and collapsed or inactivated. Also from the aspect of reducing or avoiding bending creases in the penile implant 10 it may be an advantage to design different parts of the pre-formed section differently. In case the pre-formed section comprises a bellow shaped part e.g. the depth of the bellow structure and the extension of the ridges and grooves in a direction transversal to the longitudinal direction of the penile implant may be altered. As shown in FIG. 1*a*5 the pre-formed section 200 is designed so that the penis 30 adopts a substantially straight shape when the penile implant 10 is implanted and activated and/or expanded.

Figure 7:
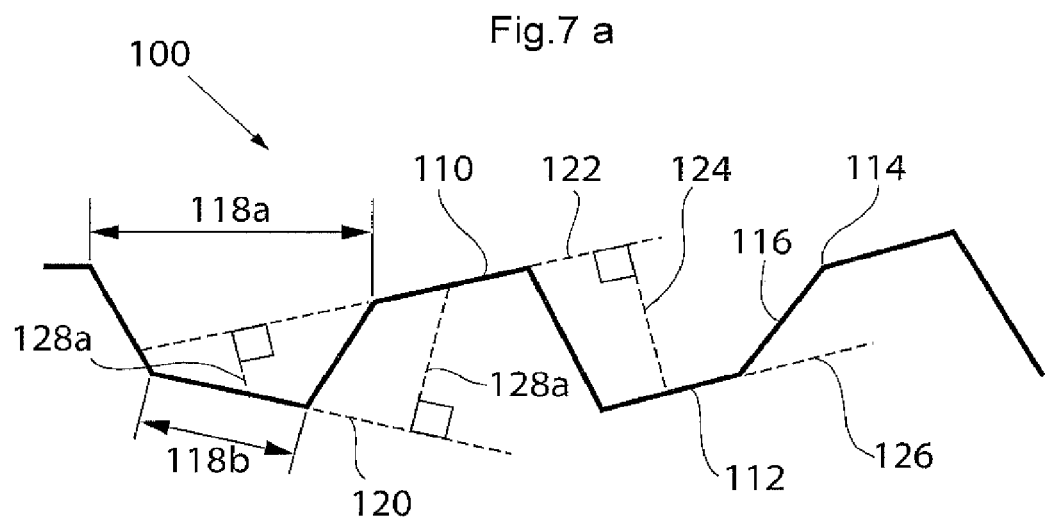
FIG. 7a is a sectional view similar to that of FIG. 6 but with a slightly different surface structure 100.
FIGS. 7b-d are drawings showing sections of examples of the surface structure 100 described herein, FIG. 8 schematically shows an embodiment of a penile implant 10 having a surface structure 100.
Figure 7:
Figure 7:
Figure 7:
Figure 16:
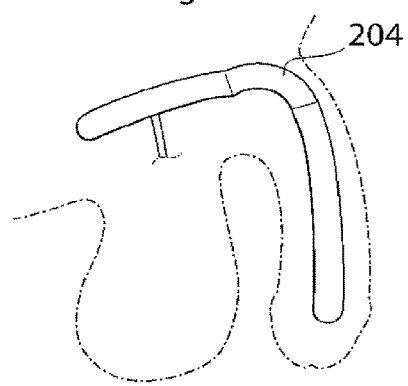
Figure 17:
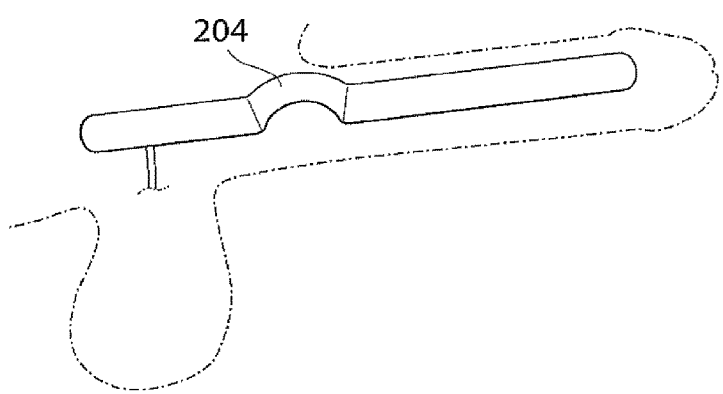

In FIGS. 16 and 17 the pre-formed section 204 comprises an even surface and is pre-formed so that bending creases are avoided or reduced when the penile implant 10 is implanted and the penis is in a relaxed position, and so as to give the penis 30 a natural appearance when the penile implant 10 is implanted and collapsed or inactivated. As shown in FIG. 1*a*7 the pre-formed section 204 is also designed so that the penis 30 adopts a substantially straight shape when the penile implant 10 is implanted and activated and/or expanded. This can be achieved e.g. by forming the underside of the pre-formed section 204 of a material having greater elasticity than the material of the upper side of the pre-formed section 204, so that the underside of the pre-formed section 204 shows a greater longitudinal expansion than the upper side when the penile implant 10 is activated and/or expanded. Activation or expansion of the penile implant 10 may e.g. comprise filling the same with a pressurized transportable medium, e.g. a fluid.

Figure 18:
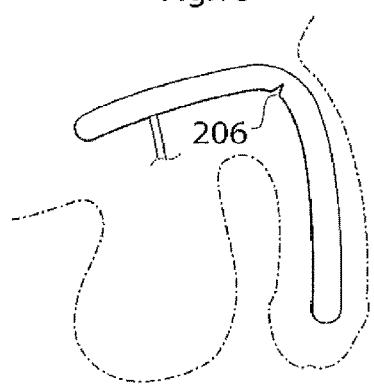
Figure 19:
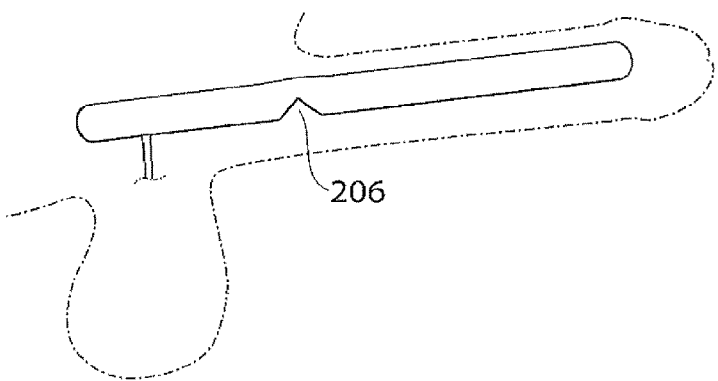

In FIGS. 18 and 19 the pre-formed section 206 comprises a fold or pleat designed so that bending creases are avoided or reduced when the penile implant 10 is implanted and the penis is in a relaxed position, and so as to give the penis 30 a natural appearance when the penile implant 10 is implanted and collapsed or inactivated. As shown in FIG. 19 the pre-formed section 206 is also designed so that the penis 30 adopts a substantially straight shape when the penile implant 10 is implanted and activated and/or expanded.

Figure 20:
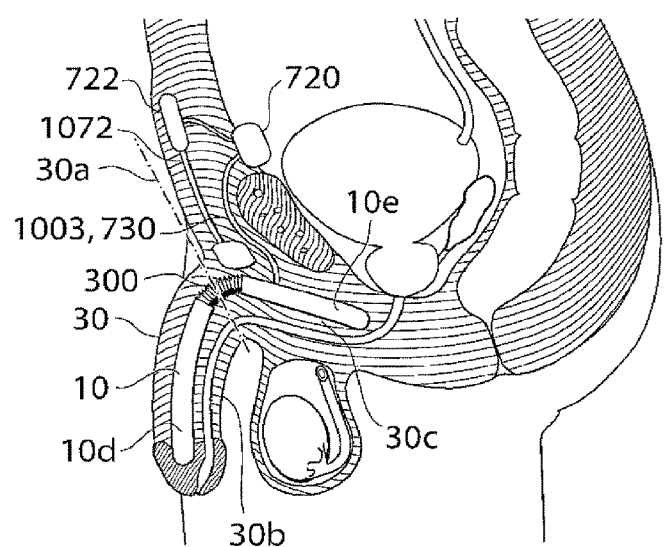

As seen in FIG. 20 the penis 30 can be said to have a pendulous penis portion 30b, extending outside the body and being the part to the left of the line 30a, and a root penis portion 30c extending inside the body and being the part to the right of the line 30a. The penile implant 10 has a distal portion 10d located in the pendulous penis portion 30b and a proximal portion 10e located in the root penis portion 30c.

Bending Portion

Figure 21:
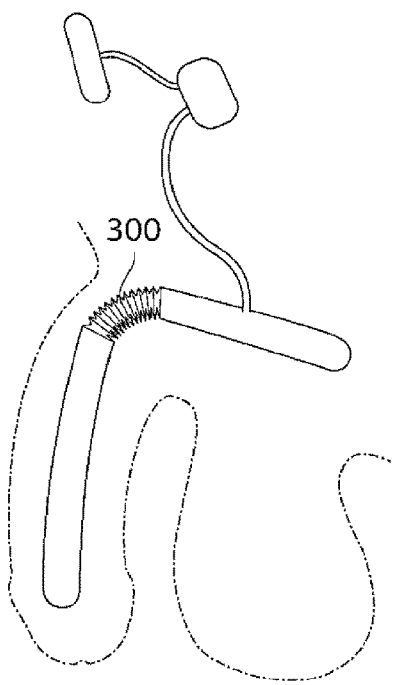
Figure 22:
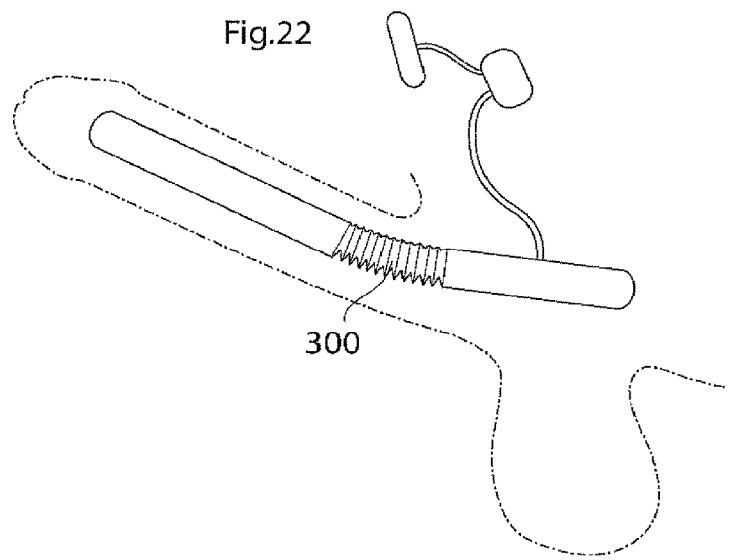
Figure 23A:
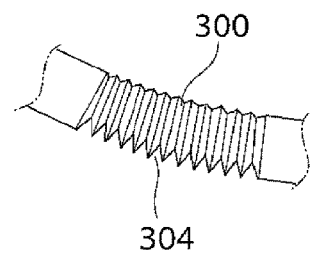
Figure 23B:
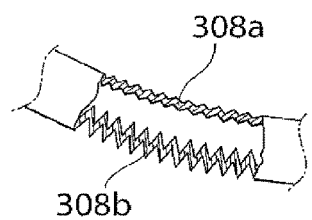
Figure 24:
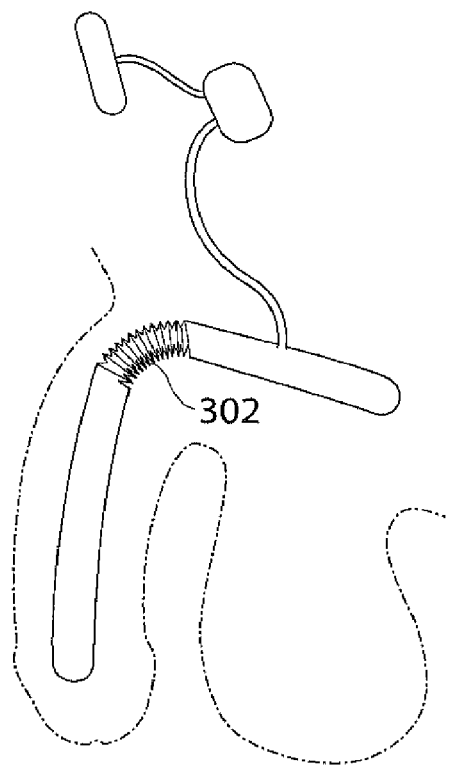
Figure 25:
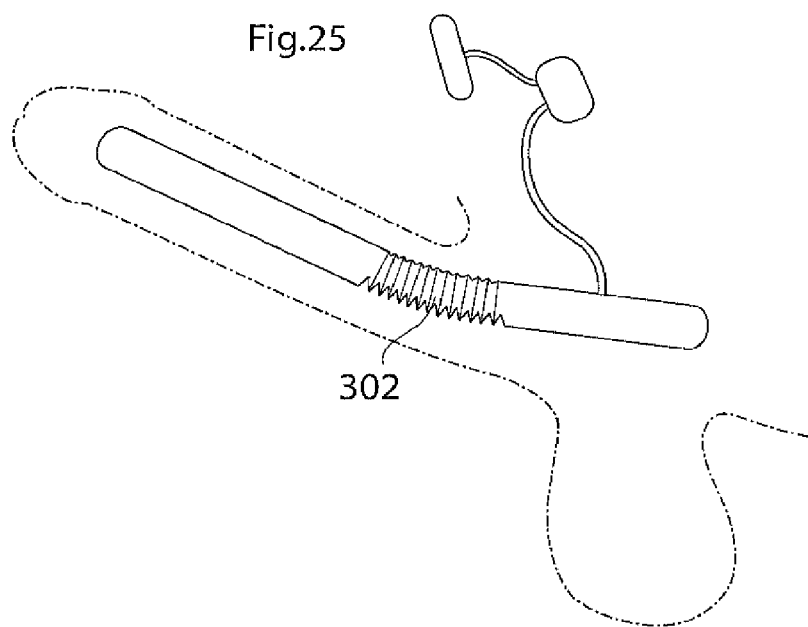
Figure 26:
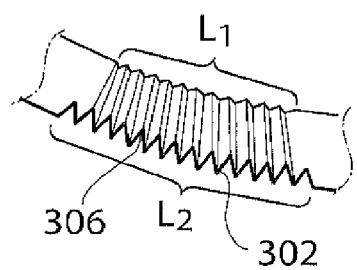
Figure 27:
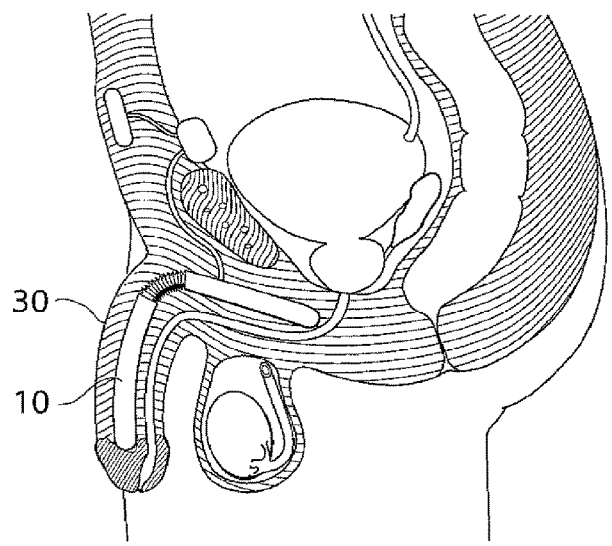

In FIGS. 20-26 the aspect bending portion is illustrated. In FIG. 20 one suitable location on the penile implant 10 of a bending portion 300, 302 is illustrated. The penile implant 10 is implanted in the corpus cavernosum of a penis 30. The penile implant 10 is connected to a powered operating device 702 and a control device 704 and is part of a penile prosthesis system. Of course a penile implant 10 according to any embodiment and comprising any aspect or feature described herein, or combination thereof, can be connected to a powered operating device 702 and a control device 704 and be part of a penile prosthesis system. The bending portion 300, 302 shown in FIG. 23a is bellow shaped and the depth of the bellows structure 304 is greater on the under side of the bending portion 300, 302 than on the upper side. In this way a penile implant 10 comprising the bending portion 300, 302 will bend upwardly when the penile implant 10 is activated and/or expanded since the under side of the bending portion 300, 302 will show a greater longitudinal expansion than the upper side. In FIG. 23b a bending portion 300, 302 having a pliable top wall 308a and a pliable bottom wall 308b in illustrated. The bottom wall 308b is designed to longitudinally distend more than the top wall 308a, when the penile implant 10 is activated, e.g. expanded. In FIGS. 21 and 22 a penile implant 10 comprising a bending portion 300, 302 is shown in a collapsed or inactivated respectively an activated and/or expanded state. In FIGS. 24-26 a bending portion 302 is shown having an alternative embodiment with a bellows structure 306 where the underside of the bending portion 302 has a greater longitudinal extension than the upper side. The function is the same as is the embodiment shown in FIGS. 21-23. The embodiments respectively illustrated in FIGS. 21-23 and 24-26 may also be combined. The bending portion may be of use in any implant where a bending function in desired.

Pre-Filled

Figure 28:
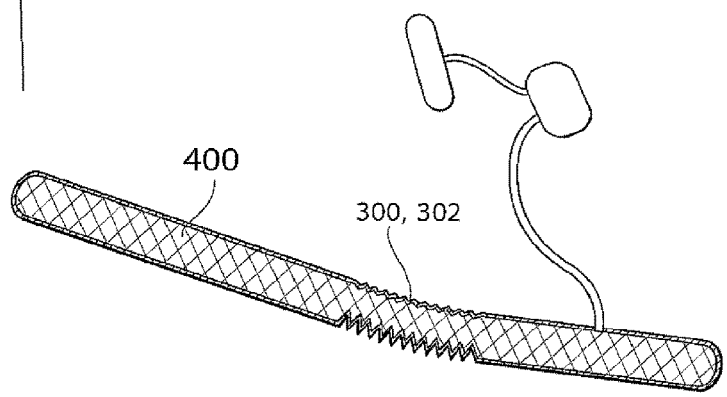
Figure 29:
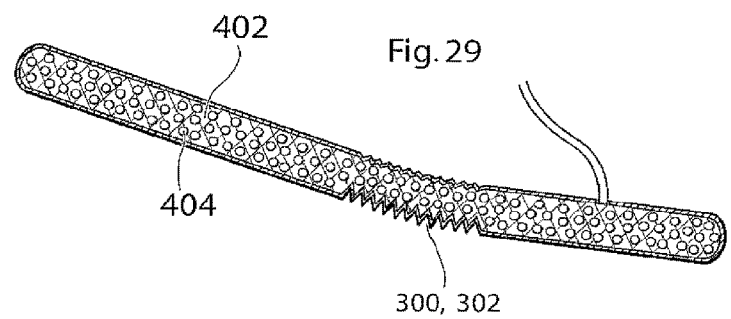
Figure 30:
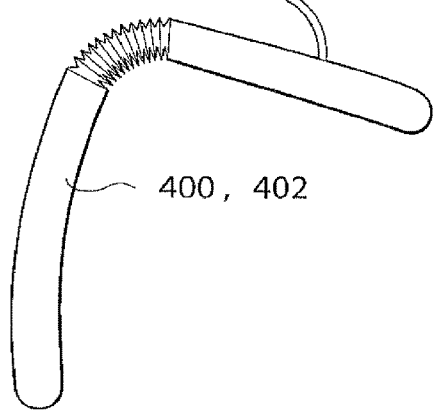
Figure 31:
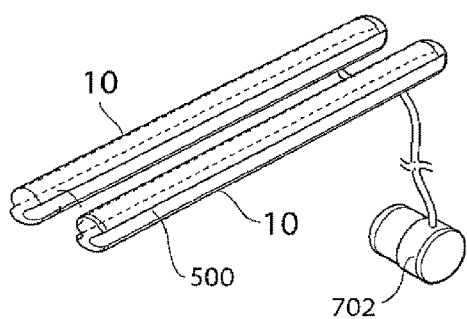
Figure 31:
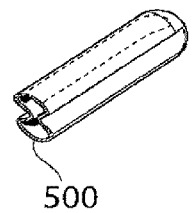
Figure 31:
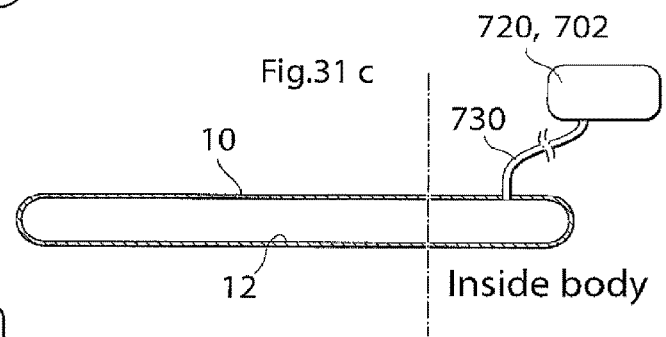
Figure 31:
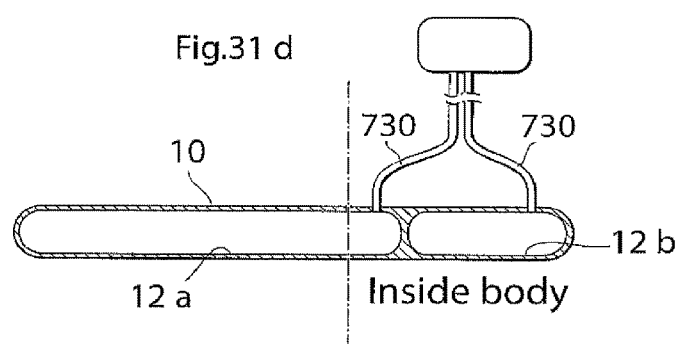

In FIGS. 27-30 a penile implant 10 is shown which is hollow or comprises a hollow body 12, 12a, 12b and where the penile implant 10 or hollow body 12, 12a, 12b at least partly is filled with a foam material 400, 402. The hollow body is illustrated in FIGS. 31c, 31d. In FIG. 28 the foam material 400 is illustrated by the cross hatched area. As shown in FIG. 29, a foam material 402 comprising closed spaces or compartments 404 which contain a gas, e.g. air may also be used. Such a foam material 402 is very light which is an advantage as discussed in the summary. In general, suitably the foam material 400, 402 is of the closed cellular type. In FIGS. 28 and 29 the penile implant 10 is in an activated state. In FIG. 30 a penile implant 10 as in FIGS. 28 and 29 is shown in a relaxed state. The penile implant 10 in FIGS. 28-30 comprises a bending portion 300, 302 but the penile implant 10 may of course comprise a foam material 400, 402 without having a bending portion 300, 302.

Radial and Longitudinal Expansion

Figure 32:
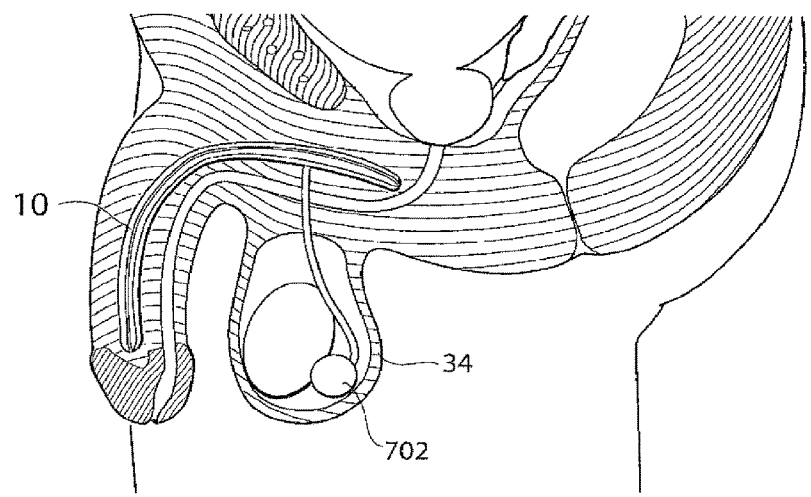
Figure 33:
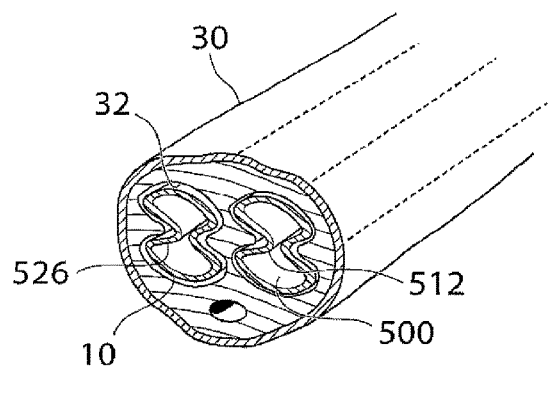
Figure 33:
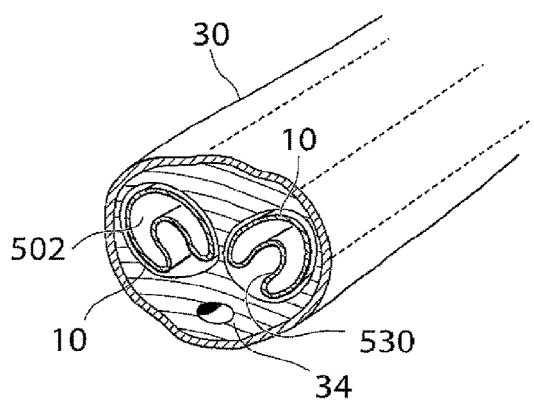
Figure 33:
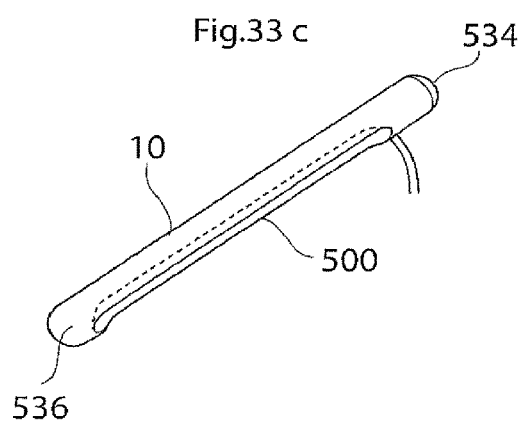
Figure 33:
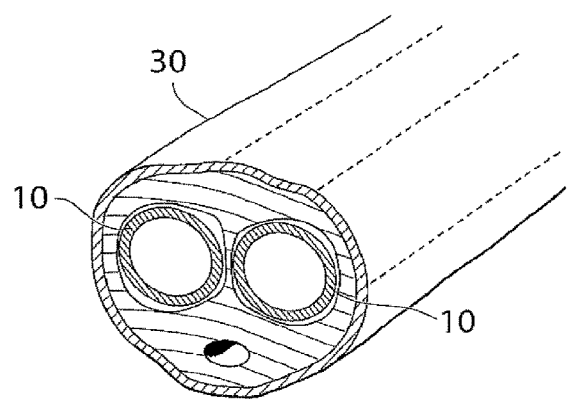
Figure 33:
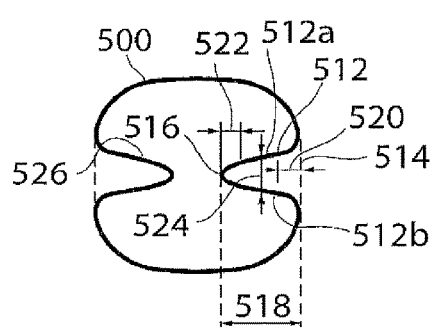
Figure 34:
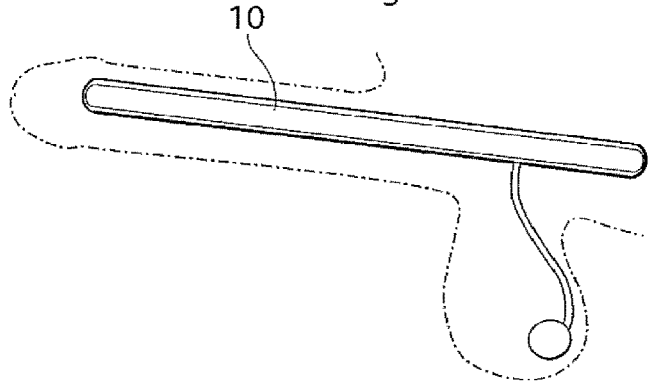

In FIGS. 31-37 and 40-42 a penile implant 10 having a radially expandable portion 500, 502 and/or a longitudinally expandable portion 504 is illustrated. In FIG. 31a two penile implants 10 coupled to a manual operation device 702 are shown. Suitably one penile implant 10 is implanted in each corpus cavernosum. Generally and in any embodiment, if the penile implant 10 is activated by a pressurized fluid suitably the penile implant 10 is at least partly hollow or at least partly comprises a hollow body 12, 12a, 12b, where the penile implant 10 or the hollow body 12, 12a, 12b is adapted to be filled and pressurized with a fluid. In FIGS. 31c, 31d the hollow body 12, 12a, 12b is shown in two embodiments, one where the penile implant 10 comprises one hollow body 12 and another where the penile implant 10 comprises two hollow bodies 12a, 12b. The hollow bodies 12, 12a, 12b or the penile implant 10 are/is suitably connected to an operation device 720, 702 by a conduit 730 adapted to convey fluid. In FIG. 32 a penile implant 10 implanted in the corpus cavernosum of a penis and connected by a conduit 730 to an operation device 702 implanted in the scrotum 34 is shown in its relaxed state. The radially expandable portion 500, 502 may e.g. be waist formed and comprise two indentations 512, 526 as shown in FIGS. 33a, 33e or comprise one indentation 530 as in FIG. 33b and may extend along substantially the complete length of the penile implant 10. In FIG. 33c a penile implant 10 is shown where the radially expandable portion 500, 502 extends along a part of the length of the penile implant 10. The radially expandable portion 500, 502 may e.g. extend from a point at approximately 2 or 3 cm distance from the proximal end 534 to a point at approximately 1 cm distance from the distal end 536 of the penile implant 10. FIG. 34 schematically shows the penile implant 10 in FIG. 32 in an expanded state. FIG. 33a shows a cross section of a penis 30 where a penile implant 10 is implanted in each corpus cavemosum, and has a radially expandable portion 500 comprising two indentations 512, 526. The penile implants 10 are in their collapsed state in FIG. 33a. Reference number 32 denotes the envelope of fibrous tissue that surrounds each corpus cavemosum. FIG. 33d shows the penile implants 10 in FIGS. 33a, 33b in an expanded state. FIG. 33b shows a cross section of a penis 30 where a penile implant 10 having a radially expandable portion 502 is implanted in each corpus cavernosum and is in its collapsed state. The radially expandable portion 502 comprises one indentation 530 which faces the urethra 34. FIG. 33e shows the distance 524 between the substantially opposing sides 512a and 512b of the indentation 512 and the depth 518 of the indentation or concaveness 512. As for the surface structure 100, the distance 524 may be measured within an interval 520 from the top or opening 514 of the indentation 512 and/or within an interval 522 from the bottom 516 of the indentation 512. This is analogous with the definition of the distances 108a, 108b, 118a, 118b. The distance 524 may e.g. be around 3 mm and it is suitable that this means that the distance 524 should be around 3 mm at some level within the interval 522 and at some level within the interval 520. What has been stated about distance and depth for the indentation 512 is also valid for the indentations 526 and 530.

Figure 35:
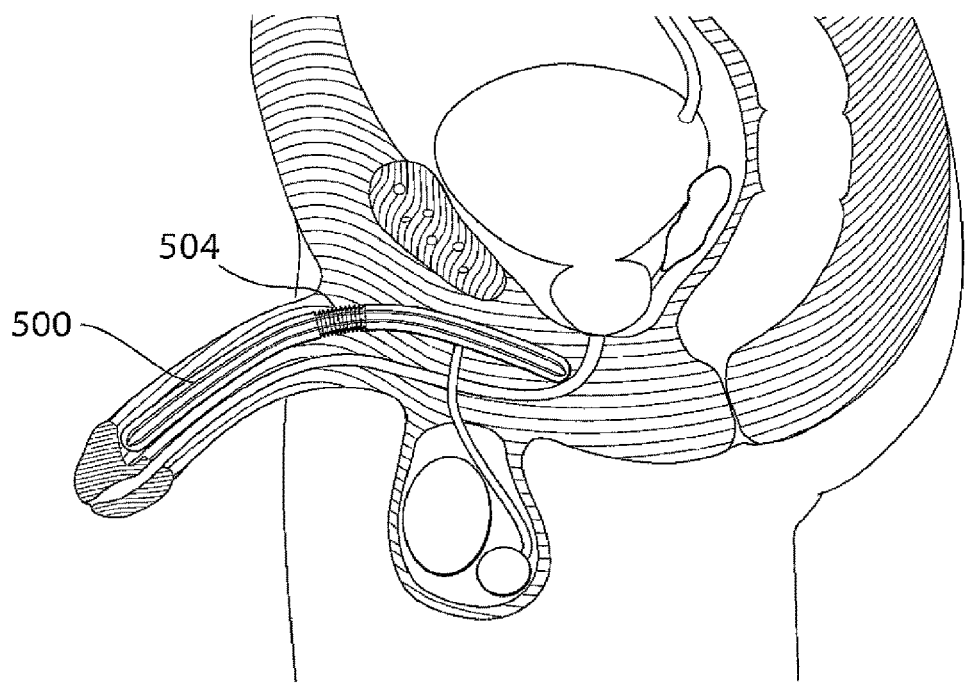
Figure 36:
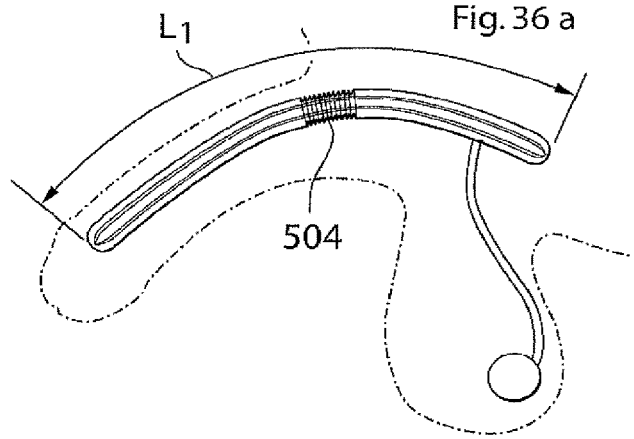
Figure 36:
Figure 37:
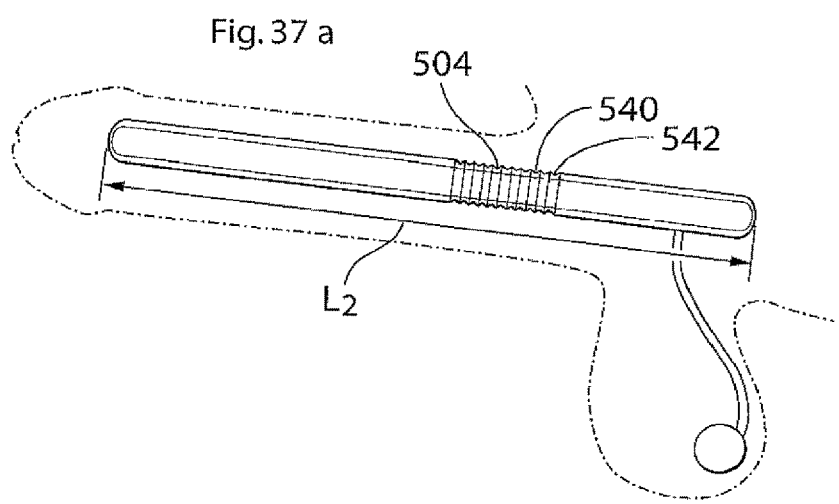
Figure 37:
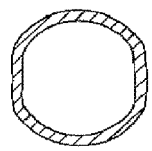

FIG. 35 shows a penile implant 10 having a radially expandable portion 500, 502 and a longitudinally expandable portion 504. The longitudinally expandable portion 504 is located in the area where the proximal portion 10e and distal portion 10d of the penile implant 10 meet, which is one suitable location. In FIGS. 36a, 36b and 37a, 37b the penile implant 10 in FIG. 35 is shown in a collapsed respectively in an expanded state.

In FIGS. 40, 41 an embodiment is shown where the penile implant 10 comprises a hollow part adapted to be filled and pressurized with a fluid, the hollow part may be realized in that the penile implant 10 itself is hollow or it may comprise a hollow body 12, 12a, 12b. The hollow part 10, 12, 12a, 12b is divided in compartments 560, 562 separated by dividing wall(s) 566 having a valve 568 which at a first side A opens for fluid flow from the first side A when the fluid pressure at the first side A exceeds a certain pressure value but otherwise is closed for fluid flow from the first side A. At the second side B of the valve 568 the valve opens for fluid flow from the second side B already when the fluid pressure at the second side is very low, suitably at substantially zero pressure, this to enable emptying compartment 562 and collapsing invagination 564. The compartment 562 on the second side B of the wall 566 has at least one invagination 564. Line 564i shows the invagination 564 in its invaginated or collapsed form and line 564ii in its expanded form. In this way a first compartment 560 on the first side A of a dividing wall 566 can be filled and pressurized with fluid to make the implant 10 hard and stiff at a first size, and by further increasing the pressure of the fluid a second compartment 562 on the second side B of the dividing wall 566 can be filled and pressurized with fluid to make the implant 10 hard and stiff at a second, greater size when the invagination 564 bulge due to the fluid pressure. Suitably the first compartment 560 is adapted to always be filled and pressurized with fluid when the implant 10 is activated. Suitably the penile implant 10 is activated in that the operation device 702, 722 is controlled to fill and pressurize the first compartment 560 with fluid to a first pressure level, where the patient or user of the system can select to increase the pressure to fill and pressurize also the second compartment 562 to achieve a larger erected penis. The part of the penile implant 10 or hollow body 12, 12a, 12b that comprises the first compartment 560 may as well comprise a radially and/or longitudinally expandable portion 500, 502, 504 or any other feature or aspect described herein. Wall part 570 is optional. FIG. 40 shows a longitudinally expandable portion 574 having a compartment 562 for longitudinal expansion and FIG. 41 two compartments 562a, 562b for radial expansion having two radially expandable segments 572a, 572b. The invagination 564 in FIG. 41 may e.g. be an indentation 512, 526, or 530. Instead of two compartments 562a, 562b for radial expansion there may be provided one compartment 562 for radial expansion having one radially expandable segment 572, suitable e.g. if the penile implant 10 or hollow body 12, 12a, 12b has a cross section presenting an indentation 530 as shown in FIG. 33b.

The radially expandable segment(s) 572, 572a, 572b may be adapted to assume any desired radial dimension when the compartment(s) 562, 562a, 562b are filled with and pressurized by fluid. One example of a radial dimension of the radially expandable segment(s) 572, 572a, 572b in the expanded state is illustrated by the continuous lines indicated by 572a, 572b. Another example is illustrated by the broken lines indicated by 576a, 576b and illustrating another radial dimension of the radially expandable segment(s) 572, 572a, 572b. The radially expandable segment(s) 572, 572a, 572b may extend along a part of or along the whole distal portion of the penile implant 10. If desired, the radially expandable segment(s) 572, 572a, 572b may also extend along the proximal portion of the penile implant. The compartment 562 and invagination 564 in FIG. 40 may have any desired size or length to achieve any desired prolongation of the penile implant 10 when the compartment 562 is filled with and pressurized by fluid. Hence, to achieve any desired prolongation of the penis 30 when the penile implant 10 is implanted in a corpus cavernosum of the penis 30 and the compartment 562 is filled with and pressurized by fluid. Correspondingly, the size of the radially expandable segment(s) 572, 572a, 572b may be adapted to achieve any desired radial expansion of the penis 30.

In FIG. 42 an embodiment is shown where the penile implant 10 or hollow body 12, 12a, 12b is divided in a first hollow portion 584 and a second hollow portion 586 connected by a flexible conduit, e.g. one flexible conduit 580a or two flexible conduits 580a, 580b, and a flexible portion 582. Each hollow portion 584, 586 has an invagination 564a, 564b where the invaginations 564a, 564b arc facing each other and are adapted to bulge and mutually exert a force on each other when subjected to fluid pressure, so as to prolong the penile implant 10 and/or hollow body 12, 12a, 12b when the first and second hollow portions 584, 586 are filled and pressurized with a fluid, wherein the invaginations 564a, 564b are adapted to resume their invaginated or collapsed form when the fluid pressure is removed so that the penile implant 10 and/or hollow body 12, 12a, 12b resumes its not prolonged length. When the penile implant 10 is activated and the hollow portions 584, 586 are filled and pressurized with the fluid pumped by the operation device 702, 722 the flexible conduits 580a, 580b, and the flexible portion 582 naturally also prolong. The embodiments in FIGS. 40-42 may naturally be combined in any way.

Vibrating Unit

Figure 38:
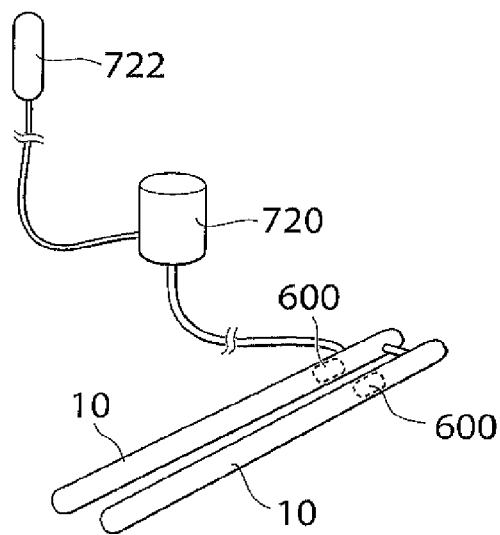
FIG. 38a schematically show a vibration device with an operably connected implantable device.
FIG. 38b schematically shows an embodiment of a vibration device.
FIG. 38c schematically shows an embodiment of a vibration device with an electromagnetic device.
Figure 38:
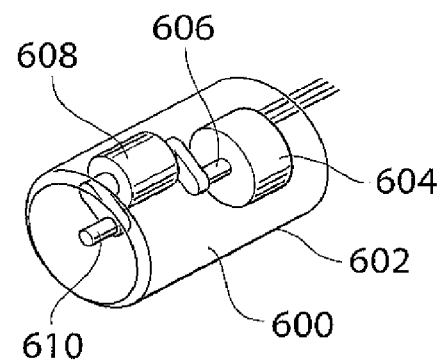
Figure 38:
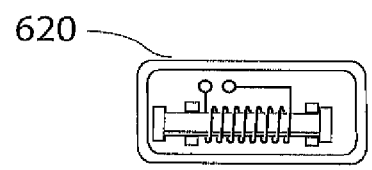
Figure 39:
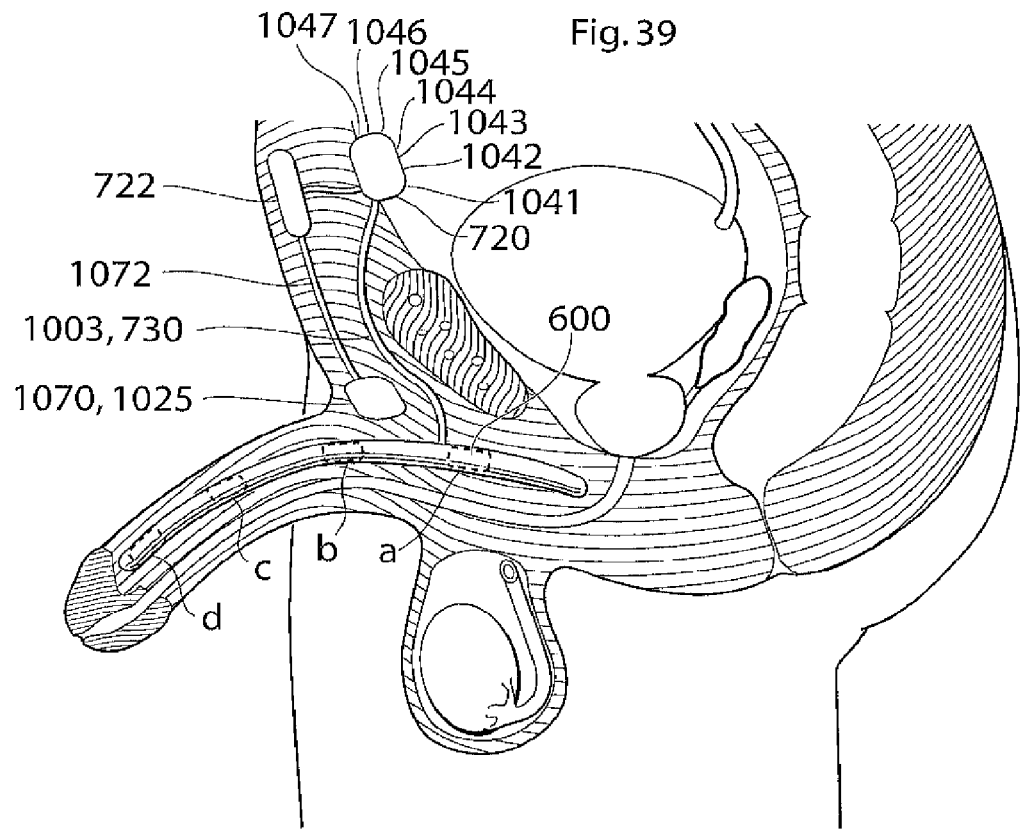
FIG. 39 schematically shows an operably connected penile implant with a vibration device.

In FIGS. 38-39 a vibration device 600 and a penile implant 10 comprising such a device is shown. FIG. 38a shows one exemplary location of a vibration device 600 in each penile implant 10 of a penile prosthesis system 700. FIG. 38b schematically shows one exemplary embodiment of the vibration device 600 comprising an outer shell 602, a motor 604, a first motor axis 606, an eccentric element 608 eccentrically mounted to the first motor axis 606, a second axis 610 which suitably is supported by a bearing mounted to the outer shell 602. FIG. 39 shows a penile implant 10 having a vibration device 600, implanted in the corpus cavernosum of a penis and connected by a fluid conduit 730 to an operation device 720 and to a control device 722 in its relaxed state. In FIG. 39 letters a, b, c and d indicates alternative locations for the vibration device 600. The vibration device 600 may of course be implanted directly in the penis or in the region of the penis and need not be located in a penile implant 10. FIG. 38c schematically shows one exemplary embodiment of the vibration device 600 comprising an electromagnetic device 620.

Generally, in any embodiment of the penile implant 10 or vibration device 600, a sensor 1070, 1025, 1043 may measure at least one physiological or functional parameter. The location of the sensor 1070, 1025 is adapted to the circumstances, e.g. which parameter that should be measured. The sensor 1070, 1025 may e.g. be connected to the control device 722 via a communication line 1072 that also may supply power to the sensor 1070, 1025.

The control device 722 or operation device 720 may comprise at least one item selected from the group consisting of; an energy-transforming device 1002, a control unit 1041, a battery 1042, a sensor 1043, a motor 1044, a pump 1045, a reservoir 1046 or an injection port 1047. The items being selected depending on the circumstances, e.g. if the apparatus is electrically, hydraulically, pneumatically or mechanically operated.

If a non-rechargeable battery is used the energy-transforming device 1002 may be omitted but the items 1041 to 1047 may be used as suitable, and be connected to the penile implant 10, vibration device 600 and sensor 1070, 1025, 1043 as suitable. If e.g. the penile implant 10 is hydraulically operated it may e.g. be suitable to use a control unit 1041, a pump 1045 and/or a reservoir 1046, the connection to the penile implant 10 suitably being a hydraulic conduit.

In general, any item, or combinations of items, described and suited therefore, may be connected to the penile implant 10 via the power supply line 1003, 730. The actual item, or combinations of items, being chosen depending on the circumstances, e.g. if the penile implant 10 is electrically, hydraulically, pneumatically or mechanically operated. This is valid for any embodiment of the penile implant 10 or vibration device 600, described in any figure.

If e.g. the penile implant 10 is mechanically operated it may be connected to a motor 1044 via the power supply line 1003, 730 which in this case may be a wire or bowden cable. A control unit 1041 may be connected to the motor 1044.

If e.g. the penile implant 10 is electrically operated it may be suitable to connect it to a source of electrical energy 1002 or 1042 via the power supply line 1003, 730 which in this case may be an electrical conduit. A control unit 1041 or control device 722 may be connected to the source of electrical energy 1002 or 1042.

System, e.g. A Penile Prosthesis System

Figure 1B:
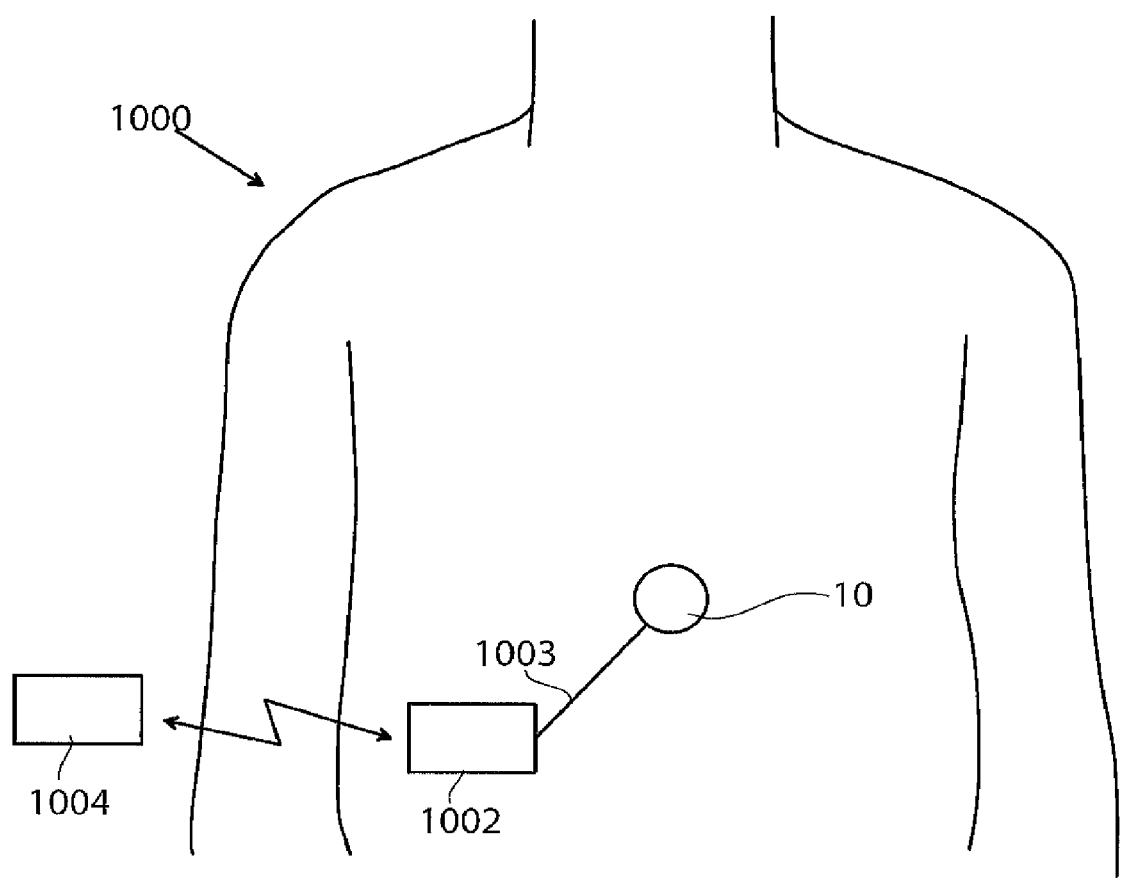
FIG. 1*b* illustrates a system for treating a disease, wherein the system includes an penile implant 10 of the invention implanted in a patient.

FIG. 1b schematicelly illustrates a system for treating a disease comprising an penile implant 10 of the present invention placed in a patient. An implanted energy-transforming device 1002 is adapted to supply energy consuming components of the penile implant with energy via a power supply line 1003. An external energy-transmission device 1004 for non-invasively energizing the penile implant 10 transmits energy by at least one wireless energy signal. The implanted energy-transforming device 1002 transforms energy from the wireless energy signal into electric energy which is supplied via the power supply line 1003.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted penile implant 10 is operable in response to the energy of the second form. The energy-transforming device 1002 may directly power the penile implant with the second form energy, as the energy-transforming device 1002 transforms the first form energy transmitted by the energy-transmission device 1004 into the second form energy. The system may further include an implantable accumulator, wherein the second form energy is used at least partly to charge the accumulator.

Alternatively, the wireless energy transmitted by the energy-transmission device 1004 may be used to directly power the penile implant, as the wireless energy is being transmitted by the energy-transmission device 1004. Where the system comprises an operation device for operating the penile implant, as will be described below, the wireless energy transmitted by the energy-transmission device 1004 may be used to directly power the operation device to create kinetic energy for the operation of the penile implant.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the penile implant comprises electric components that are energized with electrical energy. Other implantable electric components of the system may be at least one voltage level guard or at least one constant current guard connected with the electric components of the penile implant. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal. The energy-transmission device may be controlled from outside the patient's body to release electromagnetic wireless energy, and the released electromagnetic wireless energy is used for operating the penile implant. Alternatively, the energy-transmission device is controlled from outside the patient's body to release non-magnetic wireless energy, and the released non-magnetic wireless energy is used for operating the penile implant.

The external energy-transmission device 1004 also includes a wireless remote control having an external signal transmitter for transmitting a wireless control signal for non-invasively controlling the penile implant. The control signal is received by an implanted signal receiver which may be incorporated in the implanted energy-transforming device 1002 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 43 illustrates the system of FIG. 1b in the form of a more generalized block diagram showing the penile implant 10, the energy-transforming device 1002 powering the penile implant 10 via power supply line 1003, and the external energy-transmission device 1004, The patient's skin 1005, generally shown by a vertical line, separates the interior of the patient to the right of the line from the exterior to the left of the line. FIG. 42 shows an embodiment of the invention identical to that of FIG. 43, except that a reversing device in the form of an electric switch 1006 operable for example by polarized energy also is implanted in the patient for reversing the penile implant 10. When the switch is operated by polarized energy the wireless remote control of the external energy-transmission device 1004 transmits a wireless signal that carries polarized energy and the implanted energy-transforming device 1002 transforms the wireless polarized energy into a polarized current for operating the electric switch 1006. When the polarity of the current is shifted by the implanted energy-transforming device 1002 the electric switch 1006 reverses the function performed by the penile implant 10.

FIG. 45 shows an embodiment of the invention identical to that of FIG. 43, except that an operation device 1007 implanted in the patient for operating the penile implant 10 is provided between the implanted energy-transforming device 1002 and the penile implant 10. This operation device can be in the form of a motor 1007, such as an electric servomotor. The motor 1007 is powered with energy from the implanted energy-transforming device 1002, as the remote control of the external energy-transmission device 1004 transmits a wireless signal to the receiver of the implanted energy-transforming device 1002.

FIG. 46 shows an embodiment of the invention identical to that of FIG. 43, except that it also comprises an operation device is in the form of an assembly 1008 including a motor/pump unit 1009 and a fluid reservoir 1010 is implanted in the patient. In this case the penile implant 10 is hydraulically operated, i.e. hydraulic fluid is pumped by the motor/pump unit 1009 from the fluid reservoir 1010 through a conduit 1011 to the penile implant 10 to operate the penile implant, and hydraulic fluid is pumped by the motor/pump unit 1009 back from the penile implant 10 to the fluid reservoir 1010 to return the penile implant to a starting position. The implanted energy-transforming device 1002 transforms wireless energy into a current, for example a polarized current, for powering the motor/pump unit 1009 via an electric power supply line 1012. Instead of a hydraulically operated penile implant 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 1002 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 47:
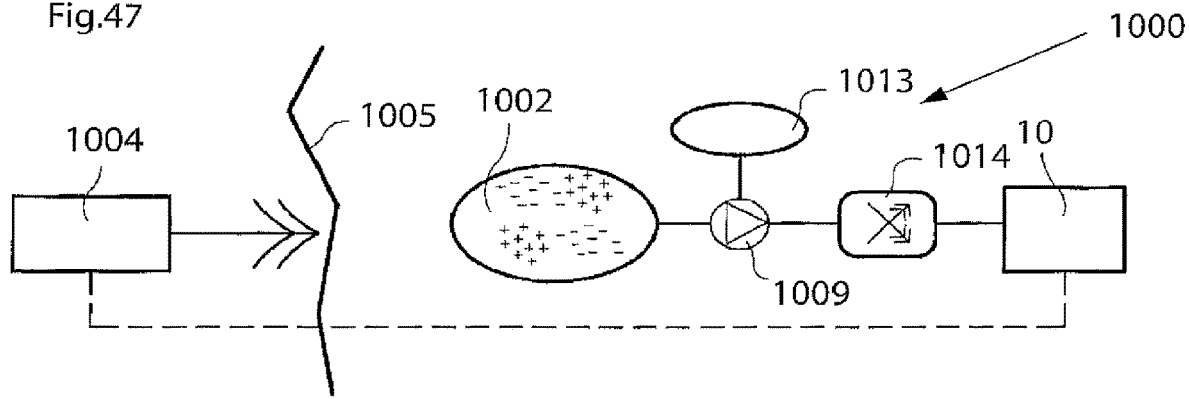

FIG. 47 shows an embodiment of the invention comprising the external energy-transmission device 1004 with its wireless remote control, the penile implant 10, in this case hydraulically operated, and the implanted energy-transforming device 1002, and further comprising a hydraulic fluid reservoir 1013, a motor/pump unit 1009 and a reversing device in the form of a hydraulic valve shifting device 1014, all implanted in the patient. Of course the hydraulic operation could easily be performed by just changing the pumping direction and the hydraulic valve may therefore be omitted.

Figure 48:
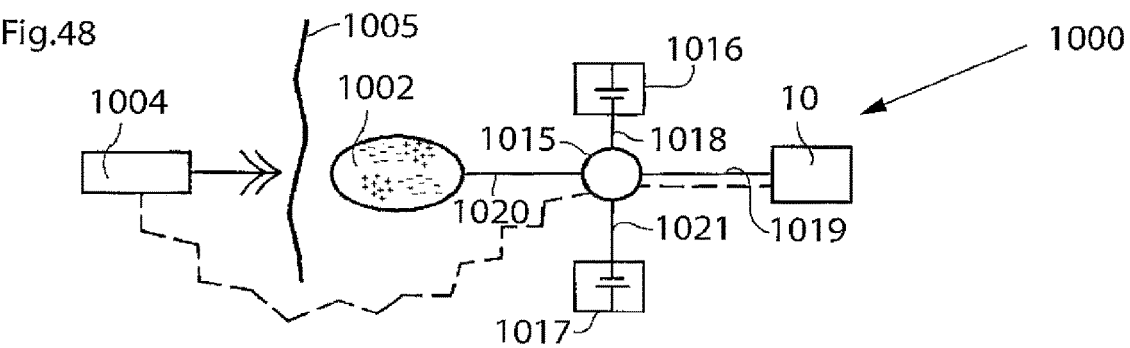

The remote control may be a device separated from the external energy-transmission device or included in the same. The motor of the motor/pump unit 1009 is an electric motor. In response to a control signal from the wireless remote control of the external energy-transmission device 1004, the implanted energy-transforming device 1002 powers the motor/pump unit 1009 with energy from the energy carried by the control signal, whereby the motor/pump unit 1009 distributes hydraulic fluid between the hydraulic fluid reservoir 1013 and the penile implant 10. The remote control of the external energy-transmission device 1004 controls the hydraulic valve shifting device 1014 to shift the hydraulic fluid flow direction between one direction in which the fluid is pumped by the motor/pump unit 1009 from the hydraulic fluid reservoir 1013 to the penile implant 10 to operate the penile implant, and another opposite direction in which the fluid is pumped by the motor/pump unit 1009 back from the penile implant 10 to the hydraulic fluid reservoir 1013 to return the penile implant to a starting position. FIG. 48 shows an embodiment of the invention comprising the external energy-transmission device 1004 with its wireless remote control, the penile implant 10, the implanted energy-transforming device 1002, an implanted internal control unit 1015 controlled by the wireless remote control of the external energy-transmission device 1004, an implanted accumulator 1016 and an implanted capacitor 1017. The internal control unit 1015 arranges storage of electric energy received from the implanted energy-transforming device 1002 in the accumulator 1016, which supplies energy to the penile implant 10. In response to a control signal from the wireless remote control of the external energy-transmission device 1004, the internal control unit 1015 either releases electric energy from the accumulator 1016 and transfers the released energy via power lines 1018 and 1019, or directly transfers electric energy from the implanted energy-transforming device 1002 via a power line 1020, the capacitor 1017, which stabilizes the electric current, a power line 1021 and the power line 1019, for the operation of the penile implant 10.

The internal control unit is preferably programmable from outside the patient's body. In a preferred embodiment, the internal control unit is programmed to regulate the penile implant 10 according to a pre-programmed time-schedule or to input from any sensor sensing any possible physical parameter of the patient or any functional parameter of the system.

In accordance with an alternative, the capacitor 1017 in the embodiment of FIG. 48 10 may be omitted. In accordance with another alternative, the accumulator 1016 in this embodiment may be omitted.

Figure 49:
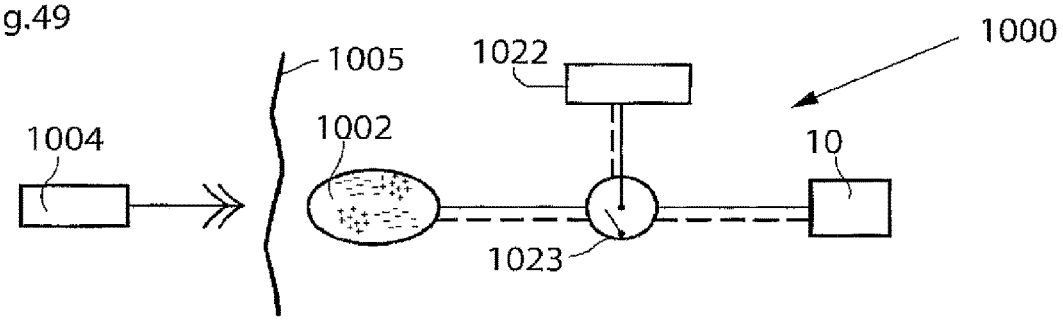

FIG. 49 shows an embodiment of the invention identical to that of FIG. 43, except that a battery 1022 for supplying energy for the operation of the penile implant 10 and an electric switch 1023 for switching the operation of the penile implant 10 also are implanted in the patient. The electric switch 1023 may be controlled by the remote control and may also be operated by the energy supplied by the implanted energy-transforming device 1002 to switch from an off mode, in which the battery 1022 is not in use, to an on mode, in which the battery 1022 supplies energy for the operation of the penile implant 10.

Figure 50:
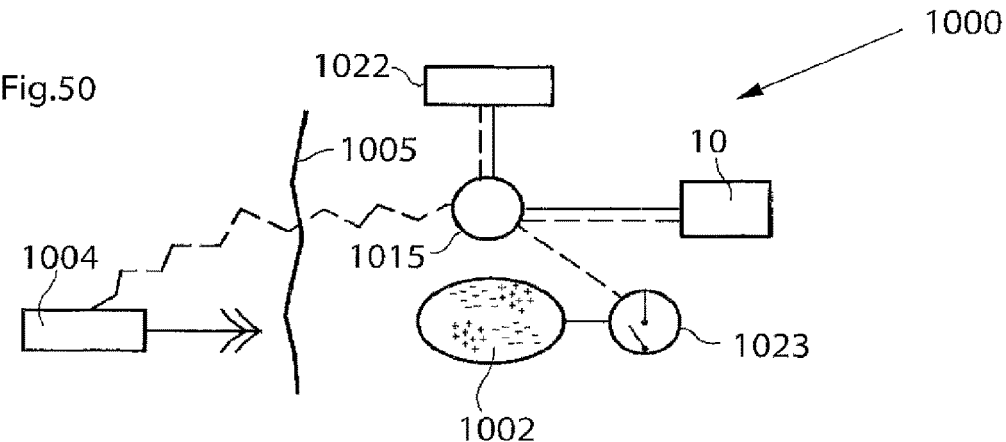

FIG. 50 shows an embodiment of the invention identical to that of FIG. 49, except that an internal control unit 1015 controllable by the wireless remote control of the external energy-transmission device 1004 also is implanted in the patient. In this case, the electric switch 1023 is operated by the energy supplied by the implanted energy-transforming device 1002 to switch from an off mode, in which the wireless remote control is prevented from controlling the internal control unit 1015 and the battery is not in use, to a standby mode, in which the remote control is permitted to control the internal control unit 1015 to release electric energy from the battery 1022 for the operation of the penile implant 10.

Figure 51:
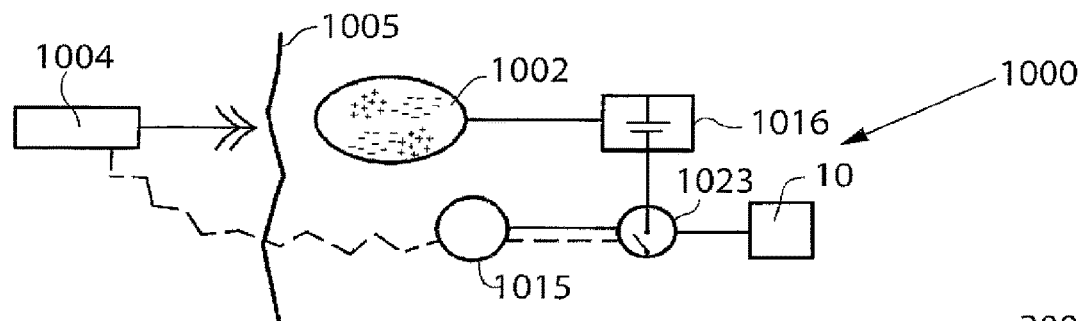

FIG. 51 shows an embodiment of the invention identical to that of FIG. 50, except that an accumulator 1016 is substituted for the battery 1022 and the implanted components are interconnected differently. In this case, the accumulator 1016 stores energy from the implanted energy-transforming device 1002. In response to a control signal from the wireless remote control of the external energy-transmission device 1004, the internal control unit 1015 controls the electric switch 1023 to switch from an off mode, in which the accumulator 1016 is not in use, to an on mode, in which the accumulator 1016 supplies energy for the operation of the penile implant 10. The accumulator may be combined with or replaced by a capacitor.

Figure 52:
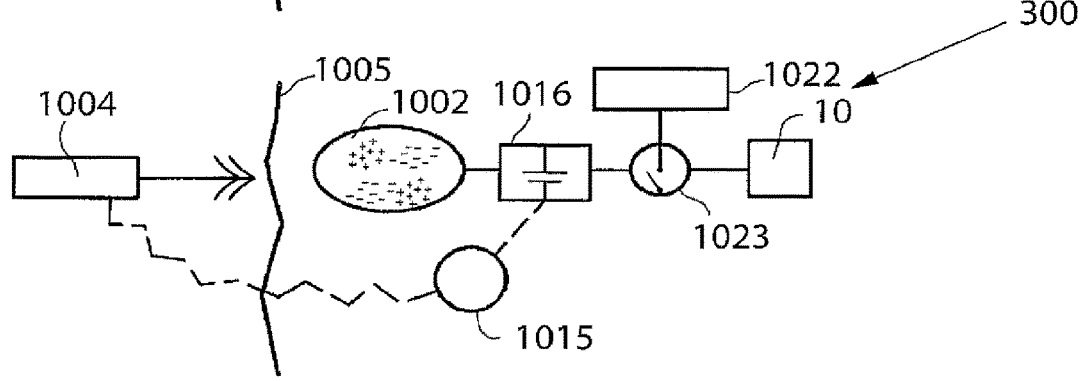

FIG. 52 shows an embodiment of the invention identical to that of FIG. 51, except that a battery 1022 also is implanted in the patient and the implanted components are interconnected differently. In response to a control signal from the wireless remote control of the external energy-transmission device 1004, the internal control unit 1015 controls the accumulator 1016 to deliver energy for operating the electric switch 1023 to switch from an off mode, in which the battery 1022 is not in use, to an on mode, in which the battery 1022 supplies electric energy for the operation of the penile implant 10.

Alternatively, the electric switch 1023 may be operated by energy supplied by the accumulator 1016 to switch from an off mode, in which the wireless remote control is prevented from controlling the battery 1022 to supply electric energy and is not in use, to a standby mode, in which the wireless remote control is permitted to control the battery 1022 to supply electric energy for the operation of the penile implant 10. It should be understood that the switch 1023 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 53:
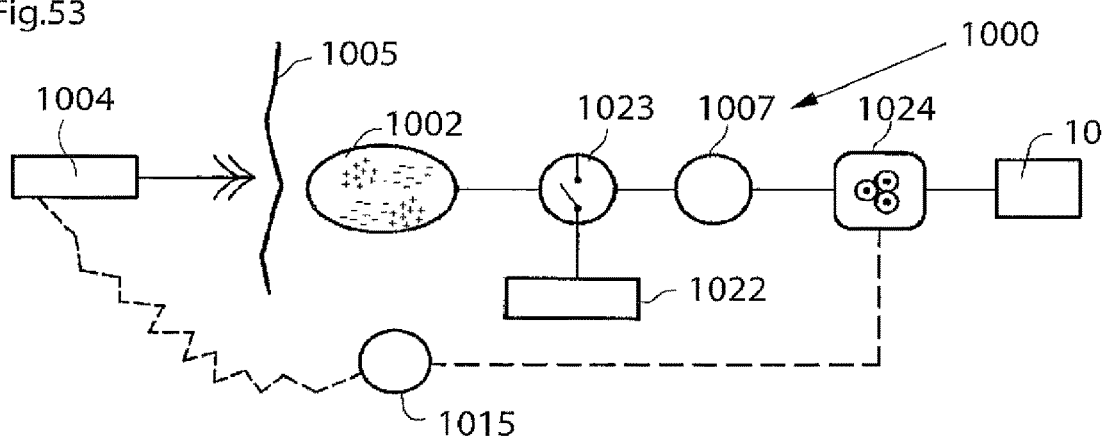

FIG. 53 shows an embodiment of the invention identical to that of FIG. 49, except that a motor 1007, a mechanical reversing device in the form of a gear box 1024, and an internal control unit 1015 for controlling the gear box 1024 also are implanted in the patient. The internal control unit 1015 controls the gear box 1024 to reverse the function performed by the penile implant 10 (mechanically operated). Even simpler is to switch the direction of the motor electronically. The gear box interpreted in its broadest embodiment may stand for a servo arrangement saving force for the operation device in favour of longer stroke to act.

Figure 54:
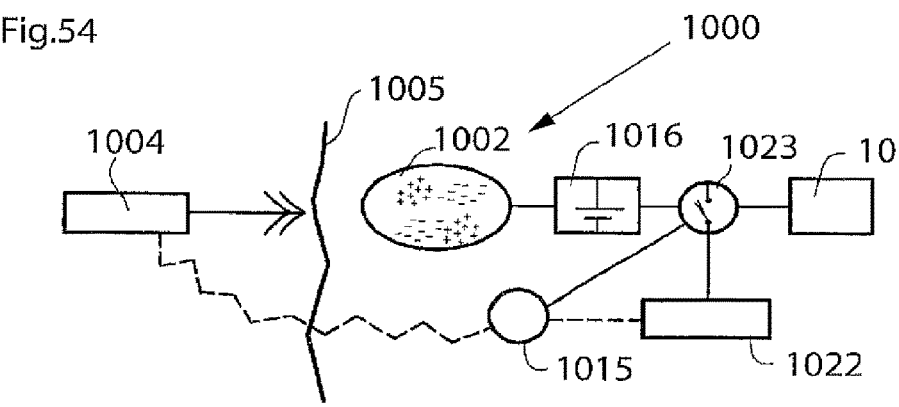
Figure 60:
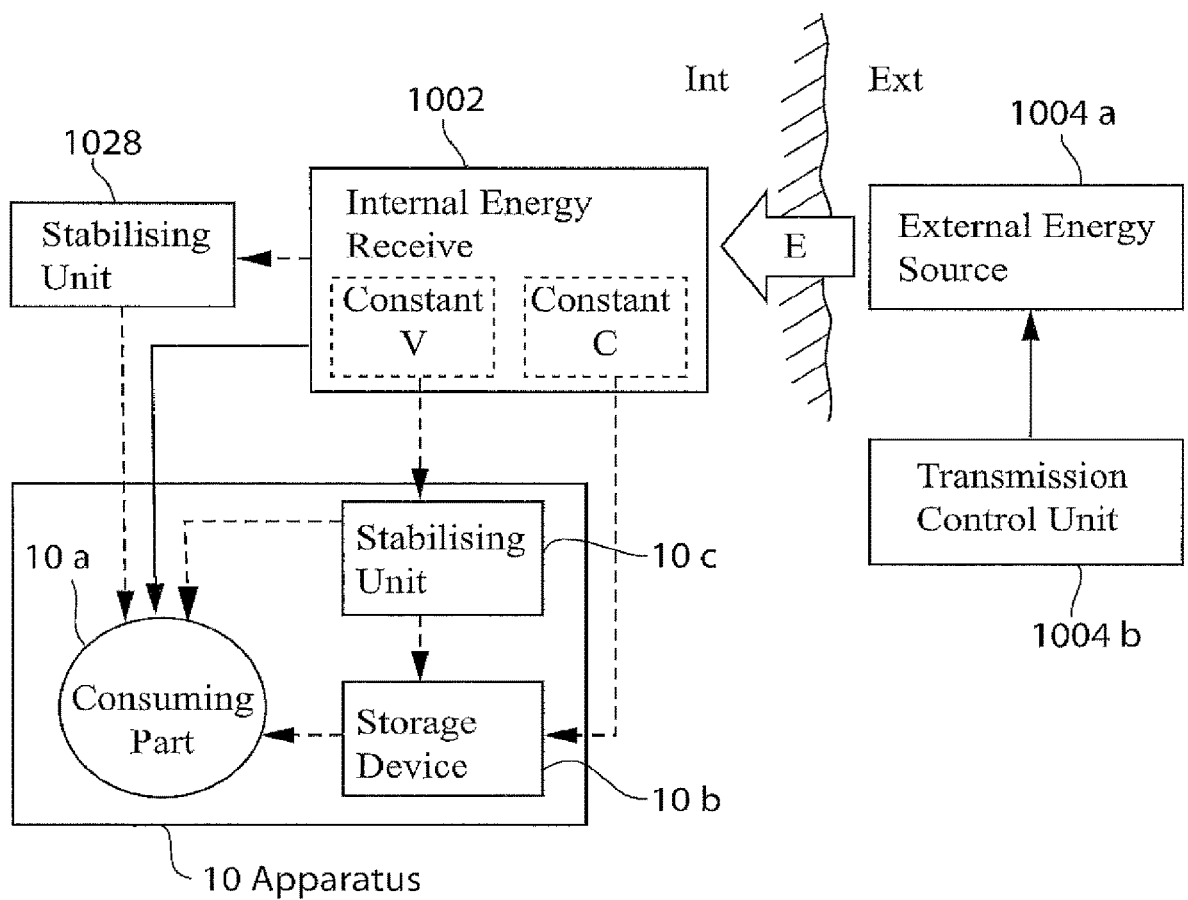
FIG. 60 is a more detailed block diagram of an arrangement for controlling the transmission of wireless energy used for the operation of the penile implant shown in FIG. 1b.

FIG. 54 shows an embodiment of the invention identical to that of FIG. 60 except that the implanted components are interconnected differently. Thus, in this case the internal control unit 1015 is powered by the battery 1022 when the accumulator 1016, suitably a capacitor, activates the electric switch 1023 to switch to an on mode. When the electric switch 1023 is in its on mode the internal control unit 1015 is permitted to control the battery 1022 to supply, or not supply, energy for the operation of the penile implant 10.

Figure 55:
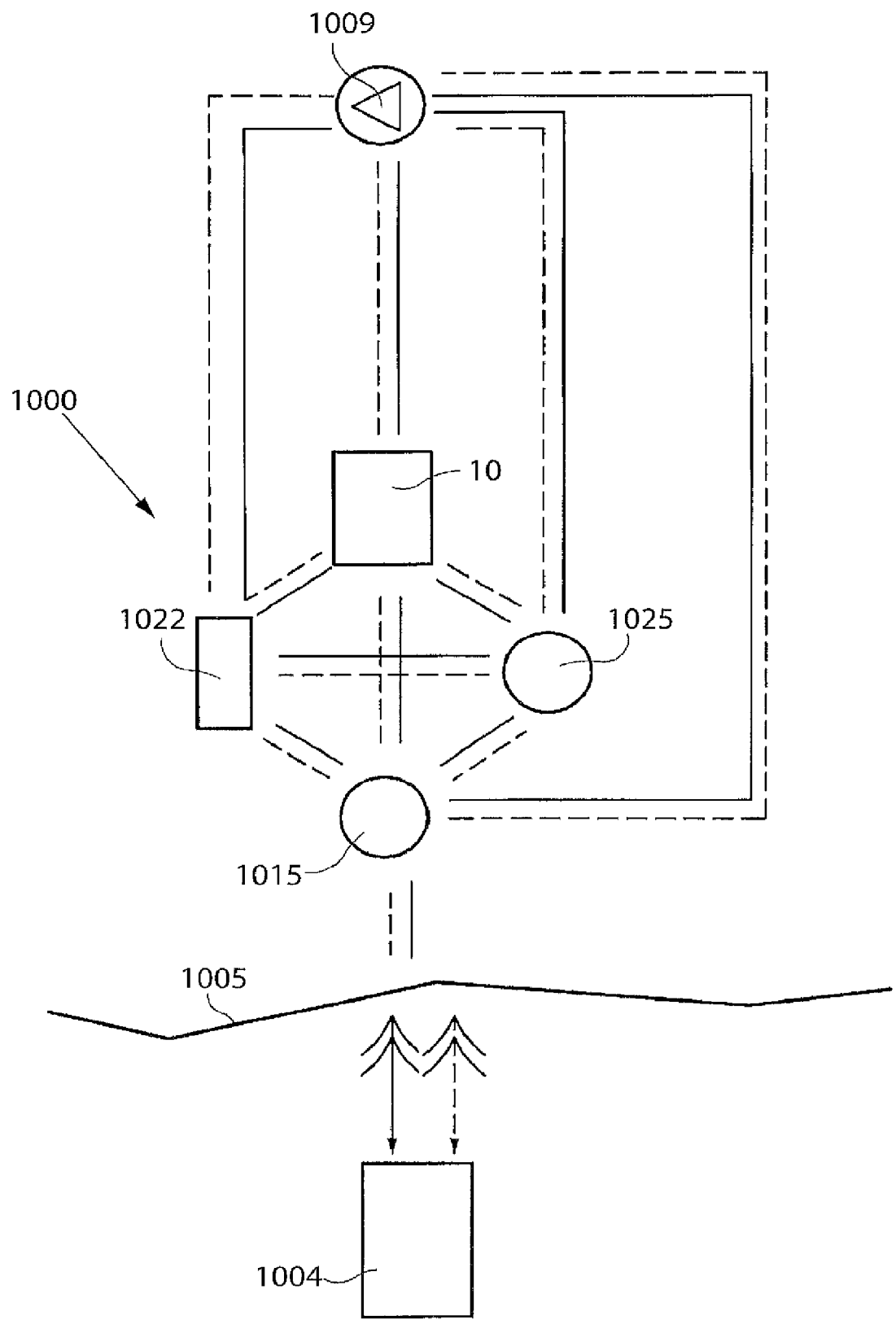

FIG. 55 schematically shows conceivable combinations of implanted components of the penile implant for achieving various communication options. Basically, there are the penile implant 10, the internal control unit 1015, motor or pump unit 1009, and the external energy-transmission device 1004 including the external wireless remote control. As already described above the wireless remote control transmits a control signal which is received by the internal control unit 1015, which in turn controls the various implanted components of the penile implant.

A feedback device, preferably comprising a sensor or measuring device 1025, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 1025 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretc, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 1015, or alternatively the external wireless remote control of the external energy-transmission device 1004, may control the penile implant 10 in response to signals from the sensor 1025. A transceiver may be combined with the sensor 1025 for sending information on the sensed physical parameter to the external wireless remote control. The wireless remote control may comprise a signal transmitter or transceiver and the internal control unit 1015 may comprise a signal receiver or transceiver. Alternatively, the wireless remote control may comprise a signal receiver or transceiver and the internal control unit 1015 may comprise a signal transmitter or transceiver. The above transceivers, transmitters and receivers may be used for sending information or data related to the penile implant 10 from inside the patient's body to the outside thereof.

Where the motor/pump unit 1009 and battery 1022 for powering the motor/pump unit 1009 are implanted, information related to the charging of the battery 1022 may be fed back. To be more precise, when charging a battery or accumulator with energy feed back information related to said charging process is sent and the energy supply is changed accordingly.

Figure 56:
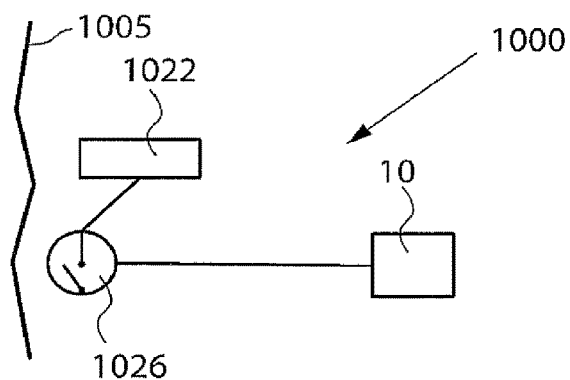

FIG. 56 shows an alternative embodiment wherein the penile implant 10 is regulated from outside the patient's body. The system 1000 comprises a battery 1022 connected to the penile implant 10 via a subcutaneous electric switch 1026. Thus, the regulation of the penile implant 10 is performed non-invasively by manually pressing the subcutaneous switch, whereby the operation of the penile implant 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 57:
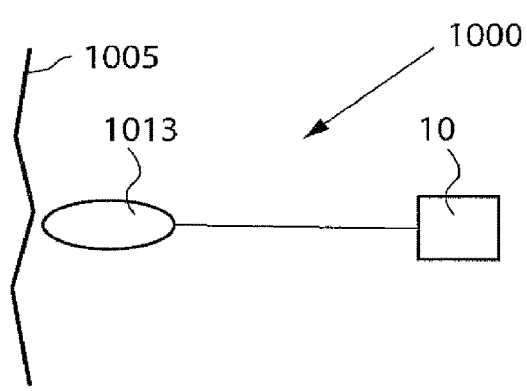

FIG. 57 shows an alternative embodiment, wherein the system 1000 comprises a hydraulic fluid reservoir 1013 hydraulically connected to the penile implant. Non-invasive regulation is performed by manually pressing the hydraulic reservoir connected to the penile implant.

The system may include an external data communicator and an implantable internal data communicator communicating with the external data communicator. The internal communicator feeds data related to the penile implant or the patient to the external data communicator and/or the external data communicator feeds data to the internal data communicator.

Figure 58:
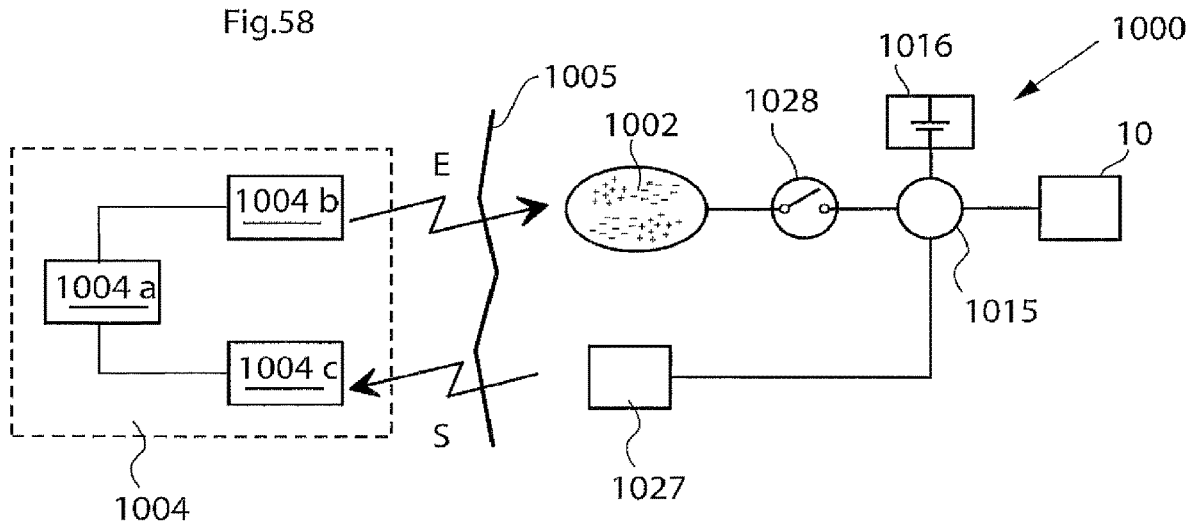
FIG. 58 is a schematic block diagram illustrating an arrangement for supplying an accurate amount of energy used for the operation of the penile implant shown in FIG. 1b.

FIG. 58 schematically illustrates an arrangement of the system that is capable of sending information from inside the patient's body to the outside thereof to give feedback information related to at least one functional parameter of the penile implant or system, or related to a physical parameter of the patient, in order to supply an accurate amount of energy to an implanted internal energy receiver 1002 connected to implanted energy consuming components of the penile implant 10. Such an energy receiver 1002 may include an energy source and/or an energy-transforming device. Briefly described, wireless energy is transmitted from an external energy source 1004a located outside the patient and is received by the internal energy receiver 1002 located inside the patient. The internal energy receiver is adapted to directly or indirectly supply received energy to the energy consuming components of the penile implant 10 via a switch 1026. An energy balance is determined between the energy received by the internal energy receiver 1002 and the energy used for the penile implant 10, and the transmission of wireless energy is then controlled based on the determined energy balance. The energy balance thus provides an accurate indication of the correct amount of energy needed, which is sufficient to operate the penile implant 10 properly, but without causing undue temperature rise.

In FIG. 58 the patient's skin is indicated by a vertical line 1005. Here, the energy receiver comprises an energy-transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from the external energy-source 1004a provided in an external energy-transmission device 1004 located outside the patient's skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming components of the penile implant, e.g. after storing the incoming energy in an implanted energy source, such as a rechargeable battery or a capacitor. However, the present invention is generally not limited to any particular energy transfer technique, TET devices or energy sources, and any kind of wireless energy may be used. The amount of energy received by the implanted energy receiver may be compared with the energy used by the implanted components of the penile implant. The term "energy used" is then understood to include also energy stored by implanted components of the penile implant. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between the switch 1026 and the penile implant 10. The internal control unit 1015 may thus be arranged to receive various measurements obtained by suitable sensors or the like, not shown, measuring certain characteristics of the penile implant 10, somehow reflecting the required amount of energy needed for proper operation of the penile implant 10. Moreover, the current condition of the patient may also be detected by means of suitable measuring devices or sensors, in order to provide parameters reflecting the patient's condition. Hence, such characteristics and/or parameters may be related to the current state of the penile implant 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the penile implant 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the penile implant 10, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the penile implant 10, or the patient, or an implanted energy source if used, or any combination thereof. The internal control unit 1015 is further connected to an internal signal transmitter 1027, arranged to transmit a control signal reflecting the determined required amount of energy, to an external signal receiver 1004c connected to the external control unit 1004b. The amount of energy transmitted from the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004b, thus integrating the above-described function of the internal control unit 1015 in the external control unit 1004b. In that case, the internal control unit 1015 can be omitted and the sensor measurements are supplied directly to the internal signal transmitter 1027 which sends the measurements over to the external signal receiver 1004c and the external control unit 1004b. The energy balance and the currently required amount of energy can then be determined by the external control unit 1004b based on those sensor measurements. Hence, the present solution according to the arrangement of FIG. 58 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the penile implant. The penile implant may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the penile implant.

The internal signal transmitter 1027 and the external signal receiver 1004c may be implemented as separate units using suitable signal transfer means, such as radio, IR (Infrared) or ultrasonic signals. Alternatively, the internal signal transmitter 1027 and the external signal receiver 1004c may be integrated in the implanted energy-transforming device 1002 and the external energy source 1004a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 58, the switch 1026 is either separate and controlled by the internal control unit 1015, or integrated in the internal control unit 1015. It should be understood that the switch 1026 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 58 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004c. Alternatively, the energy balance can be determined by the external control unit 1004b instead depending on the implementation, as mentioned above. In that case, the control signal may carry measurement results from various sensors. The amount of energy emitted from the external energy source 1004a can then be regulated by the external control unit 1004b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 59:
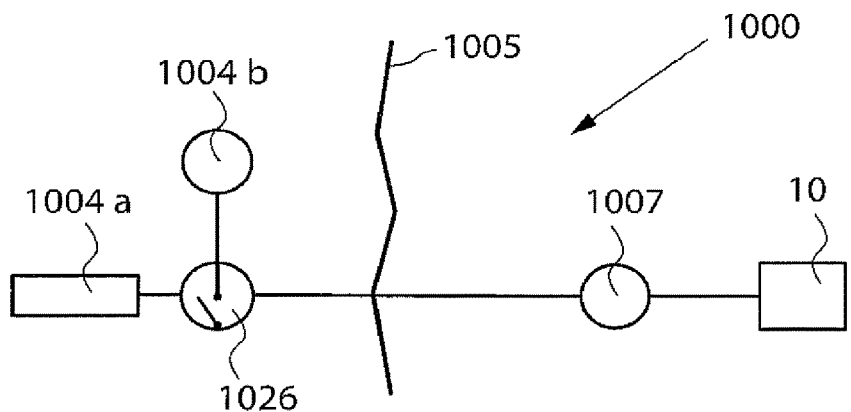
FIG. 59 schematically shows an embodiment of the system, in which the penile implant is operated with wire bound energy.

With reference to FIG. 59, although wireless transfer of energy for operating the penile implant has been described above to enable non-invasive operation, it will be appreciated that the penile implant can be operated with wire bound energy as well. Such an example is shown in FIG. 59, wherein an external switch 1026 is interconnected between the external energy source 1004*a* and an operation device, such as an electric motor 1007 operating the penile implant 10. An external control unit 1004*b* controls the operation of the external switch 1026 to effect proper operation of the penile implant 10.

FIG. 60 illustrates different embodiments for how received energy can be supplied to and used by the penile implant 10. Similar to the example of FIG. 58, an internal energy receiver 1002 receives wireless energy E from an external energy source 1004*a* which is controlled by a transmission control unit 1004*b*. The internal energy receiver 1002 may comprise a constant voltage circuit, indicated as a dashed box "constant V" in the figure, for supplying energy at constant voltage to the penile implant 10. The internal energy receiver 1002 may further comprise a constant current circuit, indicated as a dashed box "constant C" in the figure, for supplying energy at constant current to the penile implant 10.

The penile implant 10 comprises an energy consuming part 10*a*, which may be a motor, pump, restriction device, or any other medical appliance that requires energy for its electrical operation. The penile implant 10 may further comprise an energy storage device 10*b* for storing energy supplied from the internal energy receiver 1002. Thus, the supplied energy may be directly consumed by the energy consuming part 10*a*, or stored by the energy storage device 10*b*, or the supplied energy may be partly consumed and partly stored. The penile implant 10 may further comprise an energy stabilizing unit 10*c* for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the penile implant 10, before being consumed and/or stored by the penile implant 10. Alternatively, the energy stabilizing unit 1028 may be integrated in the internal energy receiver 1002. In either case, the energy stabilizing unit 1028 may comprise a constant voltage circuit and/or a constant current circuit.

It should be noted that FIG. 58 and FIG. 60 illustrate some possible but non-limiting implementation options regarding how the various shown functional components and elements can be arranged and connected to each other. However, the skilled person will readily appreciate that many variations and modifications can be made within the scope of the present invention.

Figure 61:
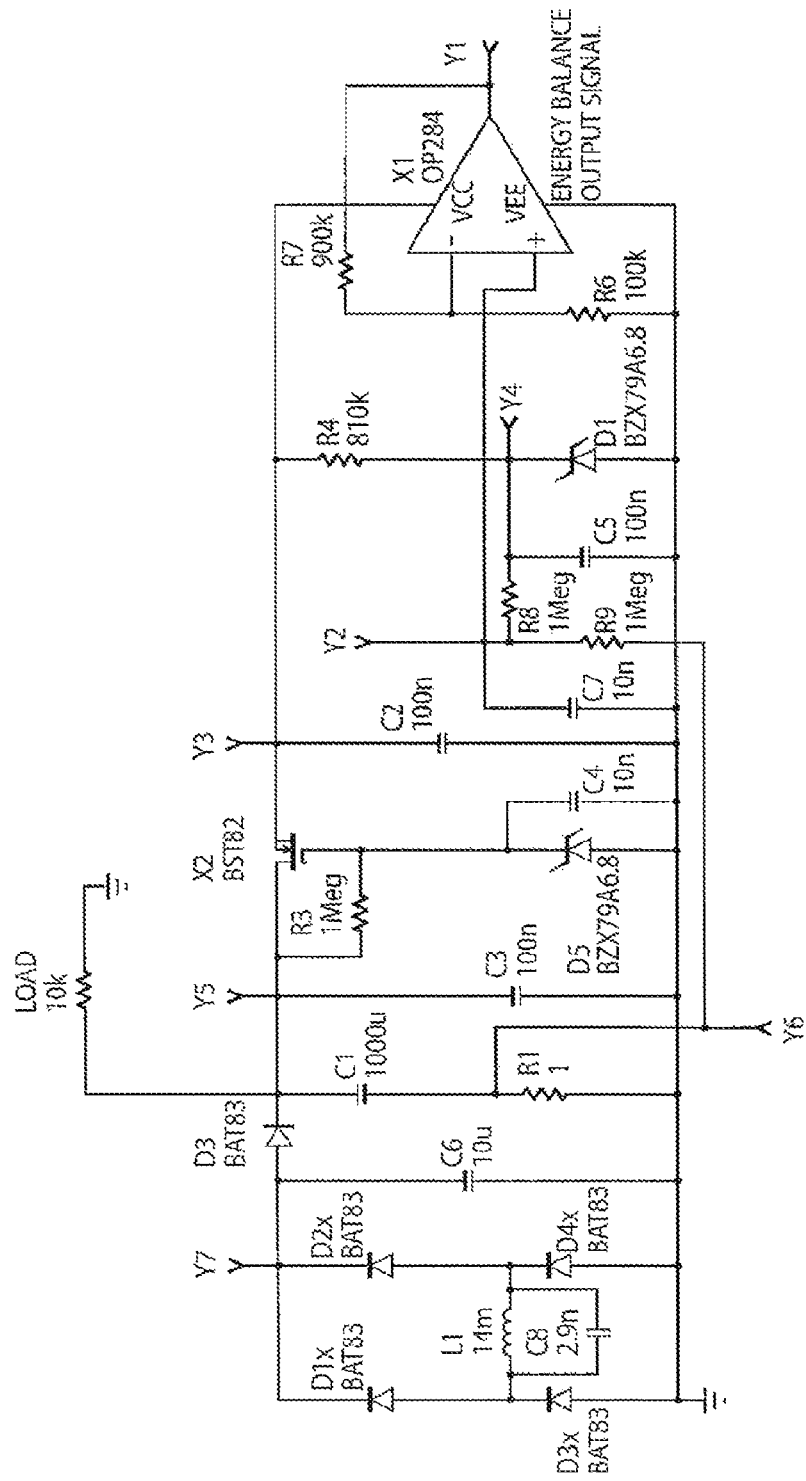
FIG. 61 is a circuit for the arrangement shown in FIG. 60, according to a possible implementation example.

FIG. 61 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the penile implant, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 61 shows a circuit implementation for a system that transfers energy to the implanted energy components of the penile implant of the present invention from outside of the patient's body using inductive energy transfer. An inductive energy transfer system typically uses an external transmitting coil and an internal receiving coil. The receiving coil, L1, is included in the schematic FIG. 44; the transmitting parts of the system are excluded.

The implementation of the general concept of energy balance and the way the information is transmitted to the external energy transmitter can of course be implemented in numerous different ways. The schematic FIG. 61 and the above described method of evaluating and transmitting the information should only be regarded as examples of how to implement the control system.

Circuit Details

In FIG. 61 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 1006 of FIG. 44 could be incorporated in any of the embodiments of FIGS. 47-53, the hydraulic valve shifting device 1014 of FIG. 47 could be incorporated in the embodiment of FIG. 46, and the gear box 1024 could be incorporated in the embodiment of FIG. 45. Please observe that the switch simply could mean any electronic circuit or component.

The embodiments described in connection with FIGS. 58, 60 and 61 identify a method and a system for controlling transmission of wireless energy to implanted energy consuming components of an electrically operable penile implant. Such a method and system will be defined in general terms in the following.

A method is thus provided for controlling transmission of wireless energy supplied to implanted energy consuming components of an penile implant as described above. The wireless energy E is transmitted from an external energy source located outside the patient and is received by an internal energy receiver located inside the patient, the internal energy receiver being connected to the implanted energy consuming components of the penile implant for directly or indirectly supplying received energy thereto. An energy balance is determined between the energy received by the internal energy receiver and the energy used for the penile implant. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an penile implant as described above is thus also provided for controlling transmission of wireless energy supplied to implanted energy consuming components of the penile implant. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the penile implant for directly or indirectly supplying received energy thereto. The system further comprises a determination device adapted to determine an energy balance between the energy received by the internal energy receiver and the energy used for the implantable energy consuming components of the penile implant, wherein the control device controls the transmission of wireless energy from the external energy-transmission device, based on the energy balance determined by the determination device.

Further, the system may comprise any of the following:
A primary coil in the external energy source adapted to transmit the wireless energy inductively to a secondary coil in the internal energy receiver.
The determination device is adapted to detect a change in the energy balance, and the control device controls the transmission of wireless energy based on the detected energy balance change
The determination device is adapted to detect a difference between energy received by the internal energy receiver and energy used for the implantable energy consuming components of the penile implant, and the control device controls the transmission of wireless energy based on the detected energy difference.
The control device controls the external energy-transmission device to decrease the amount of transmitted wireless energy if the detected energy balance change implies that the energy balance is increasing, or vice versa, wherein the decrease/increase of energy transmission corresponds to a detected change rate.
The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.
The energy used for the penile implant is consumed to operate the penile implant, and/or stored in at least one energy storage device of the penile implant.
Where electrical and/or physical parameters of the penile implant and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 62-65 show in more detail block diagrams of four different ways of hydraulically or pneumatically powering an implanted penile implant according to the invention.

Figure 62:
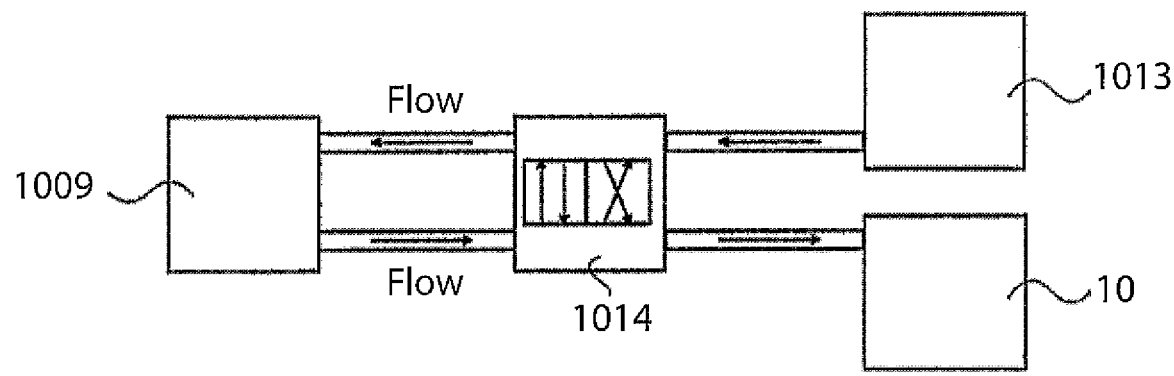

FIG. 62 shows a system as described above with. The system comprises an implanted penile implant 10 and further a separate regulation reservoir 1013, a one way pump 1009 and an alternate valve 1014.

Figure 63:
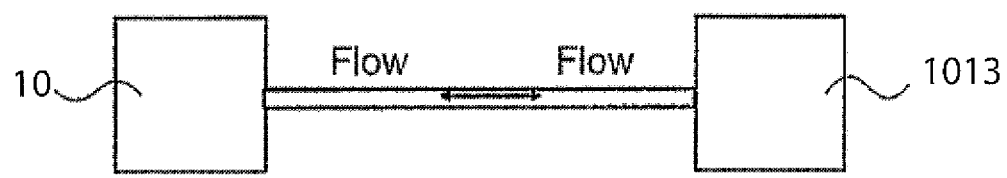

FIG. 63 shows the penile implant 10 and a fluid reservoir 1013. By moving the wall of the regulation reservoir or changing the size of the same in any other different way, the adjustment of the penile implant may be performed without any valve, just free passage of fluid any time by moving the reservoir wall.

Figure 64:
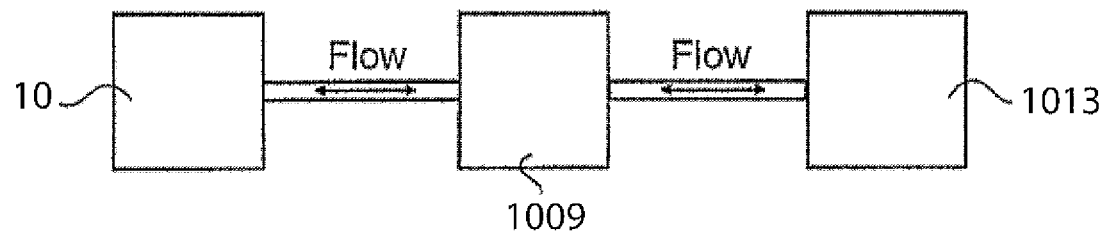

FIG. 64 shows the penile implant 10, a two way pump 1009 and the regulation reservoir 1013.

Figure 65:
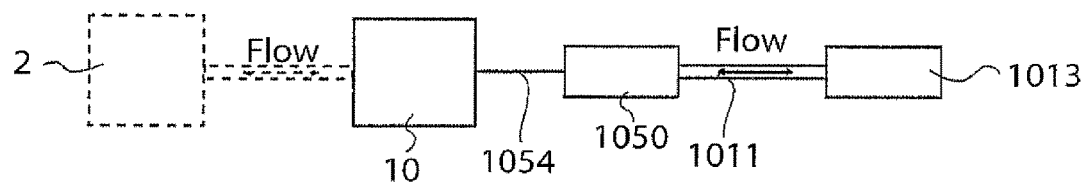

FIG. 65 shows a block diagram of a reversed servo system with a first closed system controlling a second closed system. The servo system comprises a regulation reservoir 1013 and a servo reservoir 1050. The servo reservoir 1050 mechanically controls an implanted penile implant 10 via a mechanical interconnection 1054. The penile implant has an expandable/contactable cavity. This cavity is preferably expanded or contracted by supplying hydraulic fluid from the larger adjustable reservoir 1052 in fluid connection with the penile implant 10. Alternatively, the cavity contains compressible gas, which can be compressed and expanded under the control of the servo reservoir 1050.

The servo reservoir 1050 can also be part of the penile implant itself.

Figure 66:
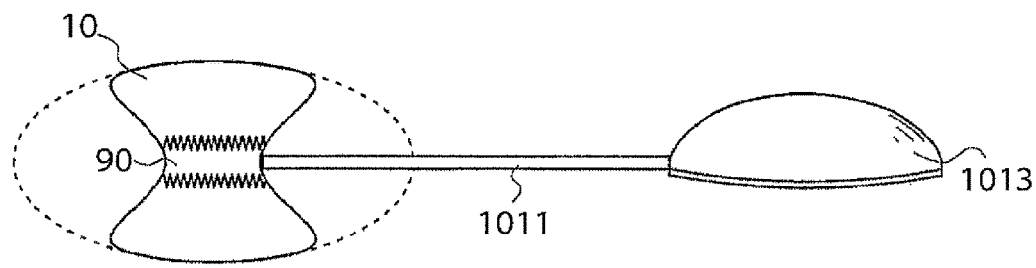
Figure 66:
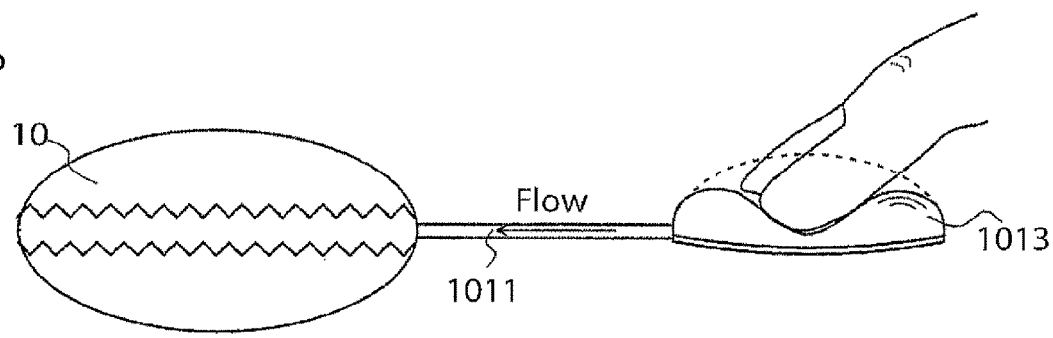
Figure 66:
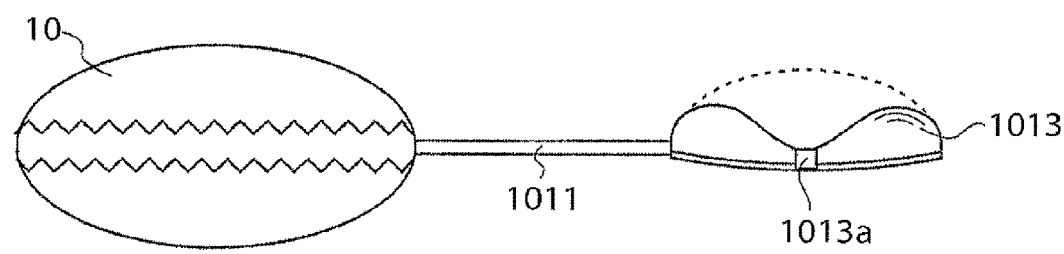
Figure 67:
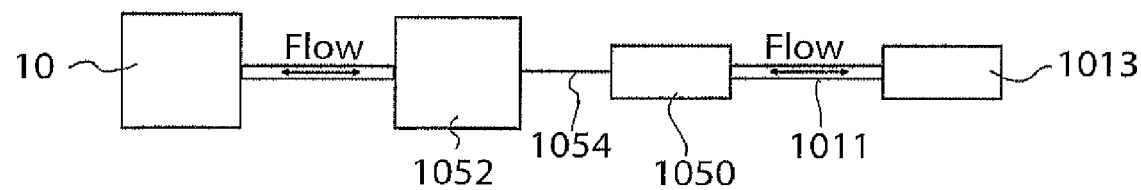

In one embodiment, the regulation reservoir is placed subcutaneous under the patient's skin and is operated by pushing the outer surface thereof by means of a finger. This system is illustrated in FIGS. 25*a-c*. In FIG. 66*a*, a flexible subcutaneous regulation reservoir 1013 is shown connected to a bulge shaped servo reservoir 1050 by means of a conduit 1011. This bellow shaped servo reservoir 1050 is comprised in a a flexible penile implant 10. In the state shown in FIG. 66*a*, the servo reservoir 1050 contains a minimum of fluid and most fluid is found in the regulation reservoir 1013. Due to the mechanical interconnection between the servo reservoir 1050 and the penile implant 10, the outer shape of the penile implant 10 is contracted, i.e., it occupies less than its maximum volume. This maximum volume is shown with dashed lines in the figure.

FIG. 66*b* shows a state wherein a user, such as the patient in with the penile implant is implanted, presses the regulation reservoir 1013 so that fluid contained therein is brought to flow through the conduit 1011 and into the servo reservoir 1050, which, thanks to its bellow shape, expands longitudinally. This expansion in turn expands the penile implant 10 so that it occupies its maximum volume, thereby stretching the stomach wall (not shown), which it contacts.

The regulation reservoir 1013 is preferably provided with means 1013*a* for keeping its shape after compression. This means, which is schematically shown in the figure, will thus keep the penile implant 10 in a stretched position also when the user releases the regulation reservoir. In this way, the regulation reservoir essentially operates as an on/off switch for the system.

An alternative embodiment of hydraulic or pneumatic operation will now be described with reference to FIGS. 67 and 68*a-c*. The block diagram shown in FIG. 67 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted penile implant 10 having an expandable/contactable cavity is in turn controlled by the larger adjustable reservoir 1052 by supply of hydraulic fluid from the larger adjustable reservoir 1052 in fluid connection with the penile implant 10.

Figure 68:
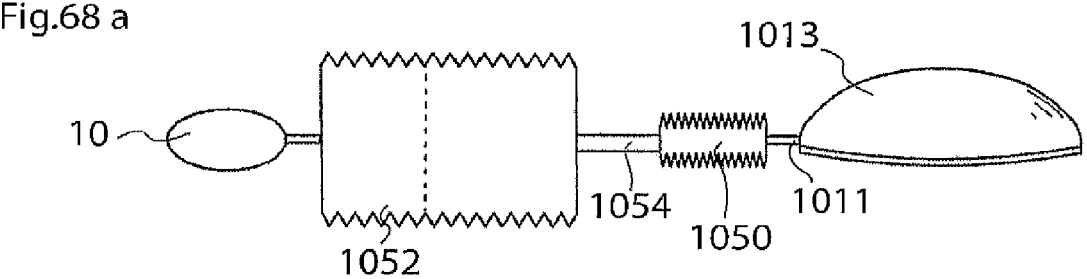
Figure 68:
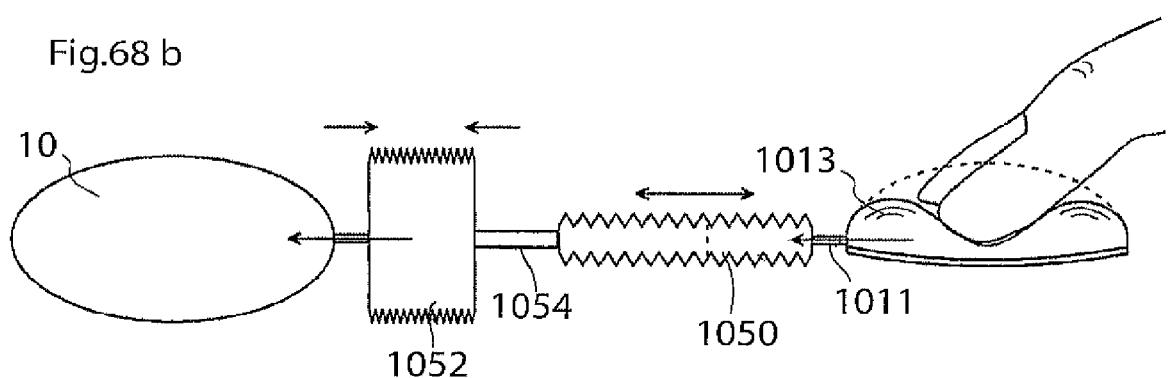
Figure 68:
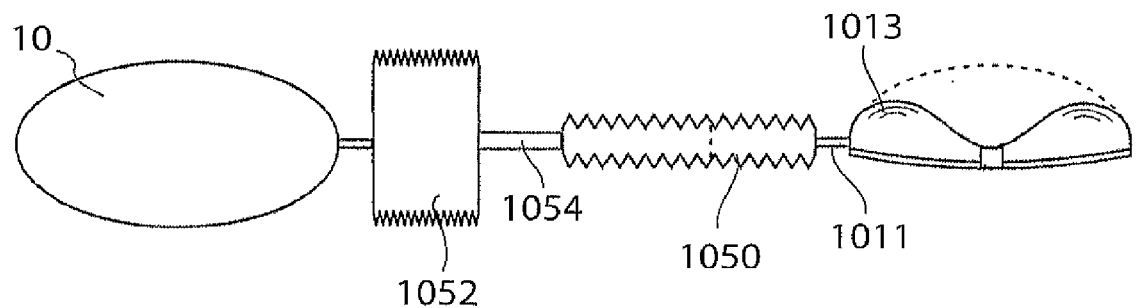

An example of this embodiment will now be described with reference to FIG. 68a-c. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 68*a*, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the penile implant 10. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the penile implant 10. In other words, in this reversed servo, a small volume in the regulation reservoir is compressed with a higher force and this creates a movement of a larger total area with less force per area unit.

Like in the previous embodiment described above with reference to FIGS. 66*a-c*, the regulation reservoir 1013 is preferably provided with means 1013*a* for keeping its shape after compression. This means, which is schematically shown in the figure, will thus keep the penile implant 10 in a stretched position also when the user releases the regulation reservoir. In this way, the regulation reservoir essentially operates as an on/off switch for the system.

Of course a penile implant 10 according to any embodiment and comprising any aspect or feature can be part of a penile prosthesis system 700 and be connected to a manual or powered operating device 702 and a control device 704 and be part of a penile prosthesis system.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

The invention claimed is:

1. A method for implanting a non-invasively and post-operatively adjustable penile implant in a penis of a patient, the implant comprising an expandable portion having a hollow portion adapted to receive a fluid, thereby allowing the expandable portion to be adjustable from a collapsed state into an expanded state, said method comprising the steps of:
   placing a proximal portion of said hollow portion in at least one corpus cavernosum, such that said proximal portion substantially extends on the inside of the male person when implanted in the penis;
   placing a distal portion of said hollow portion in the at least one corpus cavernosum such that said distal portion substantially extends on the outside of the male person when implanted in the penis, wherein the distal portion is placed with an invagination extending into the hollow portion in the collapsed state, and wherein said invagination is adapted to expand the hollow body in a length direction of the penile implant in the expanded state.

2. The method according to claim 1, wherein the step of placing the proximal portion comprises placing the proximal portion in the root part of the penis, which substantially extends on the inside of the body.

3. The method according to claim 2, wherein the step of placing the distal portion comprises placing the distal in the protruding or pendulous part of the penis.

4. The system according to claim 1, wherein the step of placing the proximal portion comprises placing the proximal portion such that a a further invagination, arranged on a proximal part of said penile implant, is formed.

5. The method according to claim 1, further comprising at least one of the following steps:
   creating an opening in the skin or penis wall of the male patient;
   inserting a tube or needle into the patients body;
   filling the tube or needle with a gas and thereby expanding a cavity within the male patients body;
   inserting at least two laparoscopic trocars into said cavity;
   inserting at least one camera trough at least one laparoscopic trocar;
   inserting at least one dissecting tool through at least one laparoscopic trocar;
   dissecting an one area of the sexually responsive tissue, the at least one area being at least one corpus cavernosum;
   placing the proximal portion of said hollow portion in the at least one corpus cavernosum and placing the distal portion of said hollow portion in the at least one corpus cavernosum;
   closing the wound.

6. The method according to claim 1, further comprising implanting the implant in both corpus cavernosum.

7. The method according to claim 1, further comprising the step of placing an operation device in the body of the patient.

8. The method according to claim 1, further comprising placing a implantable internal energy source for powering implantable energy consuming components of the implant within the body of the patient.

9. The method according to claim 8, wherein the energy source is a battery.

10. The method according to claim 7, wherein wherein the steps of placing the penile implant and the step of placing an operation device comprises
   placing an integrated unit comprising the penile implant and an operation device in the same integrated unit,
   placing an control unit and a rechargeable battery remote from the penis, thereby allowing to control said penile implant post-operatively and non-invasively from outside the body to bring a penis to an erected state, when said penile implant is implanted in the corpus cavernosum of the penis and activated or expanded.

11. The method according to claim 1, further comprising the step of placing a reservoir adapted to hold said fluid within the body of the patient.

12. The method according to claim 1, further comprising the step of placing a invagination holding device in part of the corpus cavernosum that extends on the outside of the male person when implanted in the penis, to hold the invagination rotated to face the urethra.

13. The method according to claim 1, further comprising the steps of pressurizing the expandable portion by fluid to bring said expandable portion into said expanded state; and to release the fluid from said expandable portion, to bring said expandable portion into said collapsed state; wherein said fluid further expands the invagination to increase the penile diameter when reaching said expanded state.

14. The method according to claim 1, wherein said longitudinally expandable portion comprises a longitudinal bellows structure that comprises ridges and grooves that extend substantially circumferentially along a part of, along parts of, or along the complete, circumference of said penile implant.

15. The method according to claim 14, wherein the distance between the substantially opposing sides of the ridges and grooves of the longitudinal bellows structure is sufficiently extended to prevent growth of fibrotic tissue from directly interconnecting said substantially opposing sides to an extent that allows the adjustability between the collapsed state and the expanded state.

16. The method according to claim 15, wherein wherein the distance between the substantially opposing sides of the ridges and grooves of the longitudinal bellows structure is greater than 1 mm.

17. The method according to claim 1, wherein said expandable portion comprises a first compartment,
a second compartment, adapted to be filled and pressurized with a fluid, wherein said invagination is arranged at said second compartment, wherein said invagination is adapted to bulge when subjected to fluid pressure and to resume its invaginated form when said fluid pressure is removed, and:
at least one dividing wall separating the first and second compartment by having at least one valve, wherein said at least one valve has a first side or face which is adapted to be closed for fluid up to a predetermined fluid pressure threshold above which said at least one valve is adapted to open, and a second side or face which is adapted to be open for fluid at substantially any pressure, at least for a pressure greater than zero,
wherein said second compartment is adapted to be filled and pressurized with fluid when the fluid pressure in said first compartment exceeds said fluid pressure threshold so that said invagination bulge and increase in diameter and radially expands said penile implant.

18. The penile implant according to claim 1, wherein said expandable portion comprises a first compartment,
a second compartment, adapted to be filled and pressurized with a fluid, wherein said second compartment comprises said invagination, wherein said invagination is adapted to bulge when subjected to fluid pressure and to resume its invaginated form when said fluid pressure is removed, and
at least one dividing wall separating the first and second compartment by having at least one valve, wherein said at least one valve has a first side or face which is adapted to be closed for fluid up to a predetermined fluid pressure threshold above which said at least one valve is adapted to open, and a second side or face which is adapted to be open for fluid at substantially any pressure, at least for a pressure greater than zero,
wherein said second compartment is adapted to be filled and pressurized with fluid when the fluid pressure in said first compartment exceeds said fluid pressure threshold so that said invagination bulge and hence prolongs and increase penile length of said penile implant.

19. The method according to claim 1, wherein the implant comprises two expandable portions.

20. The method according to claim 1, wherein herein said implant comprises a waist portion perpendicular to its longitudinal extension.

* * * * *